US011667948B2

(12) United States Patent
Rodriguez-Palacios et al.

(10) Patent No.: US 11,667,948 B2
(45) Date of Patent: Jun. 6, 2023

(54) METHODS FOR REDUCING OR ALLEVIATING INFLAMMATION IN THE DIGESTIVE TRACT

(71) Applicant: Case Western Reserve University, Cleveland, OH (US)

(72) Inventors: Alexander Rodriguez-Palacios, Cleveland, OH (US); Fabio Cominelli, Shaker Heights, OH (US)

(73) Assignee: CASE WESTERN RESERVE UNIVERSITY, Cleveland, OH (US)

( * ) Notice: Subject to any disclaimer, the term of this patent is extended or adjusted under 35 U.S.C. 154(b) by 118 days.

(21) Appl. No.: 16/275,853

(22) Filed: Feb. 14, 2019

(65) Prior Publication Data
US 2019/0249221 A1 Aug. 15, 2019

Related U.S. Application Data

(60) Provisional application No. 62/630,310, filed on Feb. 14, 2018.

(51) Int. Cl.
*C12Q 1/28* (2006.01)
*C12Q 1/10* (2006.01)
*G01N 21/78* (2006.01)
*G01N 33/52* (2006.01)

(52) U.S. Cl.
CPC ............... *C12Q 1/28* (2013.01); *C12Q 1/10* (2013.01); *G01N 21/78* (2013.01); *G01N 33/52* (2013.01); *C12Y 111/02002* (2013.01)

(58) Field of Classification Search
CPC ........ C12Q 1/28; C12Q 1/10; G01N 33/6893; G01N 2800/06; G01N 2333/908; G01N 2333/24; G01N 2333/195; G01N 33/52; G01N 21/78; C12Y 111/02002
See application file for complete search history.

(56) References Cited

PUBLICATIONS

Sobieszczanska, B. M. et al. 2007. Association of enteroaggregative *Escherichia coli* with irritable bowel syndrome. Clin Microbiol Infect. 13: 404-407. (Year: 2007).*
Hansberry, D. R. et al. 2017. Fecal Myeloperoxidase as a Biomarker for Inflammatory Bowel Disease. Cureus. 9(1): e1004. (Year: 2017).*
Thiruvelan. 2015. IBS Triggers. Gastrodigestivesystem. Retrieved from: https://gastrodigestivesystem.com/smallbowel/IBS-triggers. (Year: 2015).*
Lumen: Boundless Microbiology. 2017. Proteobacteria. Retrieved from: https://courses.lumenlearning.com/boundless-microbiology/chapter/proteobacteria/ (Year: 2017).*
Genta, R. M. et al. 2012. Non-Helicobacter pylori gastritis is common among paediatric patients with inflammatory bowel disease. Alimentary Pharmacology & Therapeutics. 35: 1310-1316. (Year: 2012).*

Kim et al, PLoS ONE, 2012, vol. 7, Issue 10, e47713, p. 1-11.*
Wikipedia, Enterobacteriaceae according to Wikipedia retrieved on Jun. 24, 2021 6 pages of PDF.*
Abou-Donia et al., Journal of Toxicology and Environmental Health, 2008, vol. 71, p. 1415-1429.*
Singh et al., Nature Communications, May 2015, 6:7113; DOI: 10.1038/ncomms8113, p. 1-11.*
Elseweidy et al., Dig. Dis. Sci., 2010, vol. 55, p. 2770-2777.*
Abbott, D. Wade, et al. "The molecular basis of glycogen breakdown and transport in *Streptococcus pneumoniae*." Molecular microbiology 77.1 (2010): 183-199.
Aboud, OA Aboud, et al. "Epidemiology of *Salmonella* sp. in California cull dairy cattle: prevalence of fecal shedding and diagnostic accuracy of pooled enriched broth culture of fecal samples." PeerJ 4 (2016): e2386-e2386.
Abou-Donia, Mohamed B., et al. "Splenda alters gut microflora and increases intestinal p-glycoprotein and cytochrome p-450 in male rats." Journal of Toxicology and Environmental Health, Part A 71.21 (2008): 1415-1429.
Stappenbeck, Thaddeus S., and Herbert W. Virgin. "Accounting for reciprocal host-microbiome interactions in experimental science." Nature 534.7606 (2016): 191-199.
Agus, Allison, et al. "Western diet induces a shift in microbiota composition enhancing susceptibility to Adherent-Invasive *E. coli* infection and intestinal inflammation." Scientific reports 6 (2016): 19032.
Barrett, Kim E., and Declan F. McCole. "Hydrogen peroxide scavenger, catalase, alleviates ion transport dysfunction in murine colitis." Clinical and Experimental Pharmacology and Physiology 43.11 (2016): 1097-1106.
Bradley, Patrick H., and Katherine S. Pollard. "Proteobacteria explain significant functional variability in the human gut microbiome." Microbiome 5.1 (2017): 36.
Brown, Amy C., and Minakshi Roy. "Does evidence exist to include dietary therapy in the treatment of Crohn's disease?." Expert review of gastroenterology & hepatology 4.2 (2010): 191-215.
Bustos, D., et al. "Cuantificación de neutrófilos fecales mediante la determinaciàn de MPO (Mieloperoxidasa) en pacientes con diarrea invasiva." Acta gastroenterol. latinoam (2000): 85-7.
Cadwell, Ken, et al. "Virus-plus-susceptibility gene interaction determines Crohn's disease gene Atg16L1 phenotypes in intestine." Cell 141.7 (2010): 1135-1145.

(Continued)

*Primary Examiner* — Kade Ariani
(74) *Attorney, Agent, or Firm* — Tarolli, Sundheim, Covell & Tummino, LLP

(57) ABSTRACT

One aspect of the present disclosure can include a method for reducing or alleviating inflammation in the digestive tract of a subject in need thereof that consumes a disruptive dietary component. One step of the method can include assaying a previously obtained fecal sample from the subject for the presence of one or more Proteobacteria and an activity level of a peroxidase enzyme. The subject can decrease ingestion of the disruptive dietary component if the assayed presence of the one or more Proteobacteria and the activity level of the peroxidase enzyme are increased as compared to control levels.

9 Claims, 35 Drawing Sheets

(56) References Cited

PUBLICATIONS

Chakravorty, Soumitesh, et al. "A detailed analysis of 16S ribosomal RNA gene segments for the diagnosis of pathogenic bacteria." Journal of microbiological methods 69.2 (2007): 330-339.
Chassaing, Benoit, et al. "Dietary emulsifiers impact the mouse gut microbiota promoting colitis and metabolic syndrome." Nature 519.7541 (2015): 92-96.
Dohoo, I., W. Martin, and H. Stryhn. "Confounder bias: analytic control and matching." Veterinary epidemiologic research. Prince Edward Island: AVC Inc (2003): 235-71.
Corridoni, D., et al. "Genetic deletion of the bacterial sensor NOD2 improves murine Crohn's disease-like ileitis independent of functional dysbiosis." Mucosal immunology 10.4 (2017): 971-982.
Couturier-Maillard, Aurélie, et al. "NOD2-mediated dysbiosis predisposes mice to transmissible colitis and colorectal cancer." The Journal of clinical investigation 123.2 (2013).
Dheer, Rishu, et al. "Intestinal epithelial toll-like receptor 4 signaling affects epithelial function and colonic microbiota and promotes a risk for transmissible colitis." Infection and immunity 84.3 (2016): 798-810.
Limdi, Jimmy K., Divya Aggarwal, and John T. McLaughlin. "Diet and Exacerbation of Inflammatory Bowel Disease Symptoms—Food for Thought." Inflammatory bowel diseases 22.3 (2016): E11.
Limdi, Jimmy K., Divya Aggarwal, and John T. McLaughlin. "Dietary practices and beliefs in patients with inflammatory bowel disease." Inflammatory bowel diseases 22.1 (2016): 164-170.
Litvak, Yael, et al. "Dysbiotic Proteobacteria expansion: a microbial signature of epithelial dysfunction." Current opinion in microbiology 39 (2017): 1-6.
Eppinga, Hester. "Linking Gut to Skin: the Microbiome and Chronic Inflammatory Diseases." (2016).
FDA Consumer magazine "Artificial Sweeteners: No Calories . . . Sweet!", https://permanent.access.gpo.gov/lps1609/www.fda.gov/fdac/features/2006/406_sweeteners.html, pp. 1-3, accessed Mar. 22, 2019.
Forbes, Alastair, et al. "ESPEN guideline: Clinical nutrition in inflammatory bowel disease." Clinical Nutrition 36.2 (2017): 321-347.
Babbs, Charles F. "Free radicals and the etiology of colon cancer." Free Radical Biology and Medicine 8.2 (1990): 191-200.
Gillevet, Patrick, et al. "Quantitative assessment of the human gut microbiome using multitag pyrosequencing." Chemistry & biodiversity 7.5 (2010): 1065-1075.
Goker, Markus, et al. "Complete genome sequence of *Odoribacter splanchnicus* type strain (1651/6 T)." Standards in genomic sciences 4.2 (2011): 200.
Hansen, Tanja Stenbaek, et al. "Environmental factors in inflammatory bowel disease: a case-control study based on a Danish inception cohort." Journal of Crohn's and Colitis 5.6 (2011): 577-584.
Hart, Ailsa L., et al. "What are the top 10 research questions in the treatment of inflammatory bowel disease? A priority setting partnership with the James Lind Alliance." Journal of Crohn's and Colitis 11.2 (2017): 204-211.
Herigstad, Becky, Martin Hamilton, and Joanna Heersink. "How to optimize the drop plate method for enumerating bacteria." Journal of microbiological methods 44.2 (2001): 121-129.
Hoarau, Gautier, et al. "Bacteriome and mycobiome interactions underscore microbial dysbiosis in familial Crohn's disease." MBio 7.5 (2016): e01250-16.
Huijsdens, Xander W., et al. "Quantification of bacteria adherent to gastrointestinal mucosa by real-time PCR." Journal of clinical microbiology 40.12 (2002): 4423-4427.
Huse, Susan M., et al. "A core human microbiome as viewed through 16S rRNA sequence clusters." PLoS one 7.6 (2012).
Bouvet, Jean-Pierre, et al. "IgM reassociation in the absence of J-chain." Immunology letters 15.1 (1987): 27-31.

Kozaiwa, Kosuke, et al. "Identification of a quantitative trait locus for ileitis in a spontaneous mouse model of Crohn's disease: SAMP1/YitFc." Gastroenterology 125.2 (2003): 477-490.
Lucke, Katja, et al. "Prevalence of Bacteroides and *Prevotella* spp. in ulcerative colitis." Journal of medical microbiology 55.5 (2006): 617-624.
Manichanh, Chaysavanh, et al. "Reduced diversity of faecal microbiota in Crohn's disease revealed by a metagenomic approach." Gut 55.2 (2006): 205-211.
McCune, Broc T., et al. "Noroviruses co-opt the function of host proteins VAPA and VAPB for replication via a phenylalanine-phenylalanine-acidic-tract-motif mimic in nonstructural viral protein NS1/2." MBio 8.4 (2017): e00668-17.
Morrison, Peter J., et al. "Differential requirements for IL-17A and IL-22 in cecal versus colonic inflammation induced by Helicobacter hepaticus." The American journal of pathology 185.12 (2015): 3290-3303.
Dore, J., et al. "Most probable number enumeration of H2-utilizing acetogenic bacteria from the digestive tract of animals and man." FEMS microbiology Letters 130.1 (1995): 7-12.
Mukherjee, Pranab K., et al. "Oral mycobiome analysis of HIV-infected patients: identification of *Pichia* as an antagonist of opportunistic fungi." PLoS pathogens 10.3 (2014).
Myers, Jeremy N., et al. "Implications of the colonic deposition of free hemoglobin-α chain: a previously unknown tissue by-product in inflammatory bowel disease." Inflammatory bowel diseases 20.9 (2014): 1530-1547.
Nadkarni, Mangala A., et al. "Determination of bacterial load by real-time PCR using a broad-range (universal) probe and primers set." Microbiology 148.1 (2002): 257-266.
Nickerson, Kourtney P., et al. "The dietary polysaccharide maltodextrin promotes *Salmonella* survival and mucosal colonization in mice." PLoS One 9.7 (2014).
Nickerson, Kourtney P., and Christine McDonald. "Crohn's disease-associated adherent-invasive *Escherichia coli* adhesion is enhanced by exposure to the ubiquitous dietary polysaccharide maltodextrin." PloS one 7.12 (2012): e52132.
Norman, Jason M., Scott A. Handley, and Herbert W. Virgin. "Kingdom-agnostic metagenomics and the importance of complete characterization of enteric microbial communities." Gastroenterology 146.6 (2014): 1459-1469.
O'Sullivan, Maria, and Colm O'Morain. "Nutrition in inflammatory bowel disease." Best practice & research Clinical gastroenterology 20.3 (2006): 561-573.
Pizarro, Theresa T., et al. "SAMP1/YitFc mouse strain: a spontaneous model of Crohn's disease-like ileitis." Inflammatory bowel diseases 17.12 (2011): 2566-2584.
Qin, Xiaofa. "Etiology of inflammatory bowel disease: a unified hypothesis." World journal of gastroenterology: WJG 18.15 (2012): 1708.
Vandeputte, Doris, et al. "Quantitative microbiome profiling links gut community variation to microbial load." Nature 551.7681 (2017): 507-511.
Reidl, J. O. A. C. H. I. M., and W. I. N. F. R. I. E. D. Boos. "The malX malY operon of *Escherichia coli* encodes a novel enzyme II of the phosphotransferase system recognizing glucose and maltose and an enzyme abolishing the endogenous induction of the maltose system." Journal of bacteriology 173.15 (1991): 4862-4876.
Rodriguez-Palacios, Alex, et al. "Stereomicroscopic 3D-pattern profiling of murine and human intestinal inflammation reveals unique structural phenotypes." Nature communications 6.1 (2015): 1-16.
Rodriguez-Palacios, Alexander, Sheldon Bai, and Fabio Cominelli. "Tu1934 Whole-Genome Sequencing and Transcriptome Analysis of Mice With Progressive Crohn's Disease-Like Ileitis." Gastroenterology 146.5 (2014): S-876.
Rodriguez-Palacios, Alexander, Natalia Aladyshkina, and Fabio Cominelli. "Stereomicroscopy and 3D-target myeloperoxidase intestinal phenotyping following a fecal flora homogenization protocol." Protocol Exchange 6 (2015): 1-24.
Sakamoto, Naomasa, et al. "Dietary risk factors for inflammatory bowel disease A Multicenter Case-Control Study in Japan." Inflammatory bowel diseases 11.2 (2005): 154-163.
Scanlan, Pauline D., et al. "Culture-independent analyses of temporal variation of the dominant fecal microbiota and targeted

(56) References Cited

PUBLICATIONS bacterial subgroups in Crohn's disease." Journal of clinical microbiology 44.11 (2006): 3980-3988.

Schloss, Patrick D., et al. "Introducing mothur: open-source, platform-independent, community-supported software for describing and comparing microbial communities." Appl. Environ. Microbiol. 75.23 (2009): 7537-7541.

Segata, Nicola, et al. "Metagenomic microbial community profiling using unique clade-specific marker genes." Nature methods 9.8 (2012): 811.

Shen, Xiang Jun, et al. "Molecular characterization of mucosal adherent bacteria and associations with colorectal adenomas." Gut microbes 1.3 (2010): 138-147.

Shin, Na-Ri, Tae Woong Whon, and Jin-Woo Bae. "Proteobacteria: microbial signature of dysbiosis in gut microbiota." Trends in biotechnology 33.9 (2015): 496-503.

Sigman, M., et al. "Non-Invasive Measurement of Intestinal Inflammation Following Burn Injury." Shock. vol. 37. 530 Walnut St, Philadelphia, PA 19106-3621 USA: Lippincott Williams & Wilkins, 2012.

Puyet, Antonio, and Manuel Espinosa. "Structure of the maltodextrin-uptake locus of *Streptococcus pneumoniae*: correlation to the *Escherichia coli* maltose regulon." Journal of molecular biology 230.3 (1993): 800-811.

Suez, Jotham, et al. "Artificial sweeteners induce glucose intolerance by altering the gut microbiota." Nature 514.7521 (2014): 181-186.

Suez, Jotham, et al. "Non-caloric artificial sweeteners and the microbiome: findings and challenges." Gut microbes 6.2 (2015): 149-155.

Thom, George, and Mike Lean. "Is there an optimal diet for weight management and metabolic health?." Gastroenterology 152.7 (2017): 1739-1751.

George, Melissa M., et al. "Utilization of composite fecal samples for detection of anthelmintic resistance in gastrointestinal nematodes of cattle." Veterinary parasitology 240 (2017): 24-29.

Vaishnava, Shipra, et al. "The antibacterial lectin RegIII? promotes the spatial segregation of microbiota and host in the intestine." Science 334.6053 (2011): 255-258.

Walters, William A., Zech Xu, and Rob Knight. "Meta-analyses of human gut microbes associated with obesity and IBD." FEBS letters 588.22 (2014): 4223-4233.

Zhulina, Yaroslava, et al. "Subclinical inflammation with increased neutrophil activity in healthy twin siblings reflect environmental influence in the pathogenesis of inflammatory bowel disease." Inflammatory bowel diseases 19.8 (2013): 1725-1731.

Rodriguez-Palacios-Palacios, Alexander, Abigail Raffner Basson, and Fabio Cominelli. "Artificial Sweeteners and Whole-food Science: Could Mice Help Clinicians Make Diet Recommendations for IBD Patients?." Gastroenterology (2021): S0016-5085.

Dai, Cong, Min Jiang, and Ming-Jun Sun. "Fecal markers in the management of inflammatory bowel disease." Postgraduate medicine 130.7 (2018): 597-606.

Brown, S. R., et al. "The Association of Coloproctology of Great Britain and Ireland consensus guidelines in surgery for inflammatory bowel disease." Colorectal Disease 20 (2018): 3-117.

Matsuoka, Katsuyoshi, et al. "Evidence-based clinical practice guidelines for inflammatory bowel disease." Journal of gastroenterology 53.3 (2018): 305-353.

Barrett, Perry, Julian G. Mercer, and Peter J. Morgan. "Preclinical models for obesity research." Disease models & mechanisms 9.11 (2016): 1245-1255.

Casazza, Krista, et al. "Weighing the evidence of common beliefs in obesity research." Critical reviews in food science and nutrition 55.14 (2015): 2014-2053.

Ioannidis, John PA. "Why most published research findings are false." PLoS medicine 2.8 (2005): e124.

Lutz, Thomas A., and Stephen C. Woods. "Overview of animal models of obesity." Current protocols in pharmacology 58.1 (2012): 5-61.

Kelly, S. "Mouse microbes may make scientific studies harder to replicate." Science 353 (2016): 741-743.

\* cited by examiner

10-FOLD DILUTION FACTOR:

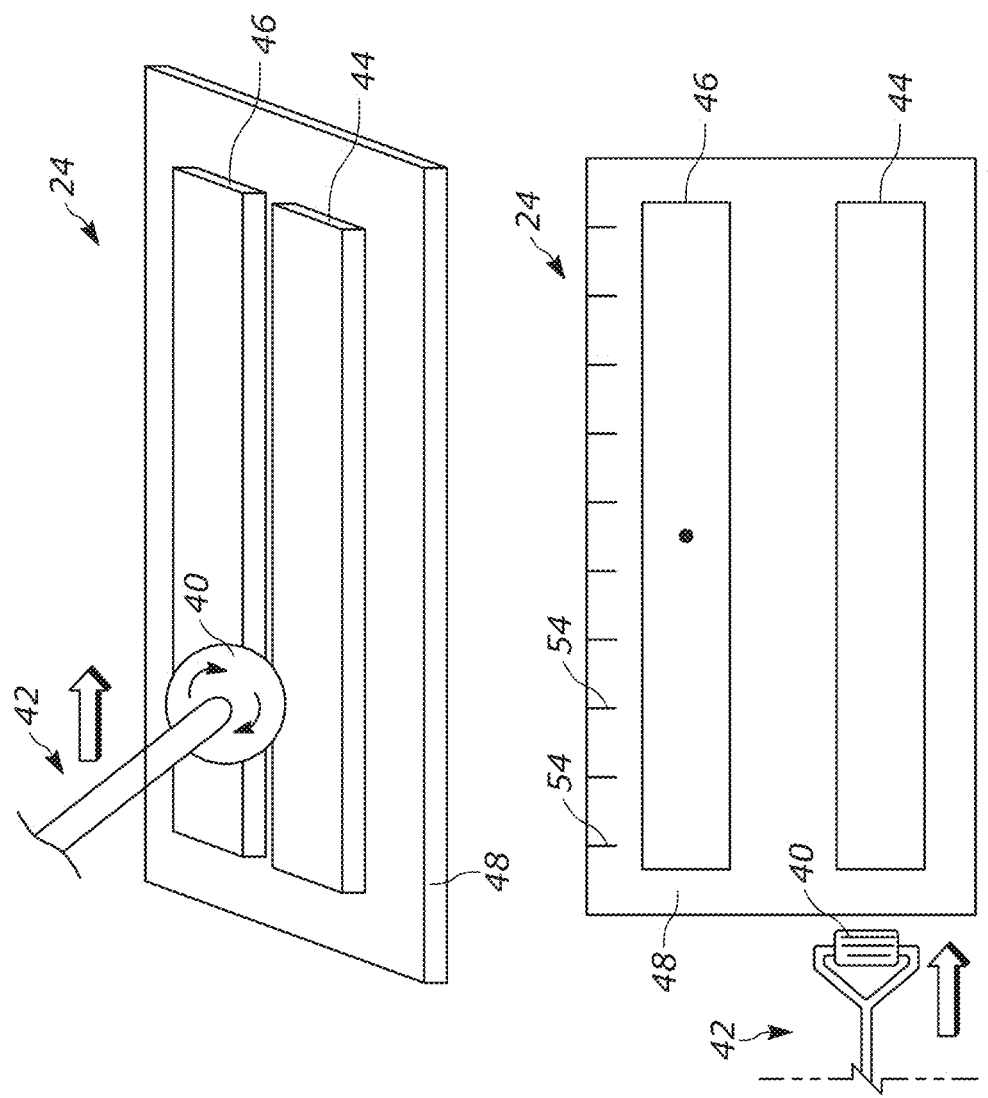

METHODS FOR REDUCING OR ALLEVIATING INFLAMMATION IN THE DIGESTIVE TRACT

RELATED APPLICATION

This application claims priority to U.S. Provisional Application Ser. No. 62/630,310, filed Feb. 14, 2018, entitled "FECAL TEST BASED ON MYELOPEROXIDASE, PROTEOBACTERIA, AND LIPOPOLYSACCHARIDES DETECTION TO MONITOR INTESTINAL INFLAMMATION AND MICROBIAL CHANGES IN RESPONSE TO DIET", the entirety of which is hereby incorporated by reference for all purposes.

TECHNICAL FIELD

The present disclosure relates generally to therapies for inflammatory diseases of the digestive tract, such as Crohn's disease, and, more particularly, to therapies for reducing or alleviating inflammation in the digestive tract of a subject in need thereof that consumes a disruptive dietary component, such as a non-caloric artificial sweetener.

BACKGROUND

Recent self-assessment dietary surveys indicate that ~10% of patients suffering from inflammatory bowel disease (IBD) believe that "sugary foods" worsen the severity of their symptoms and trigger flare-ups. Although nutrition has long been considered critical to improving malnutrition and iron deficiency in severe IBD, there are currently no evidence-based dietary guidelines to help IBD patients manage their own diet. Dietary habits deemed unhealthy (e.g., "Western" diets, rich in fats and sugars) are believed to alter the gut microbiome and either directly or indirectly trigger IBD. Despite substantial progress in our knowledge of acute models of intestinal inflammation, the precise effect of "multi-ingredient" artificial sweeteners on exacerbation of IBD remains unclear.

The ongoing and increased prevalence of obesity, which coincides with the rise of IBD diagnoses, indicates that there is a possible link between the risk factors of both diseases. Due to the growing obesity epidemic and the pressure to avoid sugar to reduce caloric intake, the food industry and consumers are using artificial sweeteners as substitutes for "table sugar." The main ingredient of sugar is often sucrose, a disaccharide of glucose and fructose. Instead of sucrose, artificial sweeteners (e.g., SPLENDA® (sucralose)) use "sucralose" as a noncaloric sweetening ingredient, typically at 1% concentration, mixed with a filling ingredient (99%) that provides texture and volume. The most commonly used filler is maltodextrin, a nutritive polysaccharide regarded as inert and affirmed as "generally regarded as safe" by the US Food and Drug Administration. However, studies indicate that neither sucralose nor maltodextrin is biologically inert. In fact, the potential adverse effects of artificial sweeteners across various diseases are controversial as they vary with the diseases and human populations studied (e.g., obesity, diabetes).

SUMMARY

One aspect of the present disclosure can include a method for reducing or alleviating inflammation in the digestive tract of a subject in need thereof that consumes a disruptive dietary component. One step of the method can include assaying a previously obtained fecal sample from the subject for the presence of one or more Proteobacteria and an activity level of a peroxidase enzyme. The subject can decrease ingestion of the disruptive dietary component if the assayed presence of the one or more Proteobacteria and the activity level of the peroxidase enzyme are increased as compared to control levels.

Another aspect of the present disclosure can include a method for reducing or alleviating intestinal dysbiosis and intestinal myeloperoxidase (MPO) tissue reactivity in a subject that consumes a non-caloric artificial sweetener. The subject can have, or be suspected of having, an inflammatory condition of the digestive tract. One step of the method can include assaying a previously obtained fecal sample from the subject for the presence of Enterobacteriaceae (e.g., a coliform, such as *E. coli*) and an activity level of MPO. The subject can decrease ingestion of the non-caloric artificial sweetener if the assayed presence of Enterobacteriaceae and the activity level of MPO are increased as compared to control levels.

Another aspect of the present disclosure can include a kit for performing the methods of the present application.

BRIEF DESCRIPTION OF THE DRAWINGS

The foregoing and other features of the present disclosure will become apparent to those skilled in the art to which the present disclosure relates upon reading the following description with reference to the accompanying drawings, in which:

FIG. 1A, En face stereomicroscopic images of healthy AKR ileal mucosa (top image) and SAMP cobblestone ileitis (bottom image); schematic illustration of metagenomic sampling design in SPF facilities (pooled feces in experiment 1 [summer] vs individual sampling in experiment 2 [8 months later, spring]). FIG. 1B, Multivariable unsupervised hierarchical analysis of metagenomic fecal bacterial abundance from 36 mice pooled as 6 mice per age group (7, 22, and 55 weeks old). Note clustering of AKR and SAMP samples as separate clades. Arrows illustrate distinct families, ranked by abundance across all samples. FIG. 1C, Compared with AKR, the SAMP metagenome have greater bacterial diversity (Shannon diversity). FIG. 1D, Boxplots reveal reduction of Firmicutes (Lactobacillaceae and Clostridiales) and expansion of Bacteroidetes families in SAMP (e.g., Bacteroidaceae, Rickenellaceae, Sphingobacteriaceae). FIG. 1E, Circular diagram of relative taxonomic metagenomic abundance in phylogenetic tree format highlights significant enrichment of Helicobacteraceae (Proteobacteria phylum), and 4 of 6 known Bacteroidetes phylum families (Bacteroidaceae, Rickenellaceae, Porphyromonadaceae, and Prevotellaceae) in SAMP mice (1-tailed Fisher exact P=0.046).

FIG. 2A, Individual fecal metagenomic analysis of breeder mice was performed 8 months after the previously pooled fecal sampling experiment, demonstrating bacterial profiles with reproducible cluster within pairs of breeders for each individual cage. Squares highlight absence of Helicobacteraceae in Helicobacteraceae-negative SAMP colony. When present, Helicobacteraceae was highly abundant in the feces of positive mice. Analysis highlights within-cage mouse microbiota individualities, e.g., Enterococcaceae. FIG. 2B, Boxplots, showing averages for each cage, reveal high abundance of Bacteroidaceae in SAMP mice (compared with experiment 1 in FIG. 1D). FIG. 2C, the abundance of other Bacteroidetes is shown by boxplots. FIG. 2D, Compared with AKR and B6 mice, SAMP had a significantly higher level of Enterobacteracea (a family that contains *Escherichia coli*). Notice marked abundance of dichotomous variability of Helicobacteraceae in mice. FIG. 2E, Gel electrophoresis of PCR amplified target regions of *Helicobacter* spp. within the 16S rRNA gene from fecal DNA of random mice form our SAMP and AKR colony, 4 months after the individual fecal metagenomic experiment. Notice high band intensity in SAMP (asterisks). Universal and PCR-specific primers were used to generate full or partial gene amplicons (1500 or 400 bp). FIG. 2F, Histological inflammation scores of distal ileum from rederived *Helicobacter*-negative SAMP compared with that of the SAMP colony show no differences. Notice wider variability in *Helicobacter*-positive mice. FIG. 2G, Representative snapshot of videostereomicroscopy shows unchanged morphological appearance of ileal mucosal surface in *Helicobacter*-negative SAMP mice. Scale=500 um.

Figure 3A:
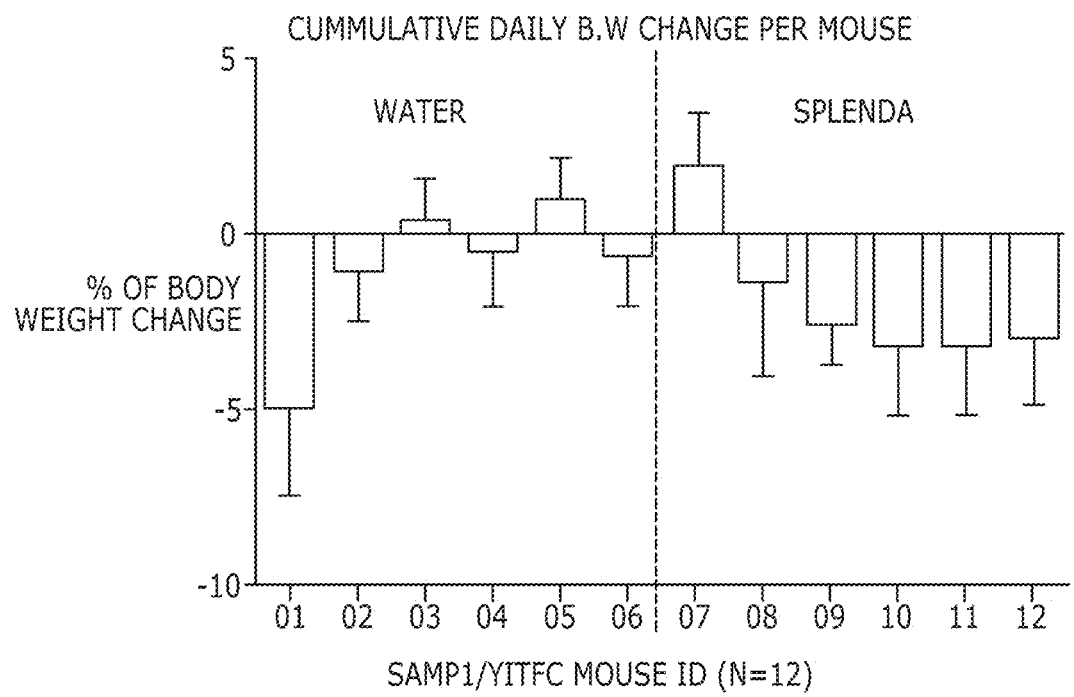
FIGS. 3A-G show effects of SPLENDA® (sucralose) on body weight, fecal bacteria, and glucose tolerance in SAMP myeloperoxidase (MPO) activity in mice with ileitis.
Figure 3B:
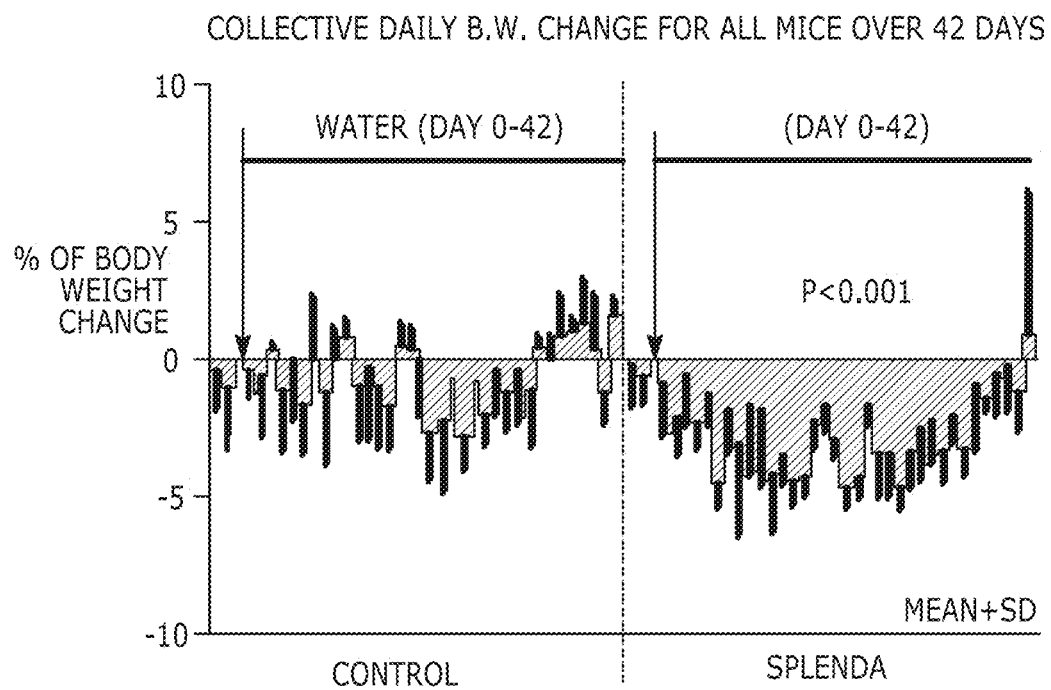
Figure 3C:
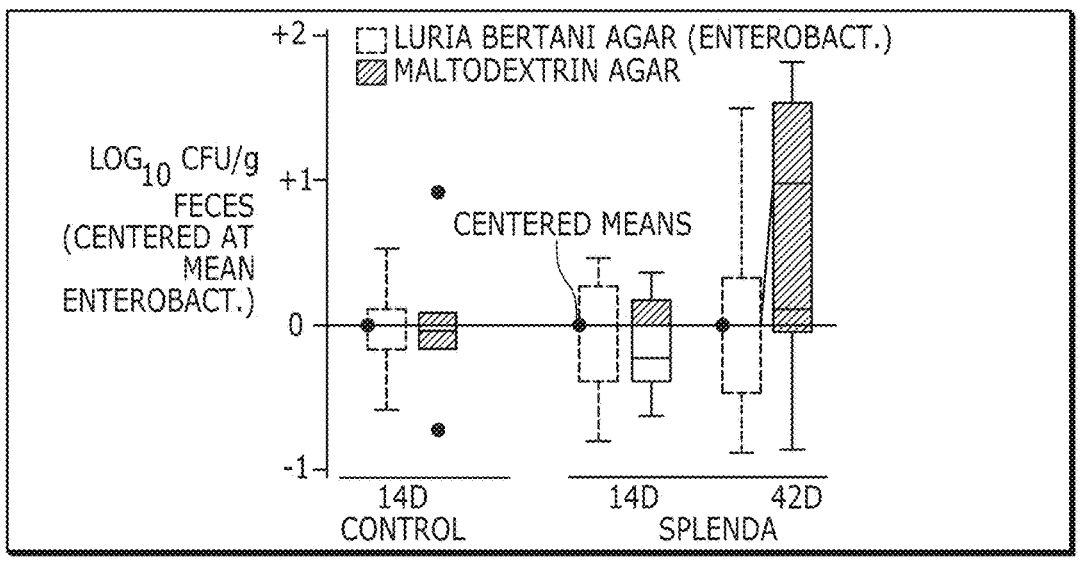
Figure 3D:
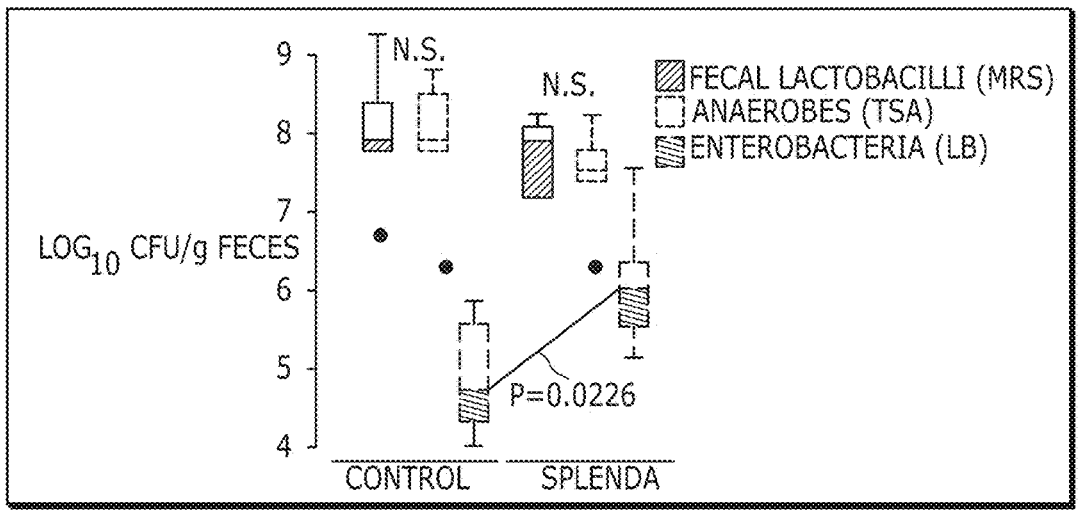
Figure 3E:
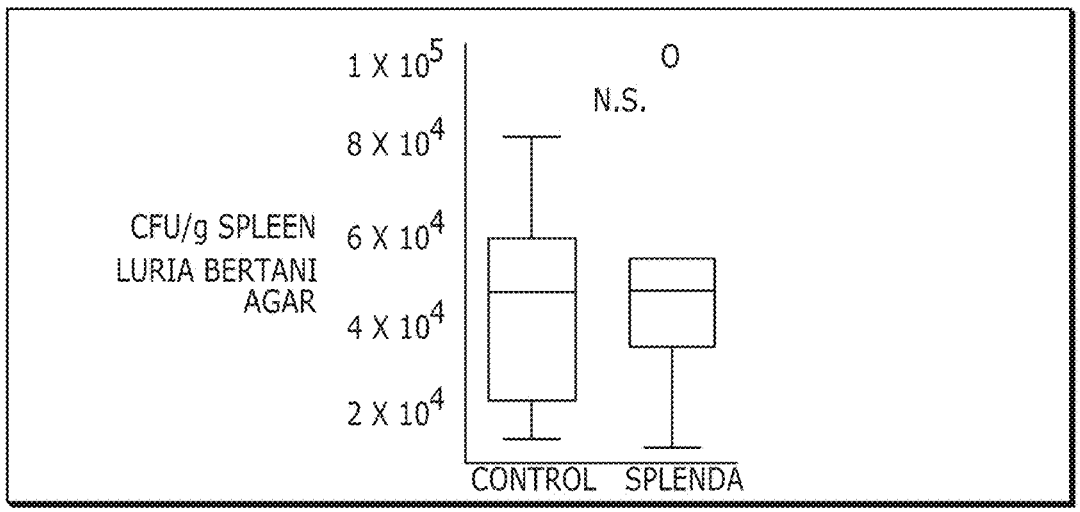
Figure 3F:
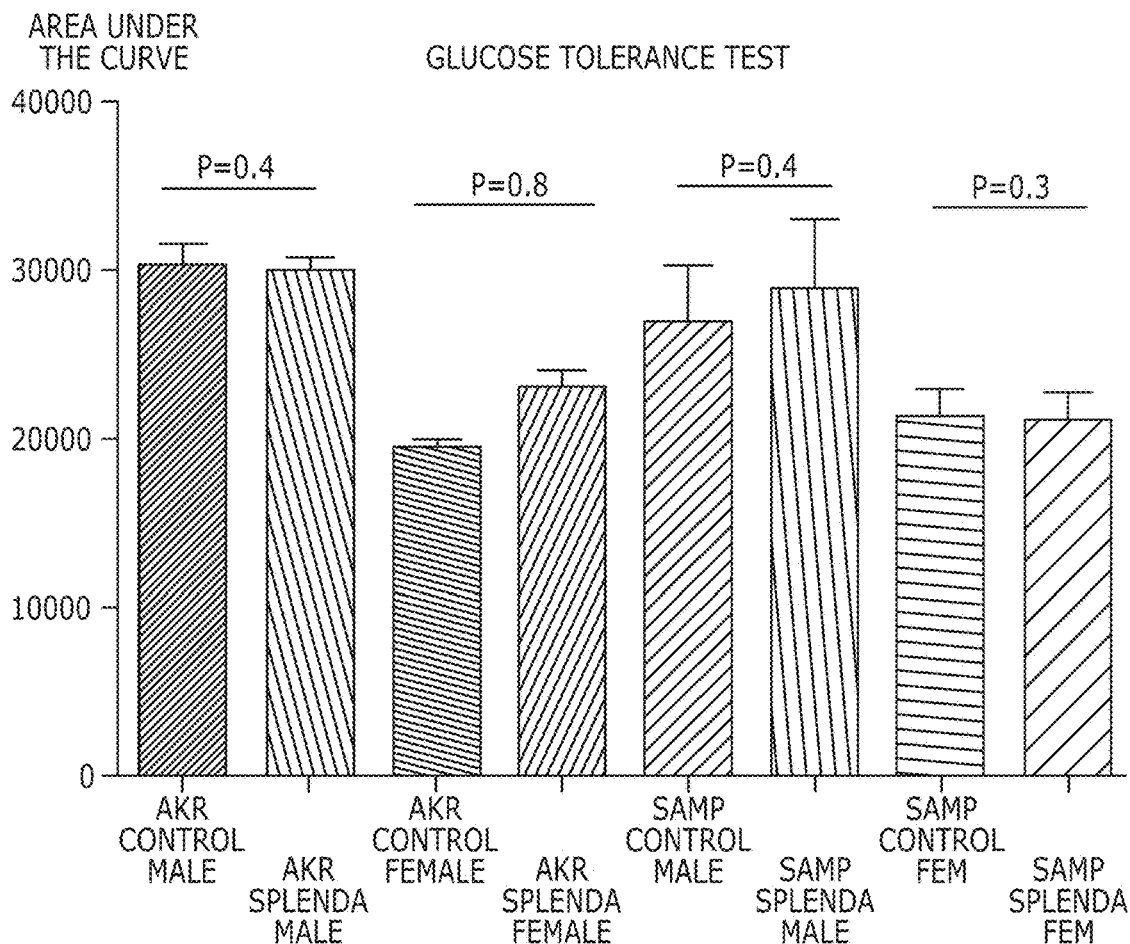
Figure 3G:
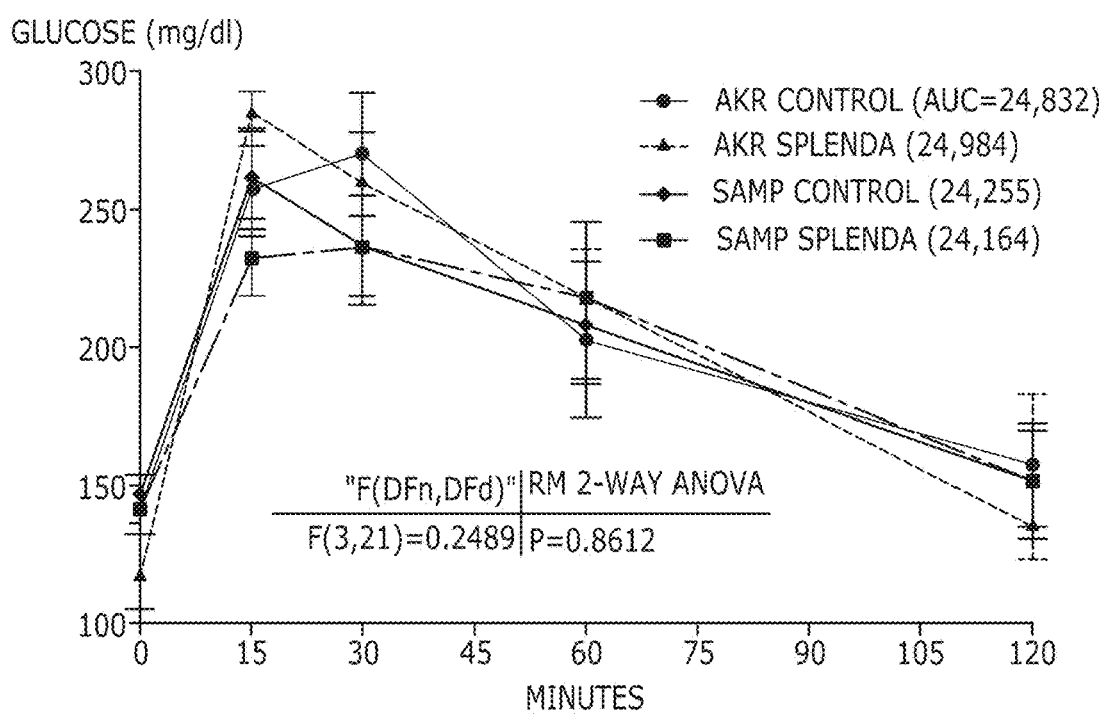

| SAMP1/YitFc | Treatment | N | Minimum | Q1 | Median | Q3 | Maximum | 95% Median CI |
|---|---|---|---|---|---|---|---|---|
| Colon | H2O | 7 | 5.133 | 6.372 | 8.437 | 10.560 | 16.991 | (6.041, 12.275) |
|  | Splenda ® 3.5% | 7 | 3.127 | 3.481 | 7.316 | 10.855 | 23.245 | (3.386, 14.159) |
| Ileum | H2O | 7 | 79.35 | 92.30 | 103.72 | 150.27 | 153.22 | (88.85, 151.05) |
|  | Splenda ® 3.5% | 7 | 70.68 | 124.54 | 172.39 | 223.83 | 294.28 | (110.18, 242.62) |
| AKR/J mice |  |  |  |  |  |  |  |  |
| Colon | H2O | 5 | 2.5369 | 2.5959 | 3.1268 | 3.6283 | 3.7758 | (2.5369, 3.7758) |
|  | Splenda ® 3.5% | 6 | 0.5310 | 2.6106 | 4.1003 | 6.6077 | 6.6077 | (1.5213, 6.6077) |
| Ileum | H2O | 5 | 3.07 | 3.07 | 3.07 | 46.17 | 48.97 | (3.07, 48.97) |
|  | Splenda ® 3.5% | 6 | 5.192 | 7.670 | 12.611 | 48.230 | 53.540 | (6.372, 51.011) | mice. FIG. 3A, Mean body weight change in 12 SAMP mice (individually caged, 7 days of adaptation, more than 42 days of supplementation of drinking water with and without low-dose SPLENDA® (sucralose)). FIG. 3B, Daily group average of body weight change over time; low SPLENDA® (sucralose) dose. FIG. 3C, Bacterial enumeration from feces using standard LB agar (used for enterobacteria) and in-house "maltodextrin agar." Notice maltodextrin agar yielded an increasing bacterial count trend toward the end of study in the SPLENDA® (sucralose) group (GLM P>0.05; relative to centered log-transformed data for LB agar). FIGS. 8A-H illustrates other in-house agars, yeast extract agar, and SPLENDA® (sucralose) agar yielding similar trends, compared with LB agar. FIG. 3D, Total number of anaerobes (TSA), lactobacilli (MRS agar), and enterobacteria (LB) after 42 days of SPLENDA® (sucralose) supplementation in SAMP mice (unpaired t test, n=6/group). FIG. 3E, The total number of enterobacteria in the spleen suggests that SPLENDA® (sucralose) had no systemic bacteremic effect. FIG. 3F, Glucose tolerance test on day 40 with animals with SPLENDA® (sucralose) supplementation in experiment 2 (high FDA-approved dose). Notice the lack of significant effect across experimental mice. FIG. 3G, Glucose tolerance test curves illustrated as mean±SD. Univariate analysis across time points showed no differences due to SPLENDA® (sucralose). Abbreviation: AUC, area under the curve (n=6 mice/group).

Figure 4A:
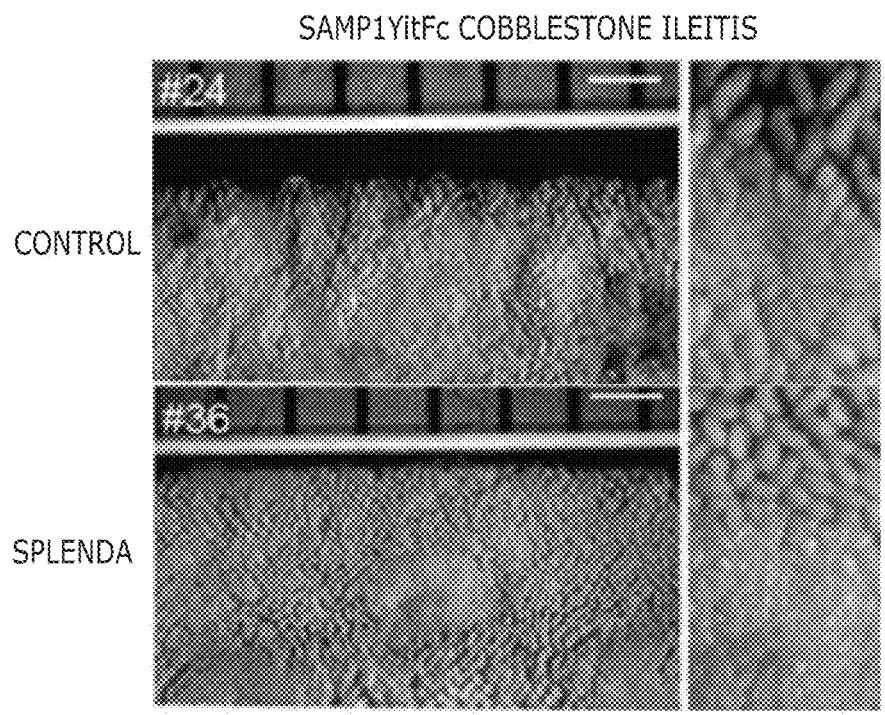
FIG. 4A, En face stereomicroscopic images of AKR and SAMP ileal mucosa after 47 days of supplementation of SPLENDA® (sucralose) at the maximum FDA-approved dose (experiment 2, medium dose, AKR vs SAMP mice, n=6/group, supplementation started at 25.2±2.4 weeks of age). Notice similar 3D stereoenterotype for SAMP cobblestone ileitis and the healthy mucosa in AKR mice.
Figure 4A:
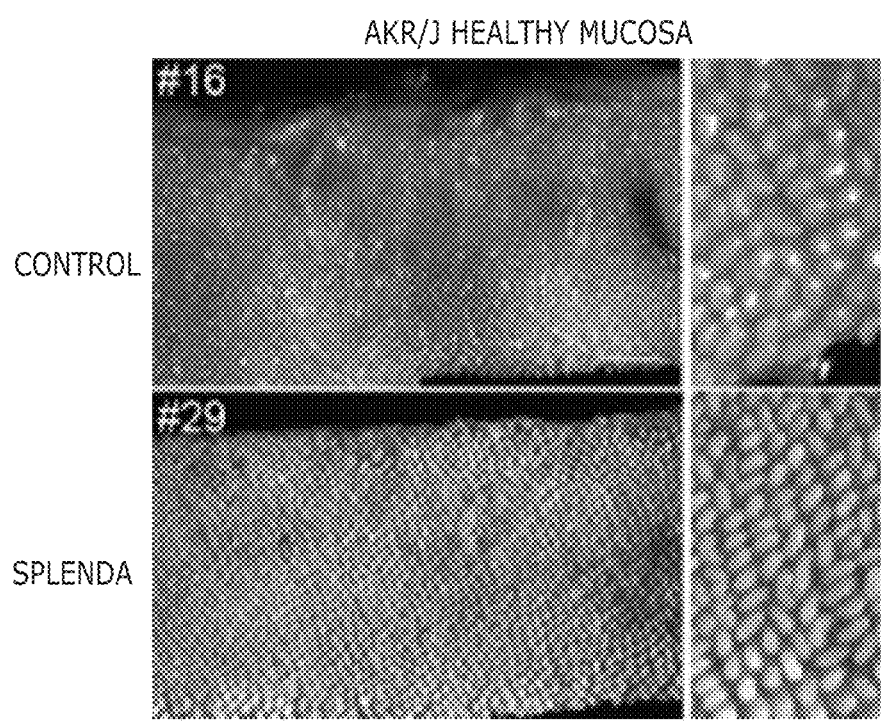
Figure 4B:
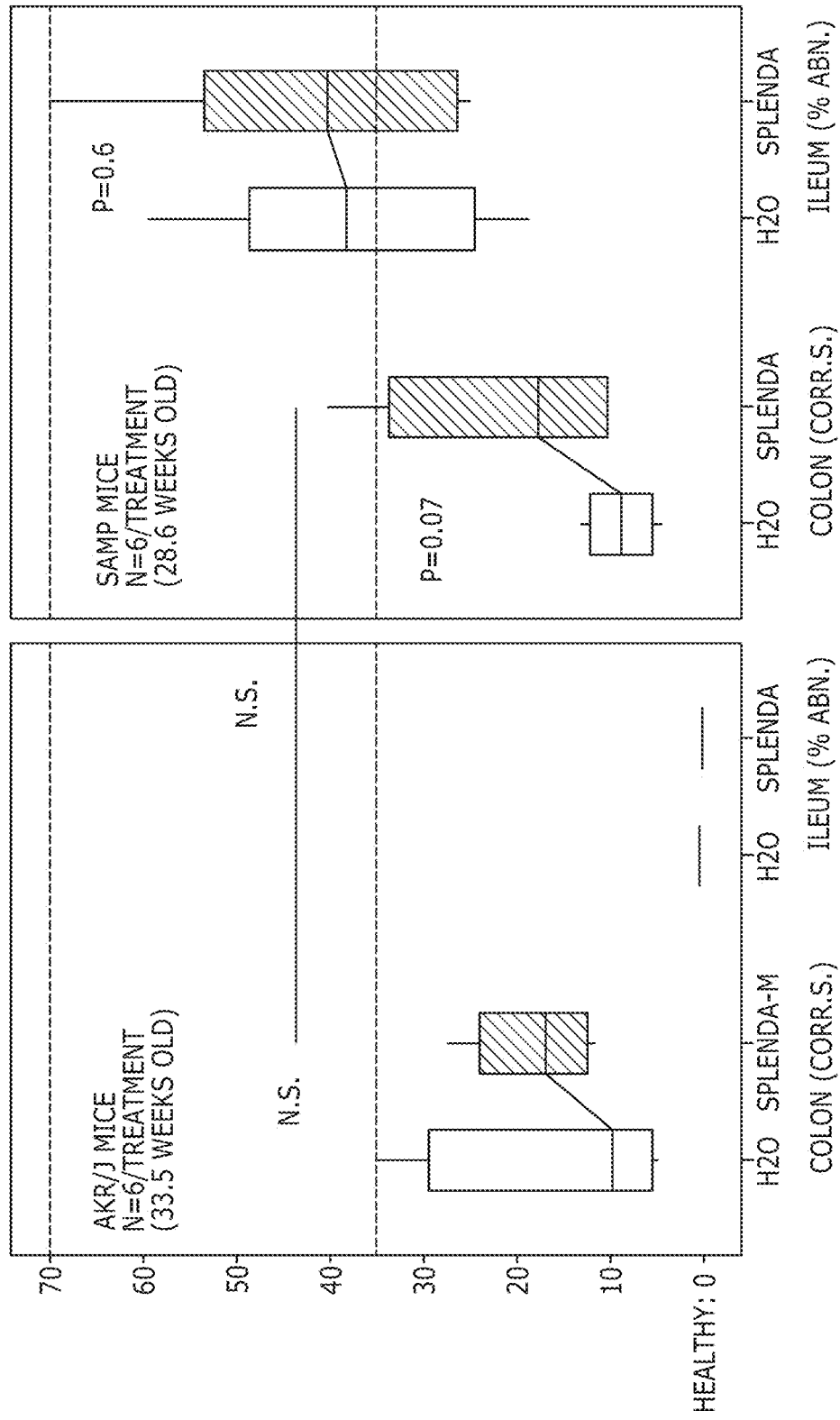
FIG. 4B, Cumulative 3D-SMAPgut scores on mucosal surface morphology for the colon (corrugation score/cm) and ileum (percentage of abnormal mucosa). Despite the positive trend (upward lines connecting means), there was no statistical difference between groups in all 3 SPLENDA® (sucralose) experiments, irrespective of dose.
Figure 4C:
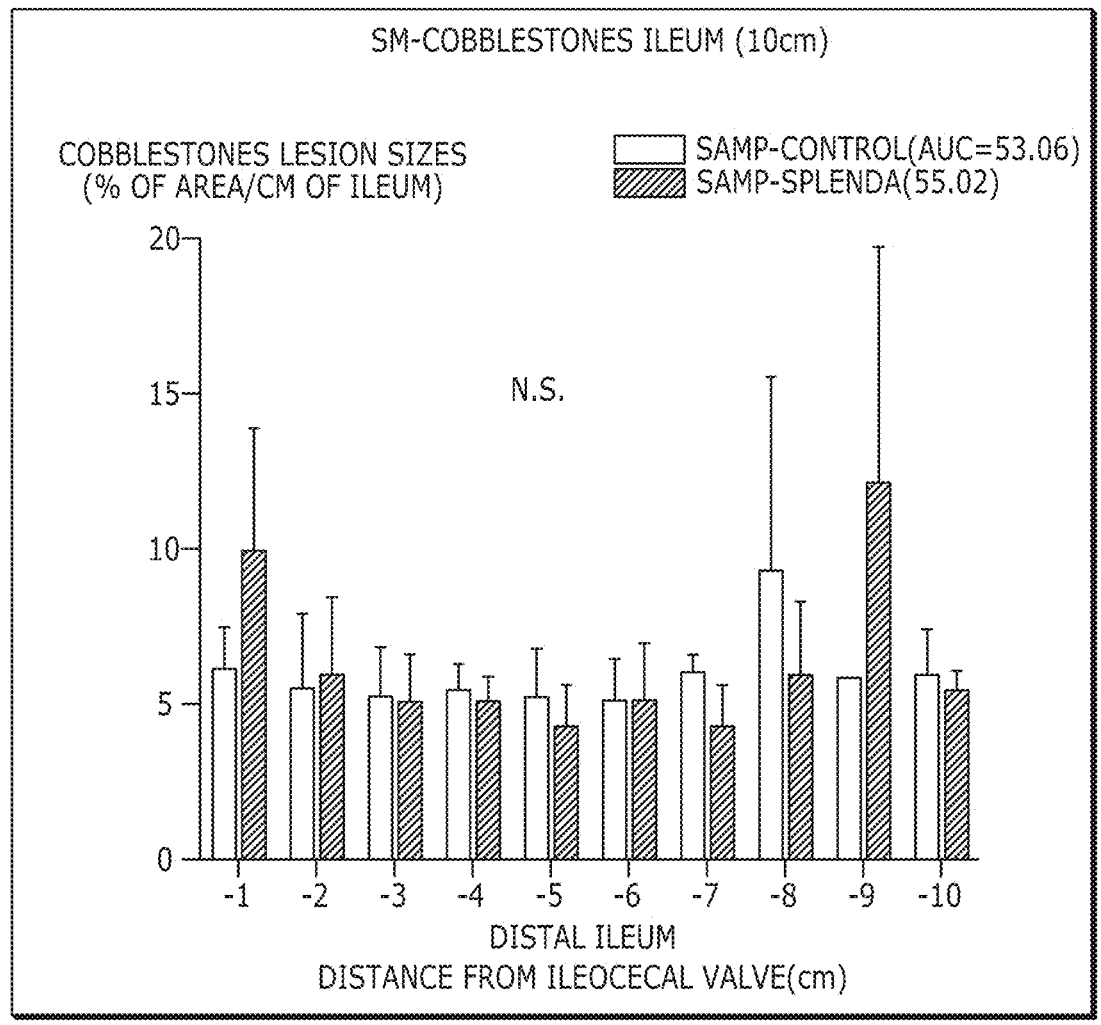
FIG. 4C, Average size for average cobblestone for each centimeter of the distal ileum.
Figure 4D:
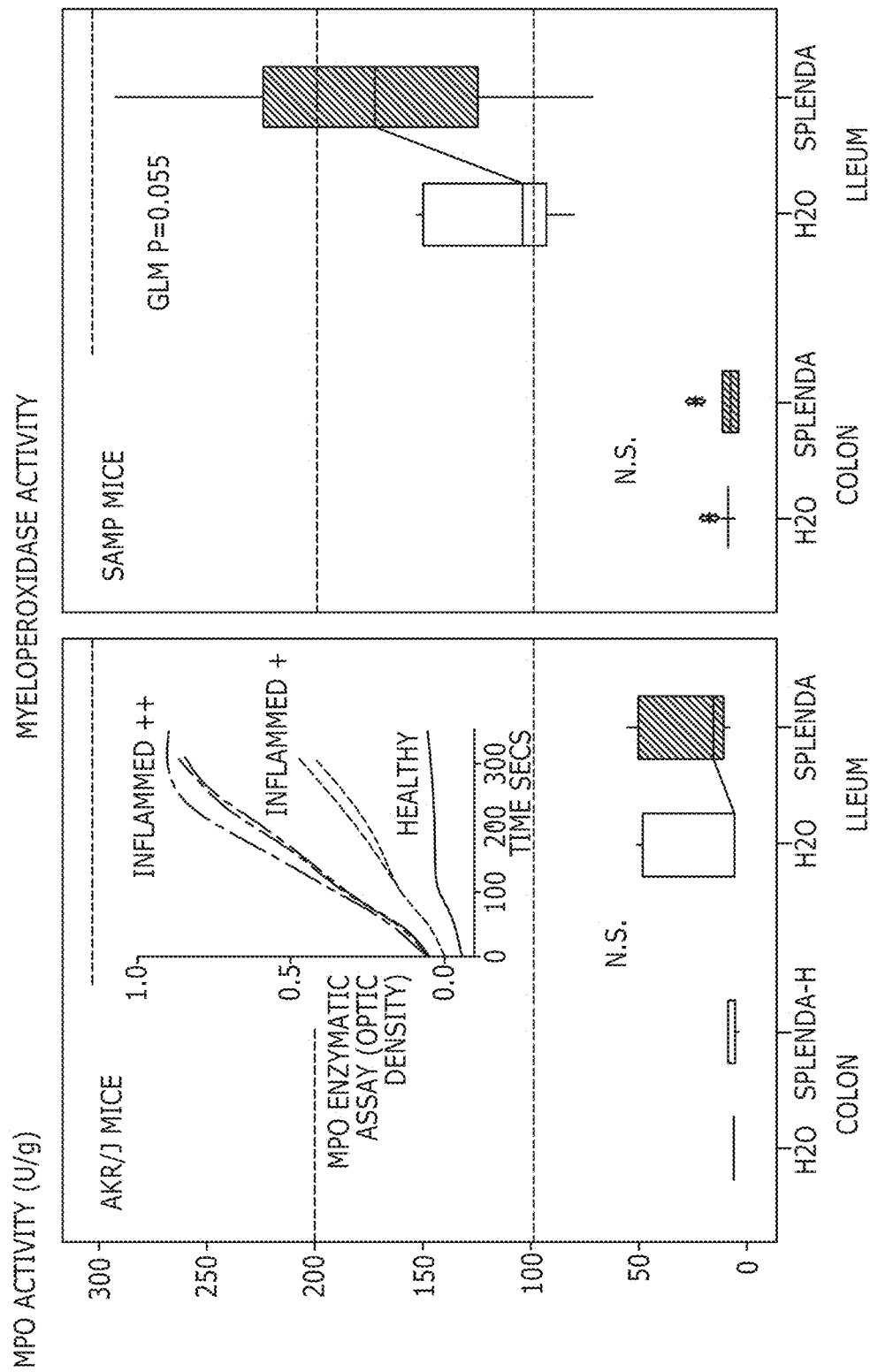
FIG. 4D, MPO activity from colon and ileum tissue at the end of the experiment. Notice that increased MPO occurred only in mice with ileitis. Inset: Example of MPO activity for 3 tissues with different MPO reactivities. Notice the reproducibility among triplicates in Table 1 (Summary of MPO activity in tissues of mice after supplementation with SPLENDA® (sucralose)).
Figure 4E:
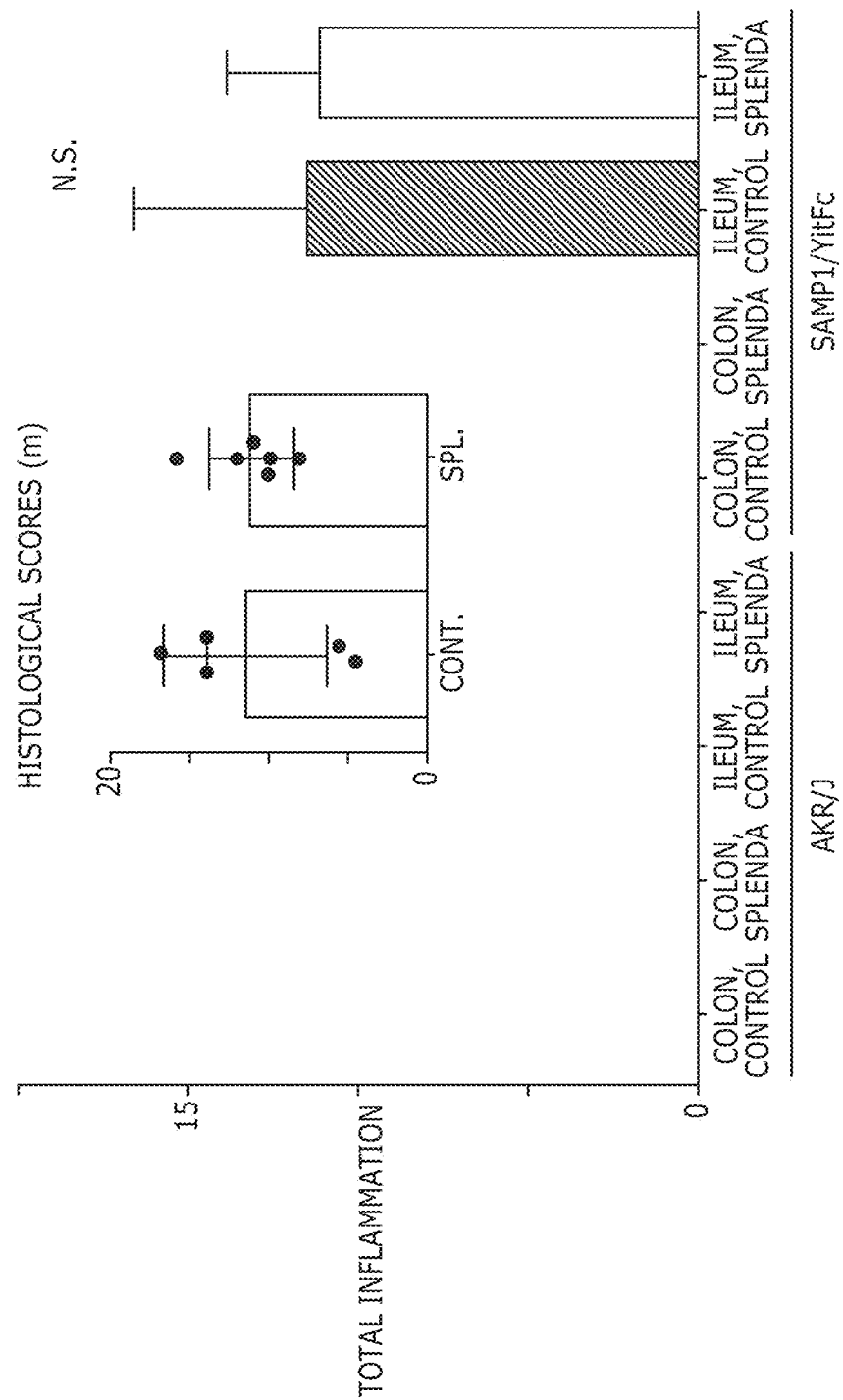

FIGS. 4A-E show SPLENDA® (sucralose) has no effect on 3D-SM or histological scores but promotes tissue FIG. 4E, Histological scores of the colon and ileum. Notice that there were no differences between groups.

Figure 5A:
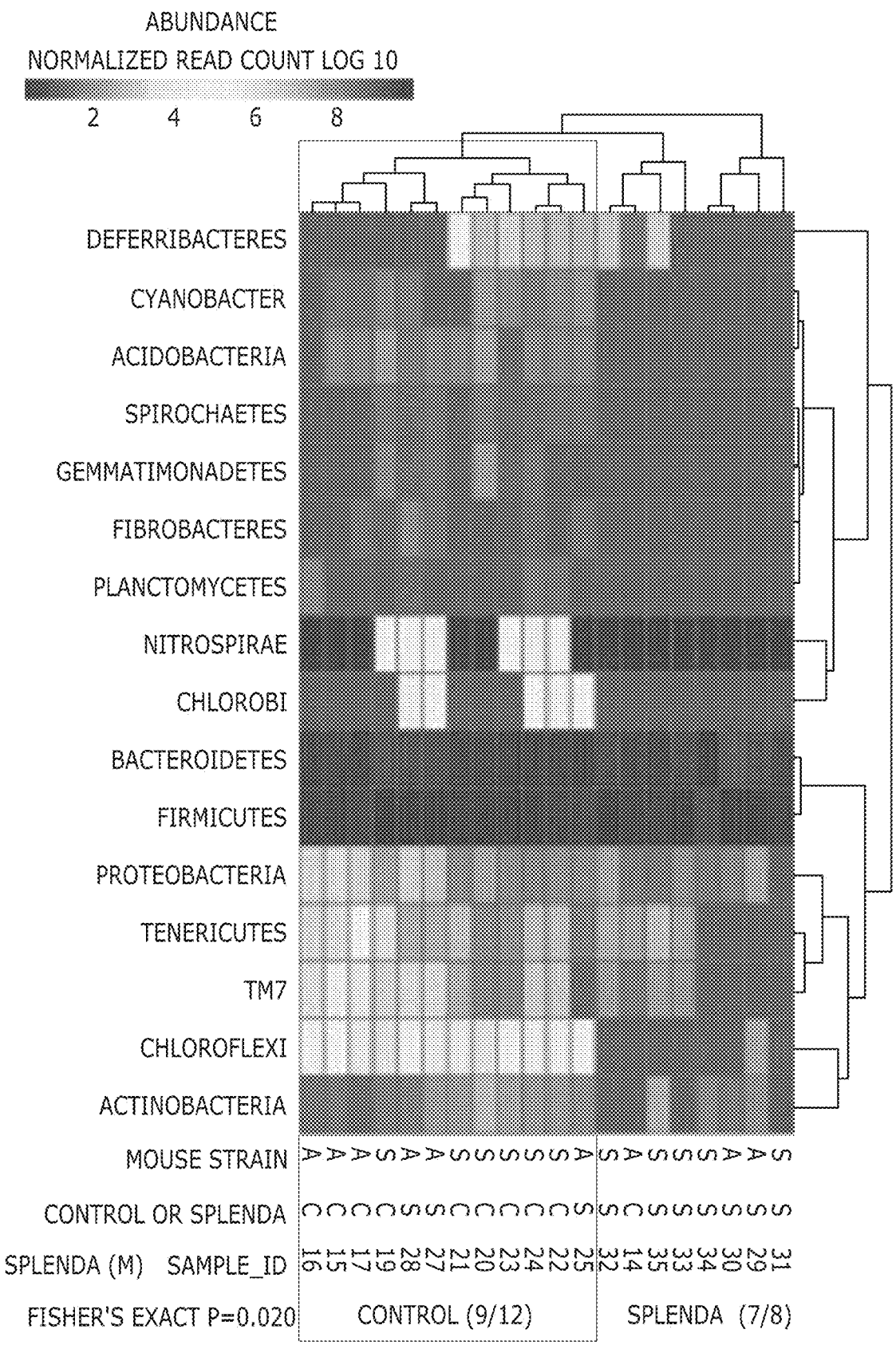
Figure 5B:
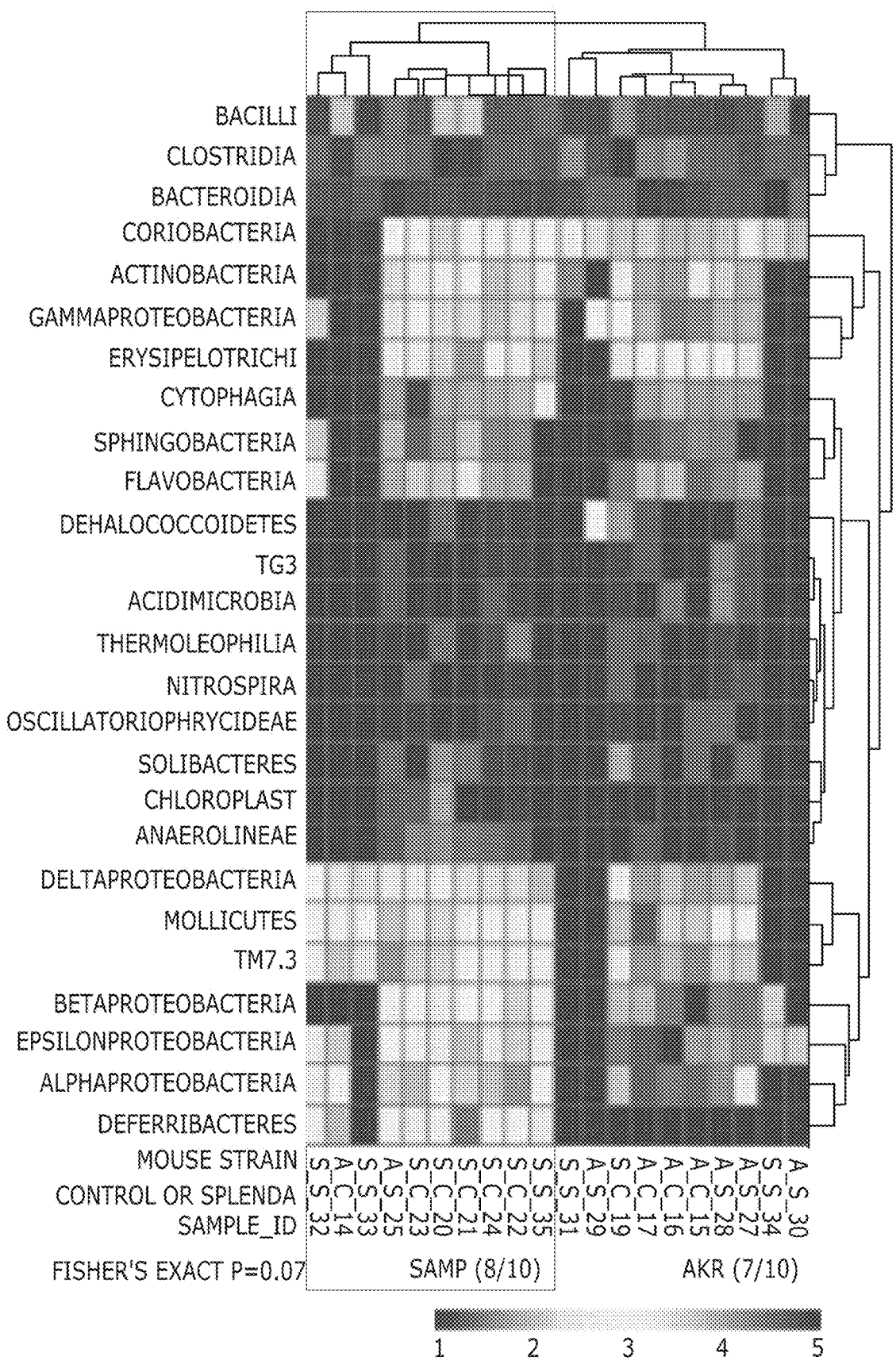
Figure 5C:
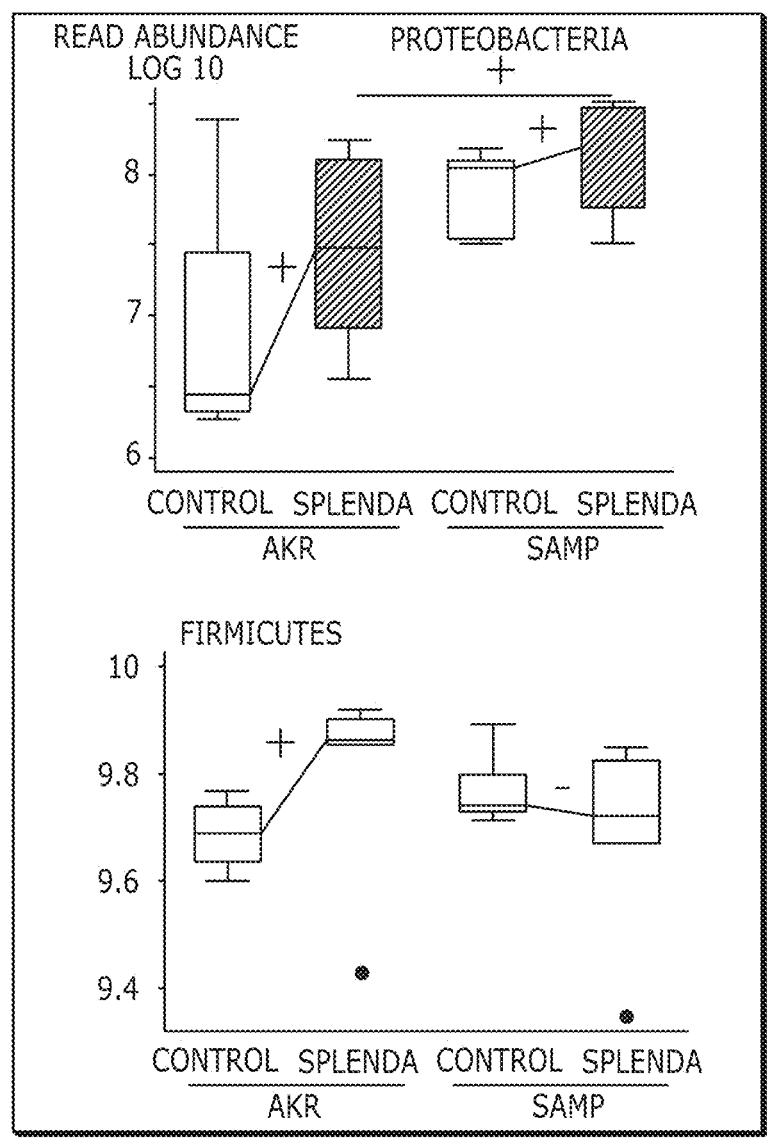
Figure 5D:
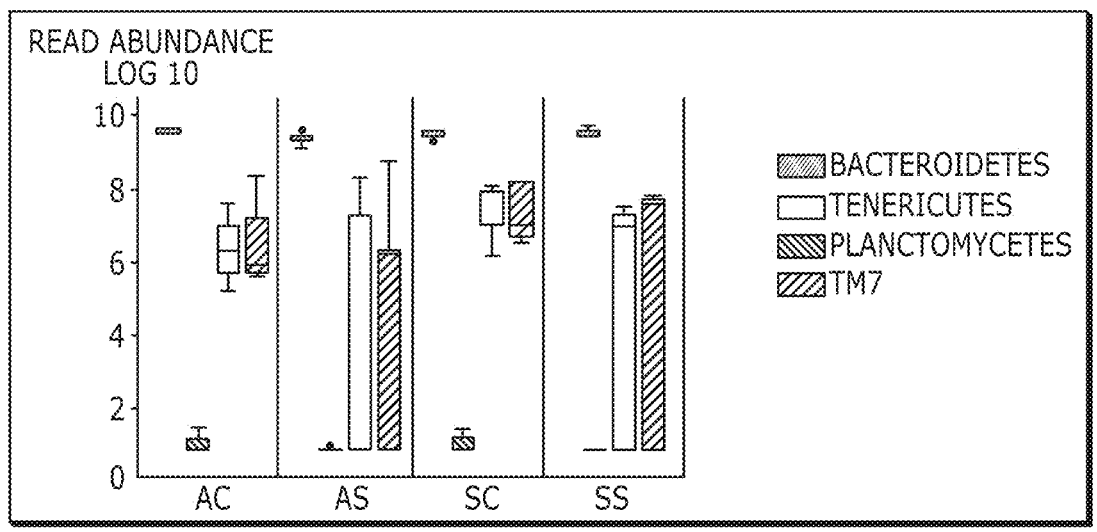
Figure 5E:
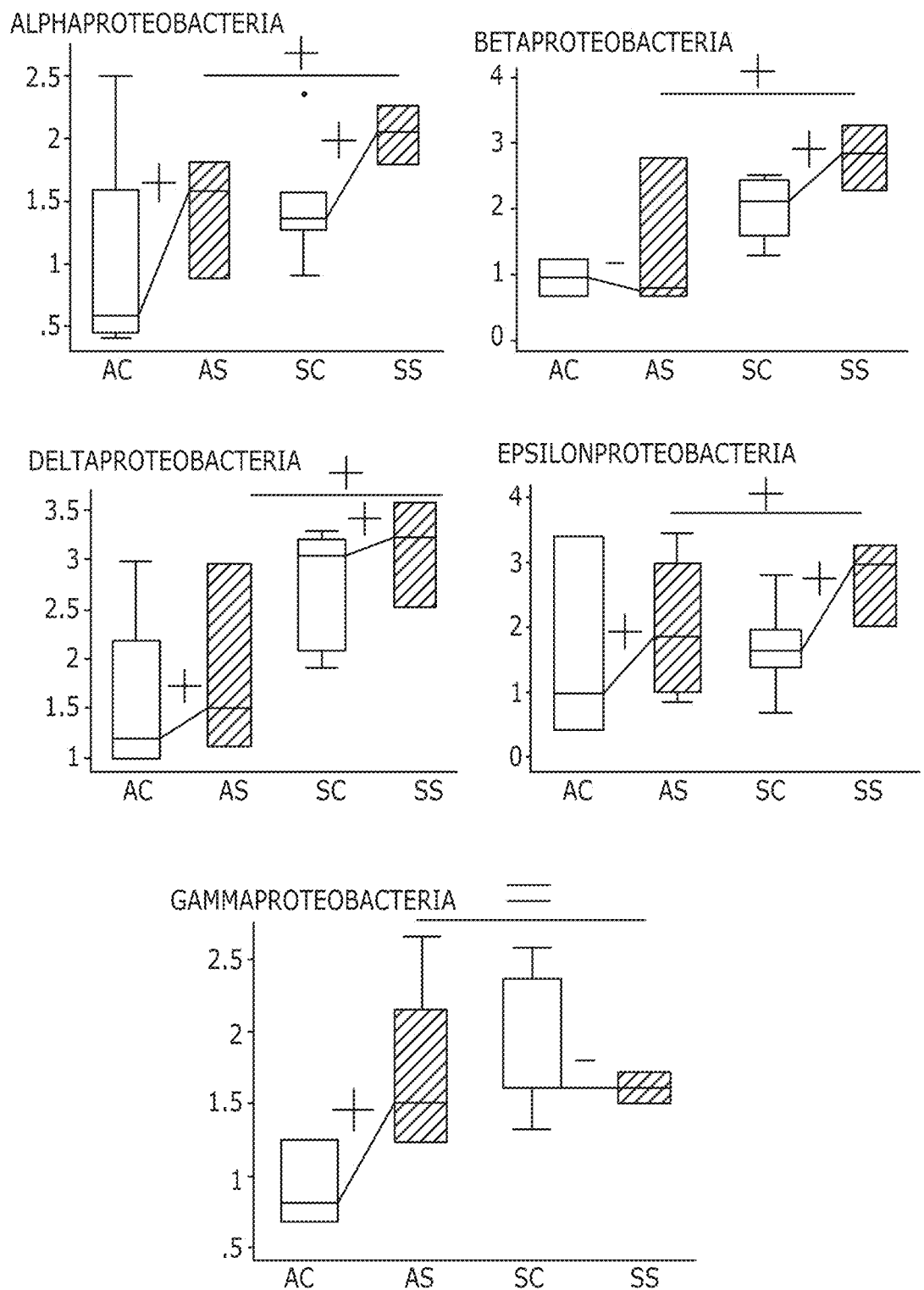

FIGS. 5A-E show SPLENDA® (sucralose) promotes gut dysbiosis characterized by enrichment of Proteobacteria in mice. FIG. 5A, Phylum analysis. 16S rRNA gene copy microbiome abundance normalized and presented as an unsupervised clustered hierarchical heat map that illustrates a significant effect attributable to SPLENDA® (sucralose) (increase in Proteobacteria and reduction of other phyla including Chloroflexi; P=0.02). Note the high relative abundance of Bacteroidetes with respect to Firmicutes. Notice that when present several proteobacterial classes contribute to microbiome separation between SAMP and AKR (P=0.07). Notice highly abundant Bacteroidia, Bacilli, and Clostridia cluster at the top of the panel. FIG. 5C, Boxplot illustrates the effect of SPLENDA® (sucralose) on phylum Proteobacteria, compared with Firmicutes. Lines connecting normalized averages indicate positive trends. FIG. 5D, Boxplot illustrates high Bacteroidetes abundance and the comparative reduction of other phyla in SPLENDA® (sucralose)-treated mice. FIG. 5E, Bacterial abundance across all 5 Proteobacteria classes detected in the study. Sign binomial statistics of means in $\log_{10}$ scale suggests that SPLENDA® (sucralose) promotes a positive effect (including (C); 10/12 were positive, 2/12 were negative, 1-tail sign P=0.019). Abbreviations, C, control water; diet S, SPLENDA® (sucralose); mouse A, AKR/J; S, SAMP. B, Class analysis.

Figure 6A:
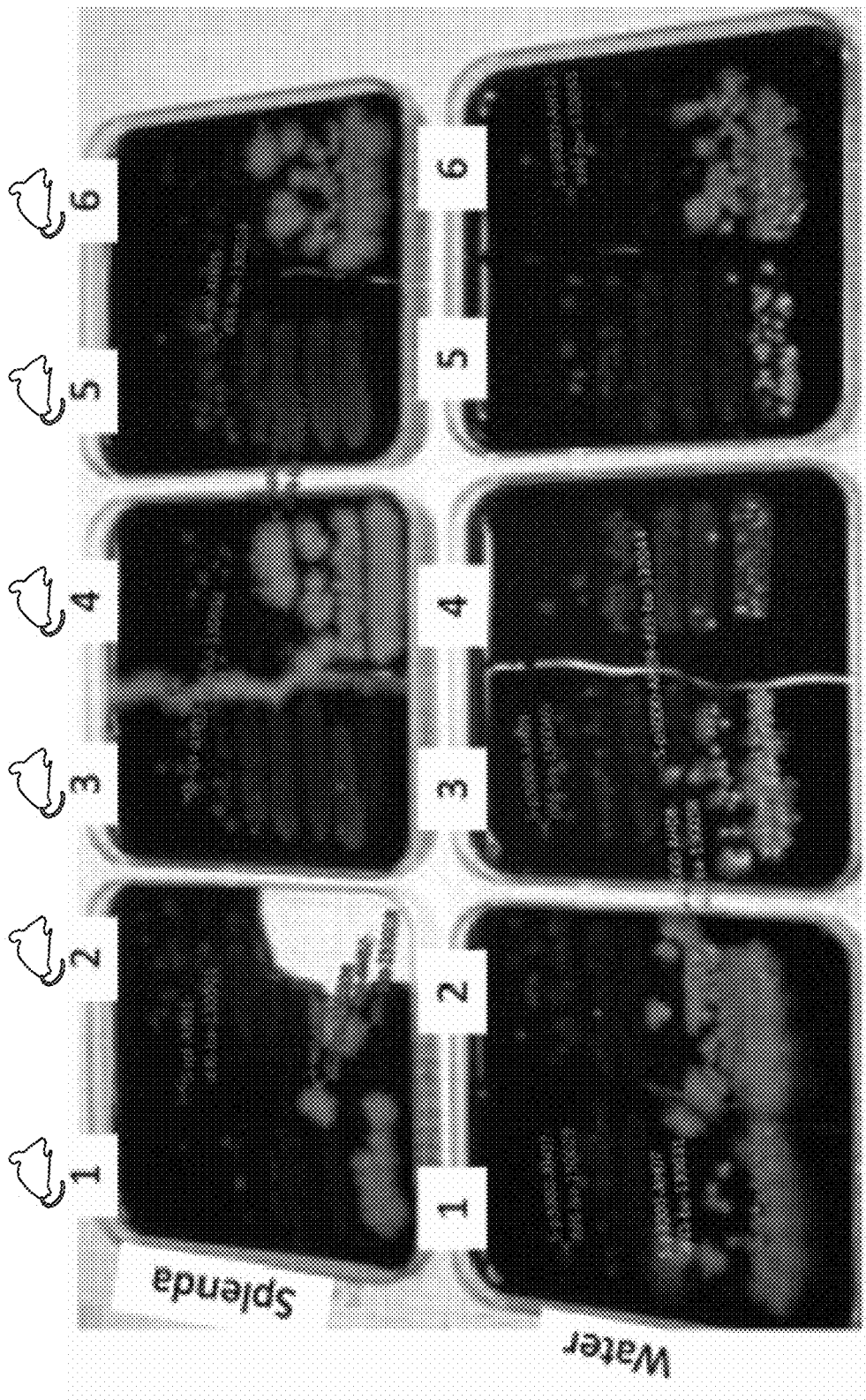
Figure 6B:
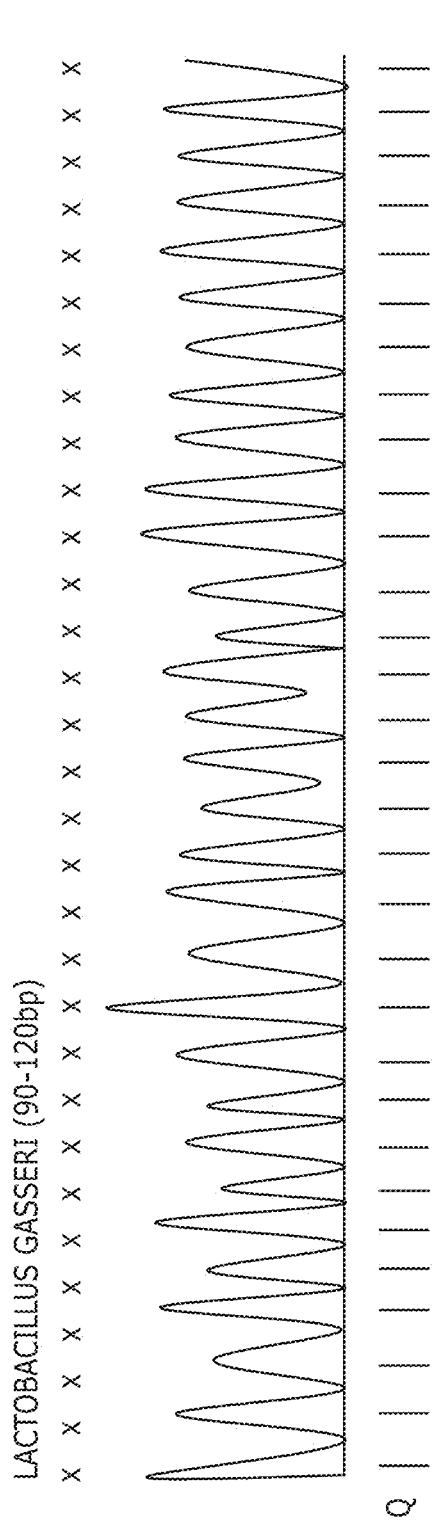
Figure 6B:
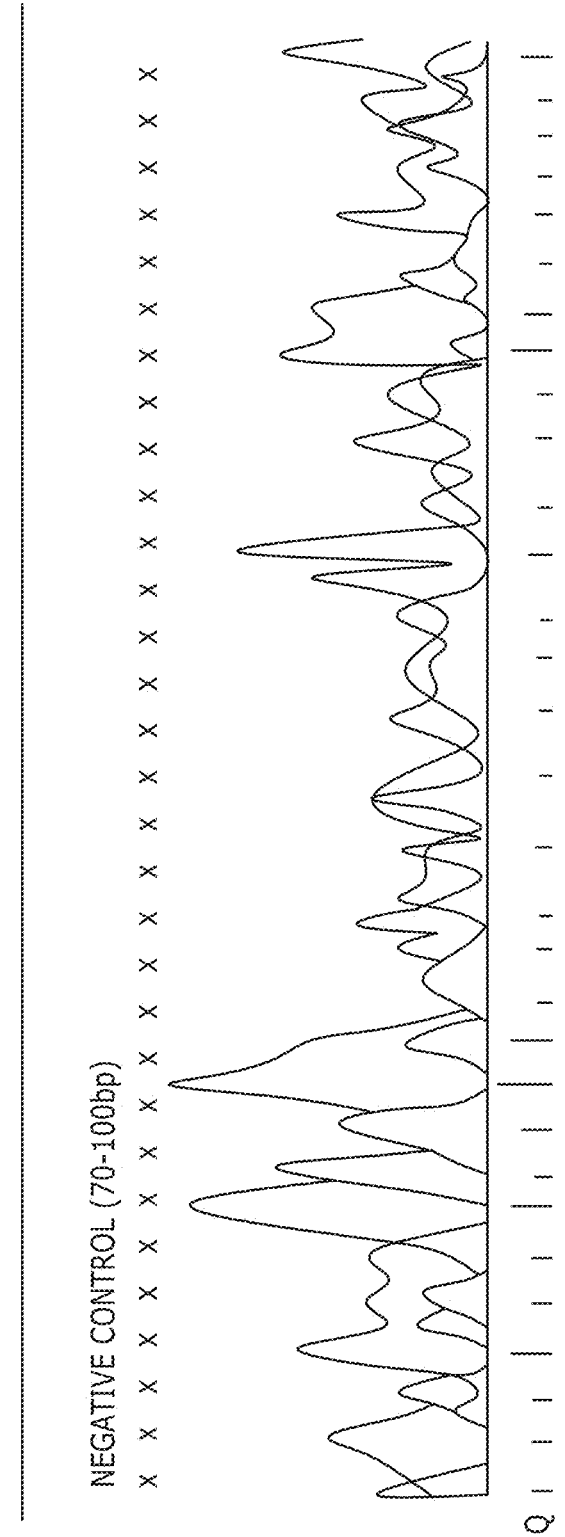
Figure 6C:
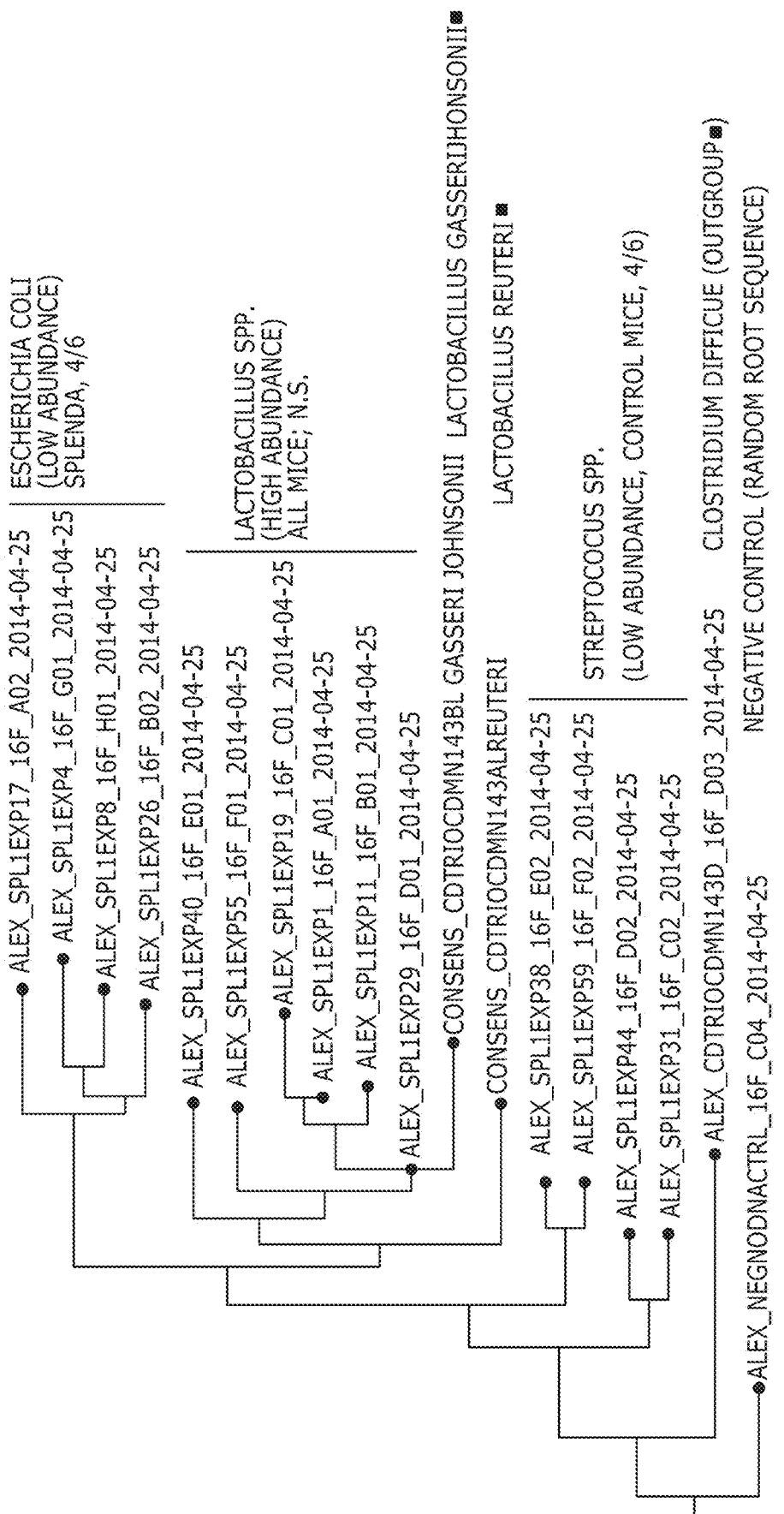
Figures 6D, 6E:
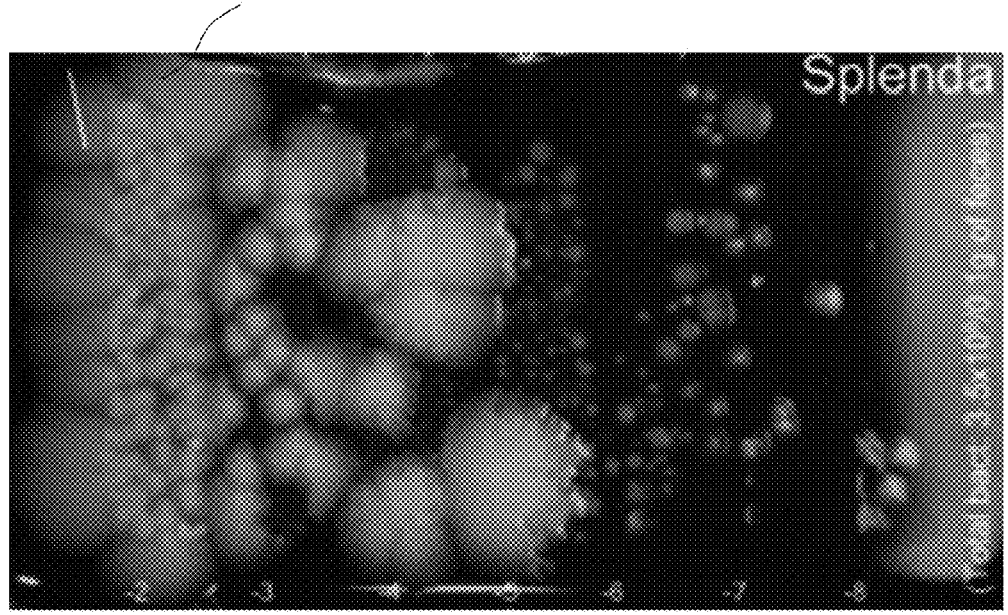

FIGS. 6A-E show SPLENDA® (sucralose) promotes the replacement of *Streptococcus* spp. with *E. coli* in the intestinal tract of SAMP mice. FIG. 6A, "Parallel Lanes Plating" Method. Photograph of BHI agar plates supplemented with 5% sheep defibrinated blood inoculated with 10-fold serial dilutions of feces from SAMP mice using a parallel mini-drop slide and lanes method developed for tracking and relative enumeration of complex bacterial communities (FIGS. 8A-H). Mice were caged individually and exposed to a composite of bedding and feces (IsPreFeH) prior to receiving SPLENDA® (sucralose) at a low dose (1.5 mg/mL) or water for 42 days. Representative colonies comprising all possible morphologies in each agar plate were selected for purification and Sanger sequencing for speciation (from high dilutions, green labels; and low dilutions, pink or red labels). Notice the colony morphology (large, thick, spreading) of 4/6 mice in the SPLENDA® (sucralose) group is different from that of 4/6 control mice (whitish, smaller). FIG. 6B, Sanger sequence chromatograph. Single-colony PCR revealed *Lactobacillus gasseri* (umbonate, brown) as the most common abundant bacteria in mice, unaffected by SPLENDA® (sucralose) supplementation (see the panels below). Q, quality of consensus sequence. FIG. 6C, Phylogenetic analysis of 16S rRNA paired-end consensus sequences revealed that the whitish colonies in the control (water) group were closely related to *Streptococcus* spp., while bacteria in SPLENDA® (sucralose) mice were *E. coli*. FIGS. 6D and 6E, Close-up of colony morphologies on BHI agar after 5 days of aerobic incubation. Notice the "parallel lanes method" of 2 mice representing the SPLENDA® (sucralose) and control groups. Negative numbers indicate 10-fold dilution factor.

Figure 7A:
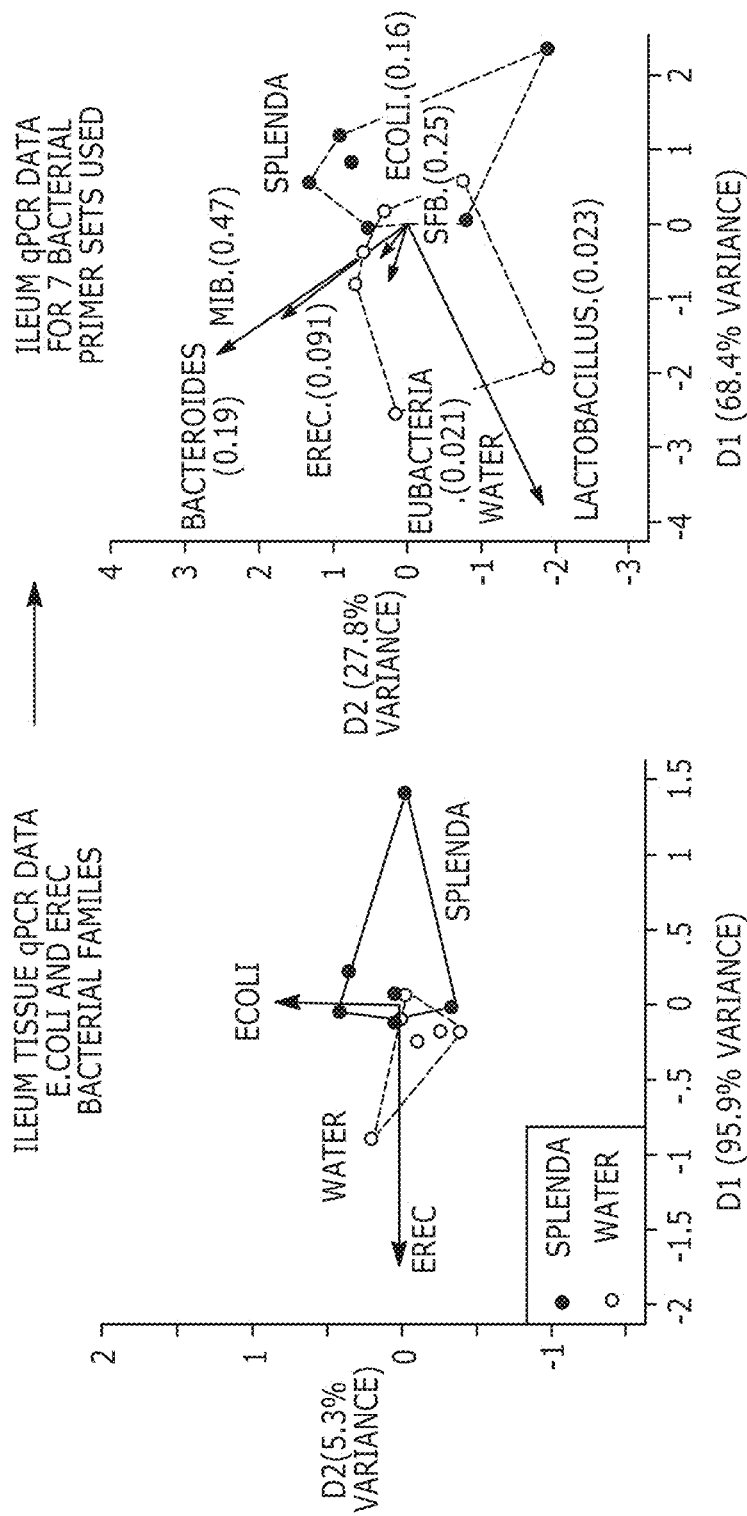
Figure 7B:
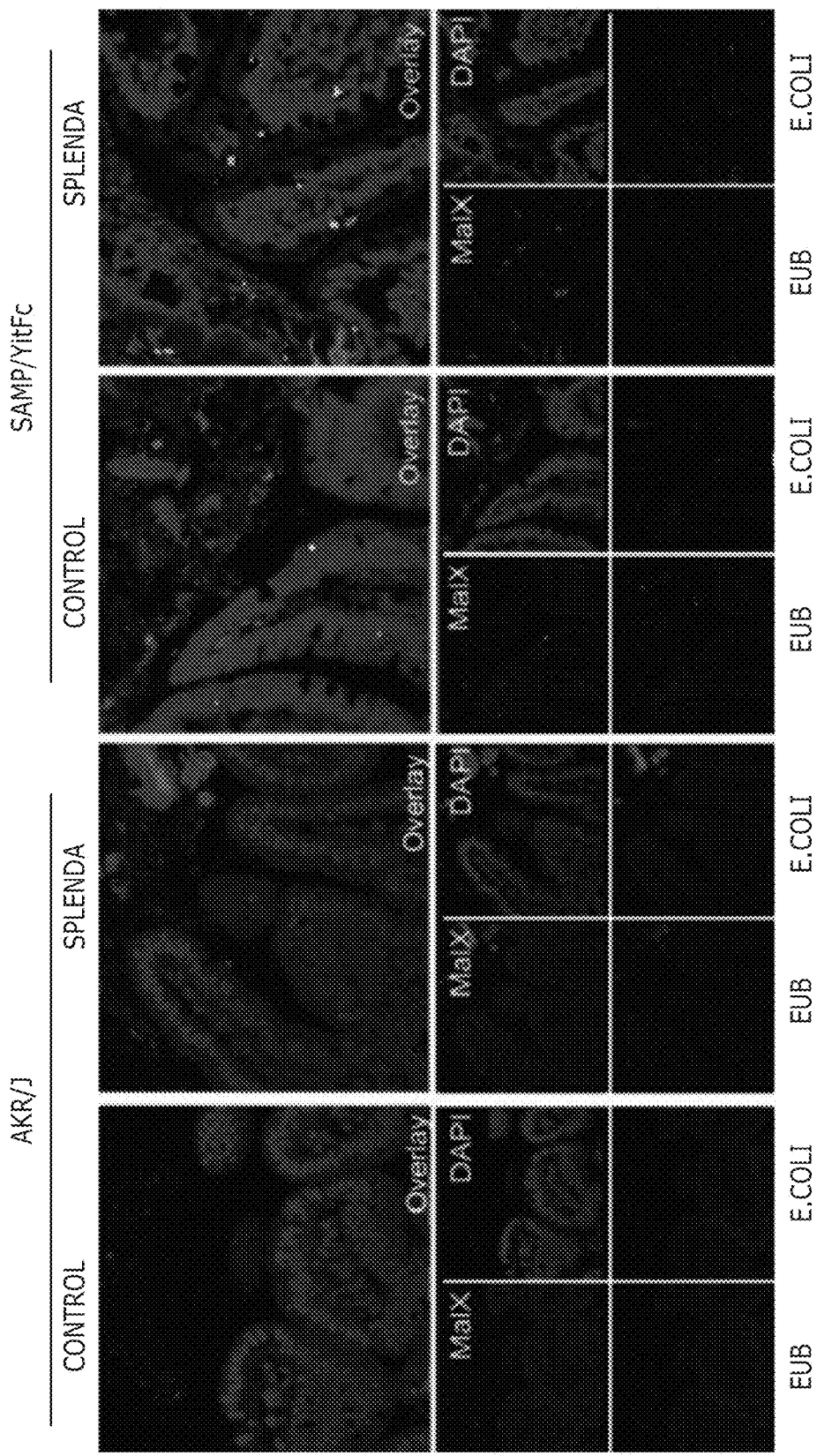
Figure 7C:
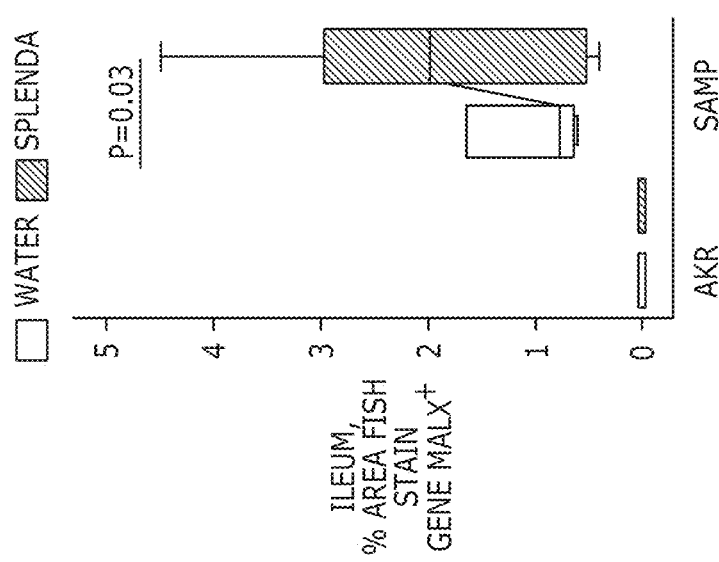

FIGS. 7A-C show bacterial qPCR and FISH staining of ileal tissue illustrates distinct microbiota and increased invasive malX+bacteria (*E. coli*) in SPLENDA® (sucralose)-supplemented SAMP but not AKR mice. FIG. 7A, Multivariate analysis of DNA qPCR data from ileum tissues of SAMP mice after 42 days of supplementation. Notice the display of mice (points) and the vector influence of the variables (arrows) on the overall matrix data variability (D1 and D2) for the *E. coli* and Erec primers, and for all the 7 primer sets used in this study. Hotelling's T-test P values are in parentheses. Notice the separation of the 2 clusters (water, SPLENDA® (sucralose)). FIG. 7B, Ileal sections from SAMP mice supplemented with 3.5% SPLENDA® (sucralose) for 42 days (SPLENDA® (sucralose)) or nontreated control mice (Water) were hybridized with probes to Eubacteria (purple), *E. coli* (red), and malX (maldodextrin, green), a component of the maltose/maltodextrin metabolism system. Cell nuclei are visualized with DAPI (blue). Images shown are representative of analyses performed in 5 mice per group. Notice the presence of *E. coli* in both the epithelial layer and the subepithelial lamina propria tissue (villi), and the large bacterial clusters in the lamina propria of SAMP mice on the SPLENDA® (sucralose) panels. FIG. 7C, Percentage of area that stained positive for the malX gene probe (pixels, malX+area/total tissue area*100). Unpaired t test statistics. A minimum of 4 fields were analyzed/sampled using ImageProPlus v7 software (AKR control, n=4; AKR SPLENDA® (sucralose), n=6; SAMP control, n=6; SAMP SPLENDA® (sucralose), n=10).

Figure 8A:
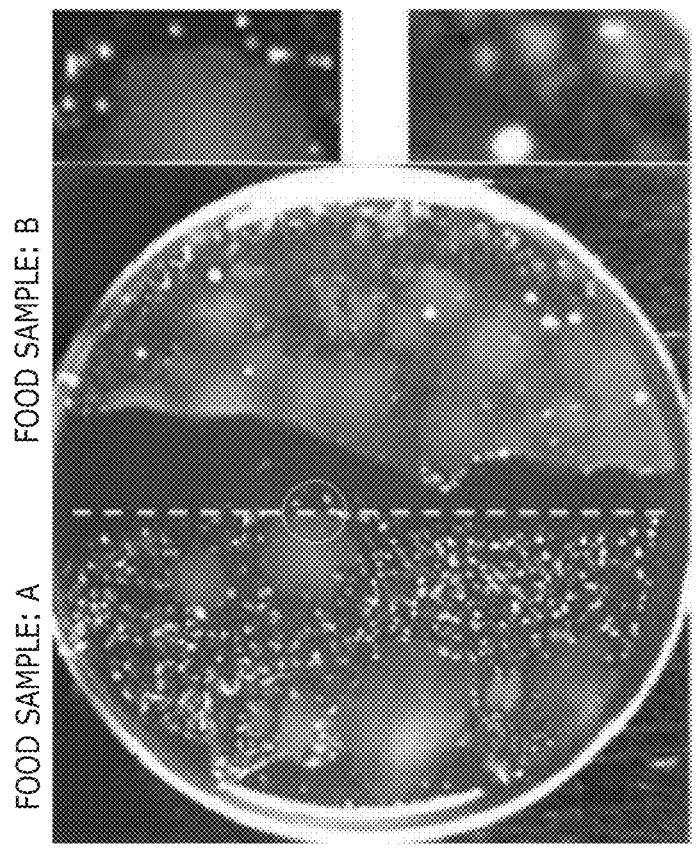
Figure 8B:
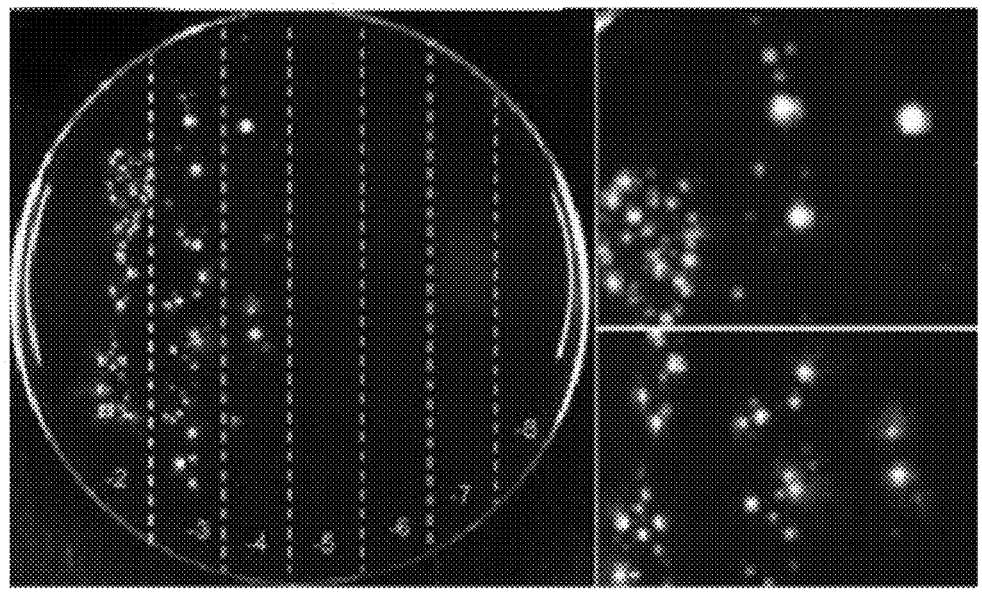
Figure 8C:
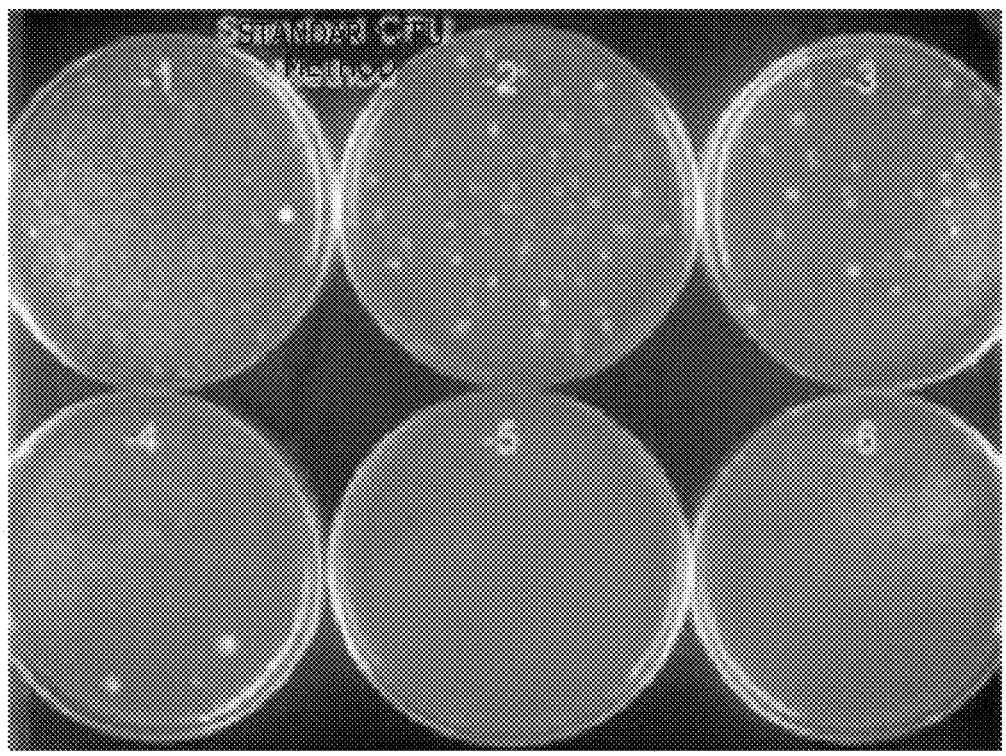
Figure 8D:
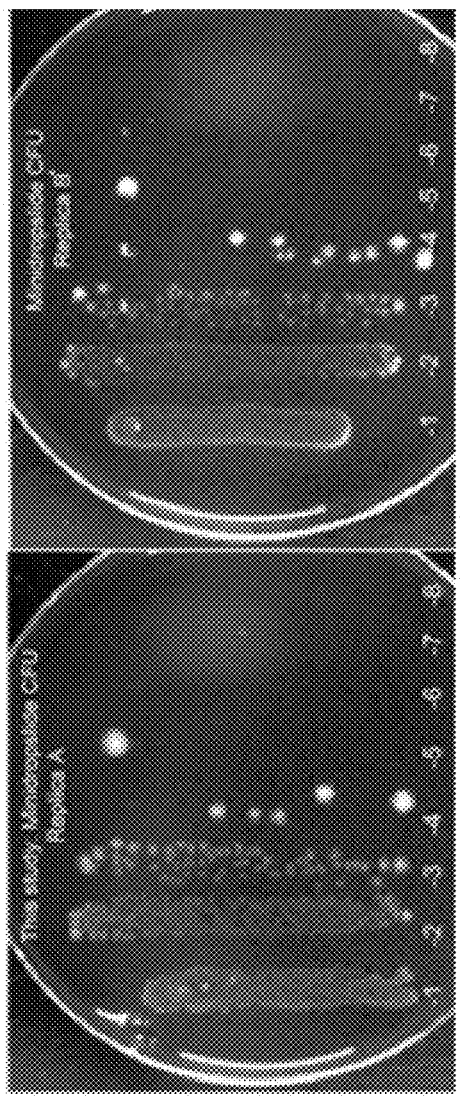
Figure 8E:
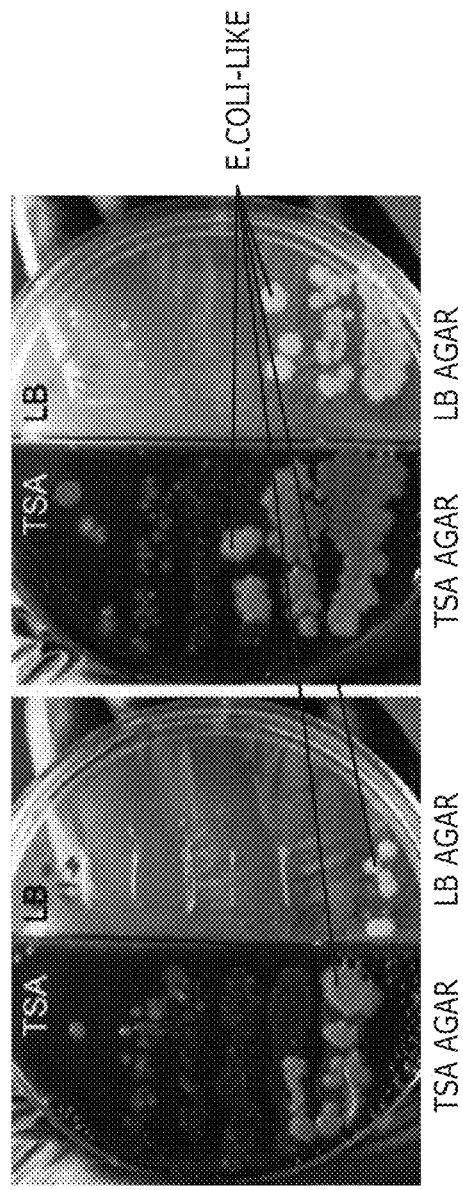
Figure 8F:
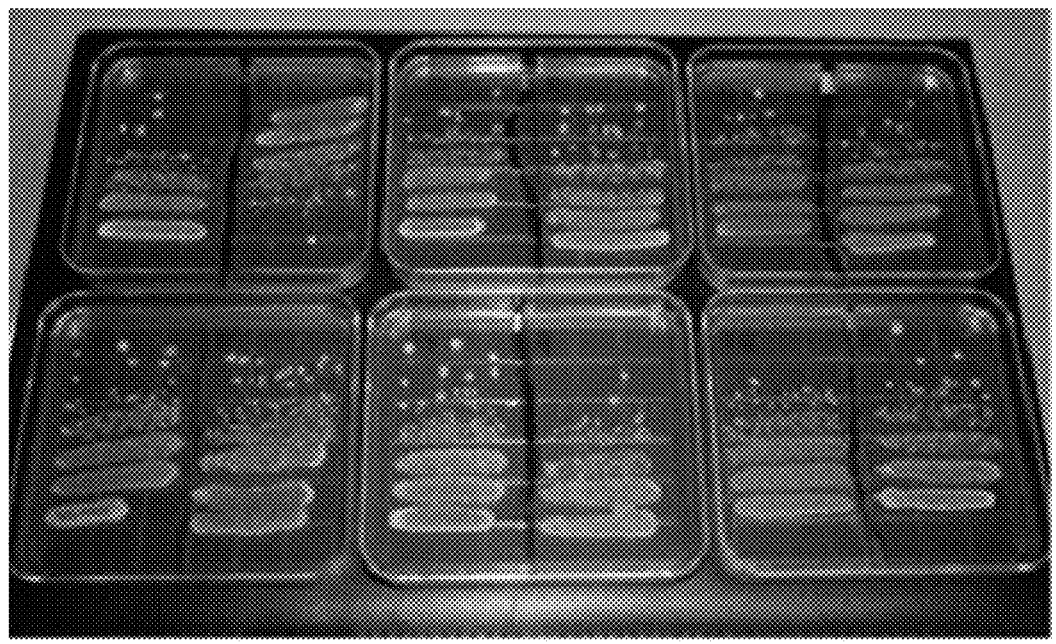
Figure 8G:
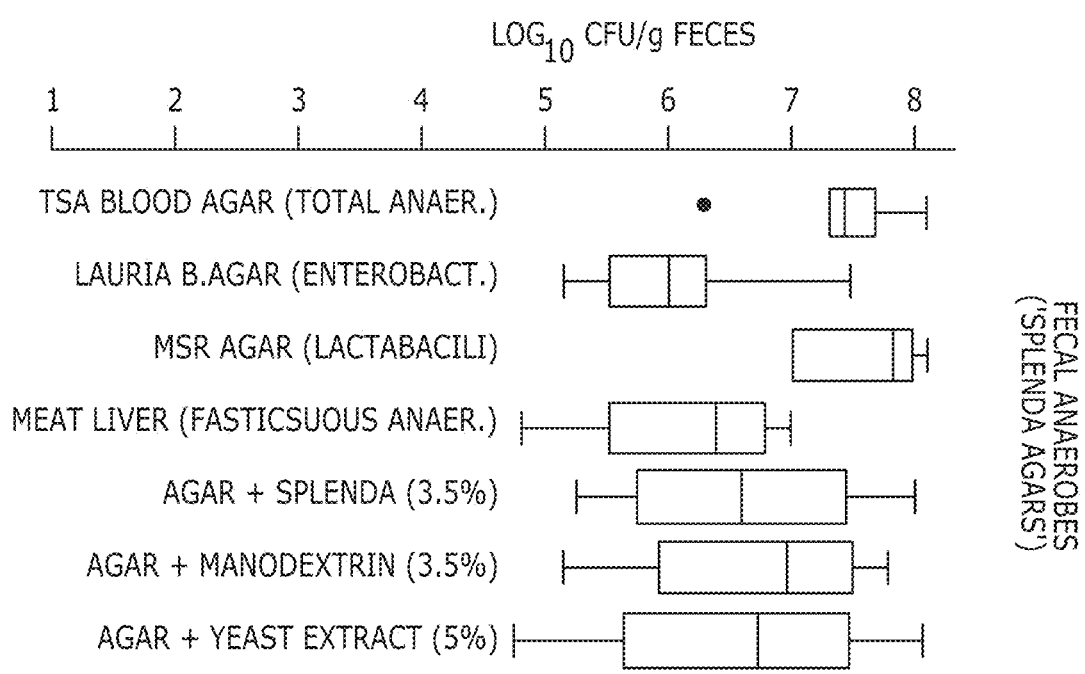
Figure 8H:
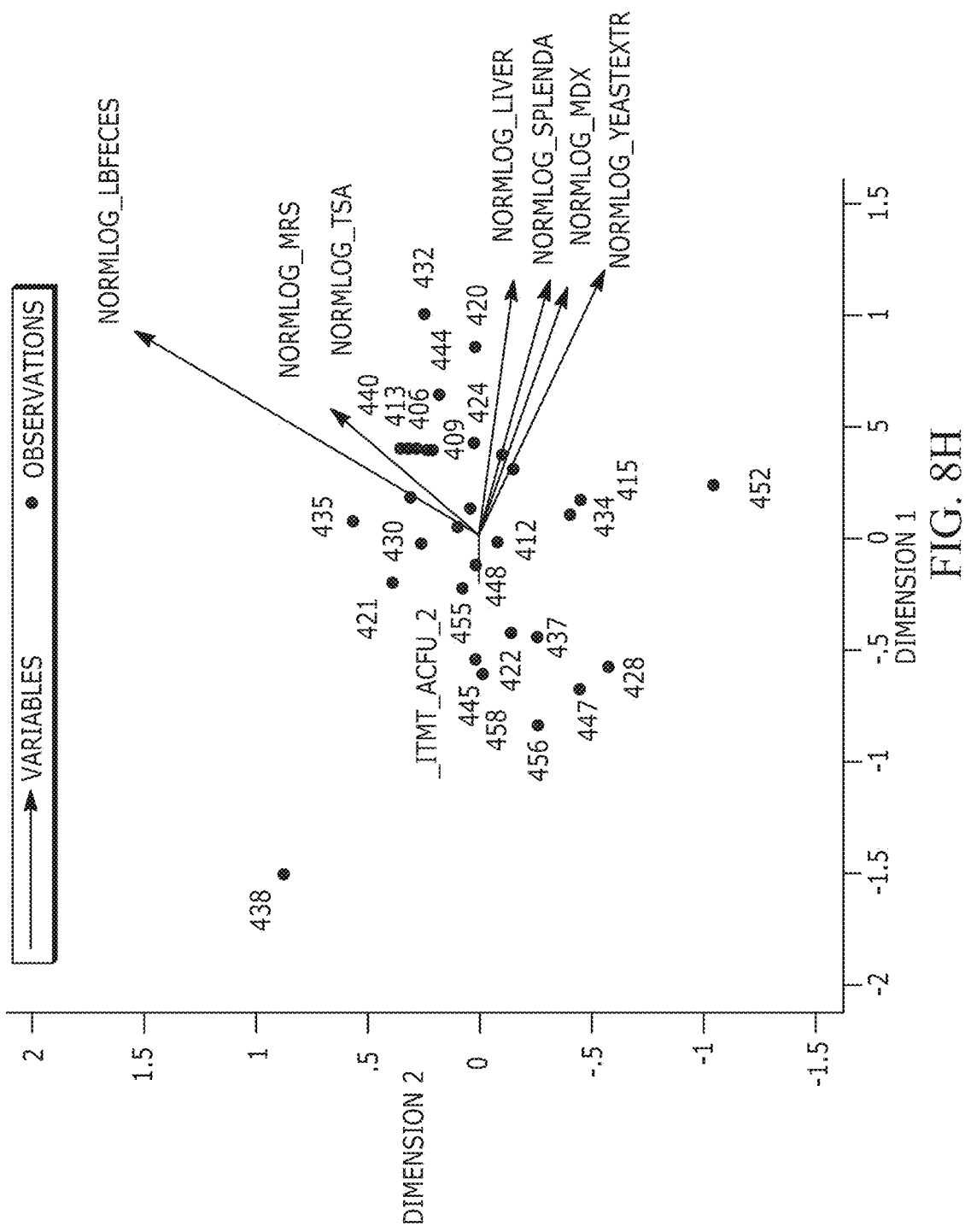

FIGS. 8A-H show development of a "Parallel Lanes Platting" method for relative enumeration of bacteria in complex communities. FIG. 8A, Two food samples (retail ground meat) on TSA illustrate diverse bacterial colonies at different concentrations in a relatively simple community (100 μL/half plate). FIG. 8B, "Parallel mini-drop lanes platting" of *Clostridium difficile* monocultures (10-20 μL/lane) illustrates that several solutions can be incubated on a single agar plate and quantified based on colony morphology. TSA and UV transilluminator. Multichannel pipettes allow the transfer of 8 dilutions on a single media plate. FIG. 8C, Standard plating methods use 100 μL/plate, making it agar intensive and difficult to track as the number of plates increase. FIG. 8D, The parallel mini-drop lanes platting method is highly reproducible. FIG. 8E, Herein, we illustrate the use of the method on fecal samples from two cohoused mice in TSA and LB agars. Notice that SAMP has more *E. coli* bacteria relative to the total number of bacteria. FIG. 8F, The same approach in square plates was used for SPLENDA® (sucralose) experiments to increase ability to select single colonies for PCR. MRS agar (lactobacilli). FIG. 8G, "Parallel Lanes Platting" of fecal samples using in house agars ('maltodextrin and SPLENDA® (sucralose) agars'). FIG. 8H, Multivariable analysis revealed that several agars yielded similar bacterial counts to assess the effect of SPLENDA® (sucralose) on SAMP mice. Meat liver base agar enables the quantification of strict and fastidious anaerobes, while allows (e.g., some *Clostridium* spp.) sulfite reducers to produce hydrogen sulfide ($H_2S$), which allows the blackening of colonies due to presence of ferric ammonium citrate.

Figure 9:
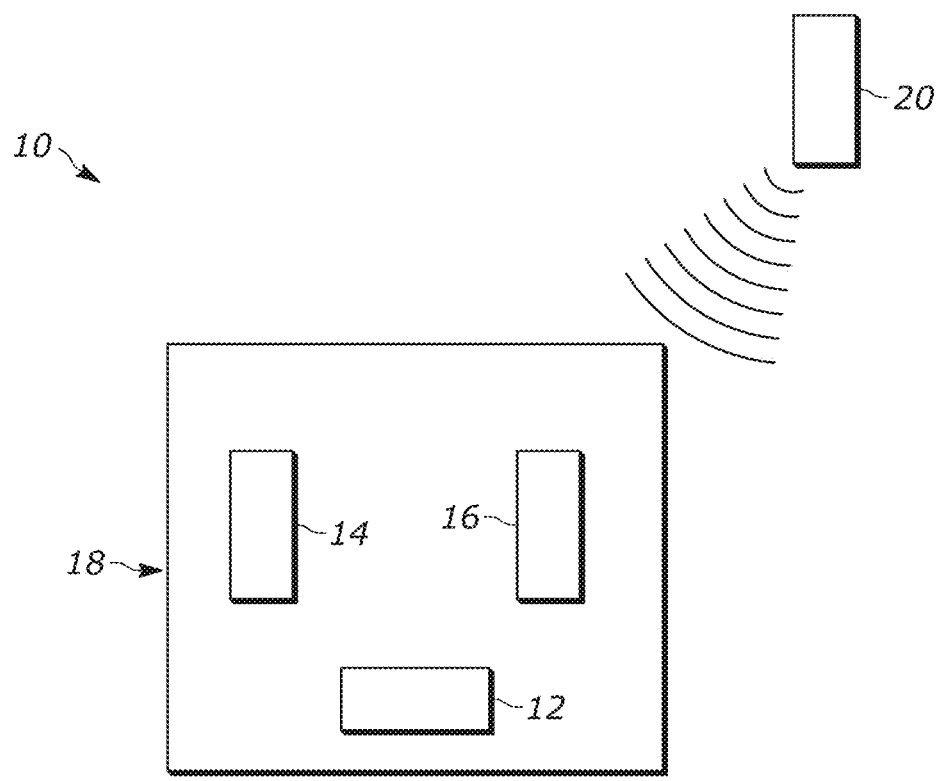

FIG. 9 is a schematic illustration of a kit for reducing or alleviating inflammation in the digestive tract of a subject in need thereof that consumes a non-caloric artificial sweetener according to one aspect of the present application.

Figure 10A:
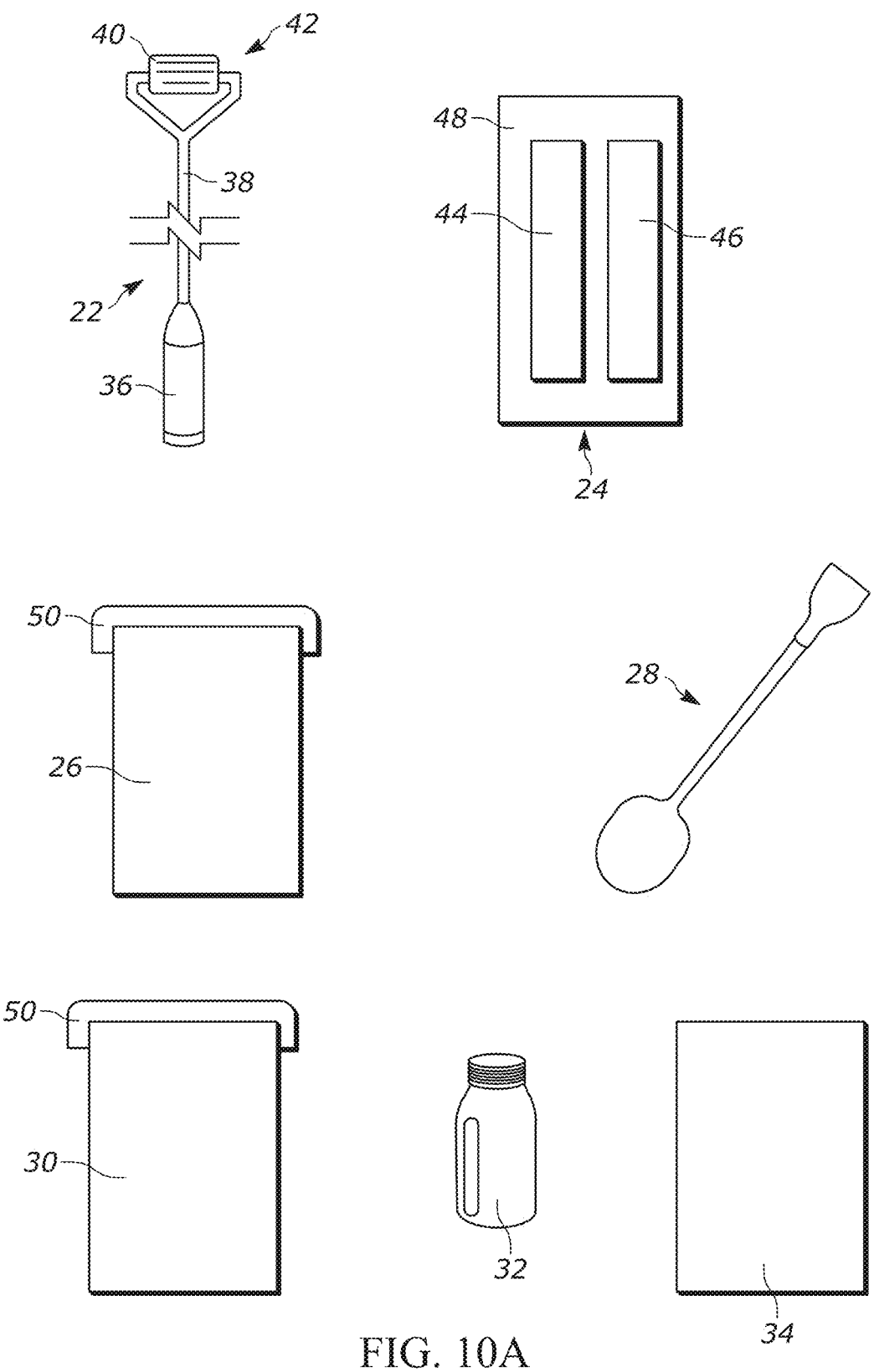
Figure 10B:
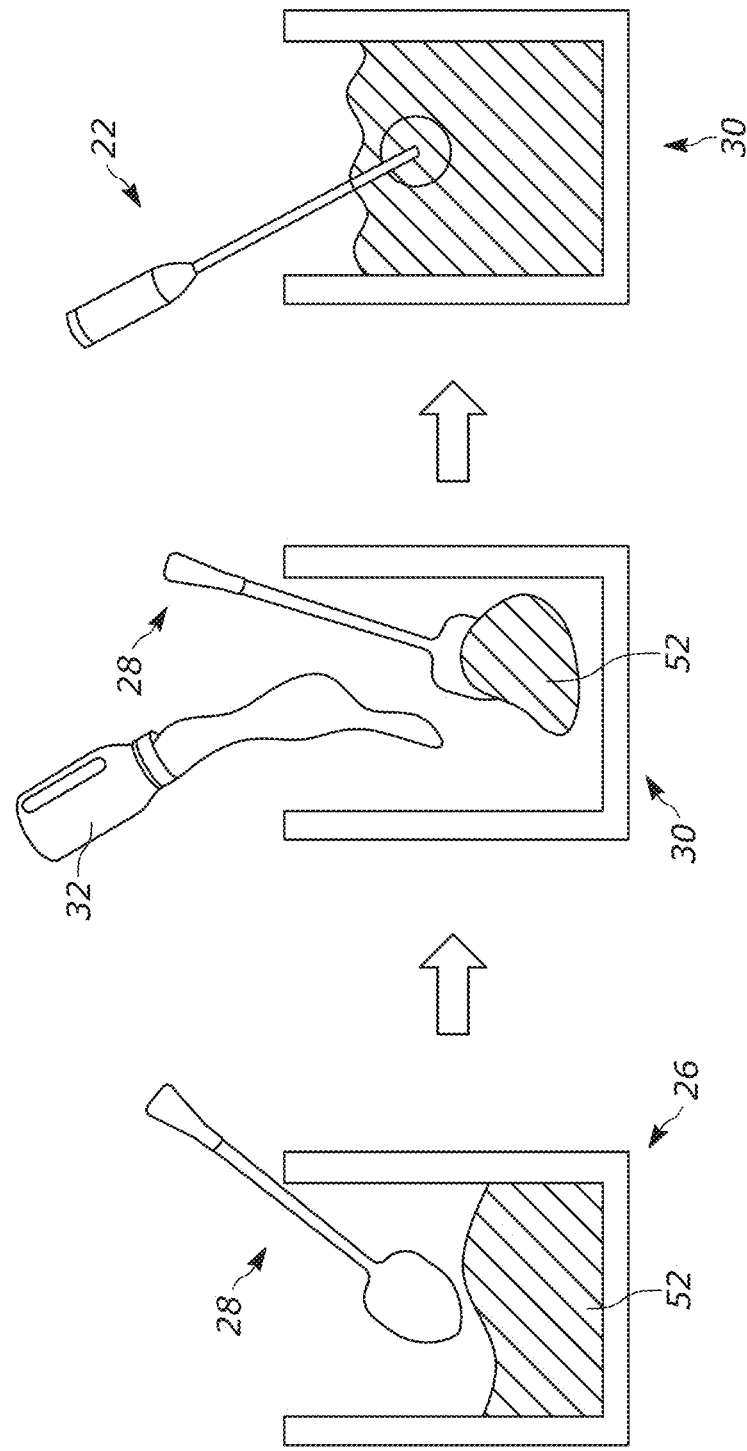

FIGS. 10A-C are schematic illustrations showing one example of the kit in FIG. 9.

DETAILED DESCRIPTION

Definitions

Unless defined otherwise, all technical and scientific terms used herein have the same meaning as is commonly understood by one of skill in the art to which the present disclosure pertains.

In the context of the present disclosure, the term "digestive tract" can refer to a tube through which food passes, including the stomach and intestines.

As used herein, the term "subject" can refer to a vertebrate, such as a mammal (e.g., a human). Mammals can include, but are not limited to, humans, dogs, cats, horses, cows, and pigs.

As used herein, the term "fecal sample", also known as a stool sample, can refer to a quantity of feces obtained from a subject for the purpose of the present application.

As used herein, the term "Proteobacteria" can refer to a major phylum of predominantly gram-negative bacteria including, but not limited to, *Escherichia* (e.g., *E. coli*), Bacteroidetes, *Salmonella, Vibrio, Helicobacter, Yersinia* and Legionellales.

As used herein, the term "peroxidase enzyme" can refer to a molecule that has the capacity to promote the oxidation of various compounds using a peroxide (e.g., hydrogen peroxide), which is reduced in the process. Thus, the "activity level" of a peroxidase enzyme can refer to the ability of a peroxidase enzyme to promote the oxidation of various compounds using a peroxide, which is reduced in the process. The term can include peroxidases that are natural, non-natural, synthetic, recombinant, endogenous or exogenous.

As used herein, the terms "myeloperoxidase" and "MPO" can refer to one example of a peroxidase enzyme, classified as EC 1.11.1.7 according to International Union of Biochemistry and Molecular Biology (IUBMB) enzyme classification, which catalyzes formation of an oxidized donor and $H_2O$ from the donor and $H_2O_2$. For example, MPO catalyzes formation of HOCl and $H_2O$ from Cl and $H_2O_2$. The term is intended to encompass derivatives, variants, and analogs of MPO that do not substantially alter its activity.

As used herein, the term "increase" or "increased", with reference to the level of Proteobacteria and the activity level of peroxidase enzymes, can refer to a measured or assayed increase (quantitatively or qualitatively) as compared to a control level.

As used herein, the term "control level" can refer to a level of Proteobacteria, or the activity of a peroxidase enzyme, from the same subject or a different subject (or subjects). A level of Proteobacteria, or activity of a peroxidase enzyme, from the same subject can be obtained at various time points previous to the most recent time point for comparison to the level of Proteobacteria or activity of a peroxidase enzyme. A level of Proteobacteria, or activity of a peroxidase enzyme, from a different subject can be obtained at the same time point as the present subject (e.g., the control subject and the present subject are the same age). Generally, the control subject and the present subject share many of the same or similar characteristics (e.g., age, weight, height, ethnicity, overall health, etc.).

As used herein, the term "chronic gastritis" can refer to inflammation of the gastric mucosa that occurs, or re-occurs, over a prolonged period of time, e.g., days, weeks, months, years. Symptoms of chronic gastritis can include, but are not limited to, indigestion, a burning or gnawing feeling in the stomach, the sensation of being full after eating a small amount, nausea and vomiting, belching, unintentional weight loss, bloating, loss of appetite, upper abdominal pain or discomfort, and gastrointestinal bleeding.

As used herein, the term "inflammatory bowel disease" can refer to a chronic inflammatory autoimmune condition of the gastrointestinal tract, which presents clinically as either ulcerative colitis or Crohn's disease.

As used herein, the term "Crohn's disease" can refer to a chronic transmural inflammatory disease with the potential to affect any part of the entire gastrointestinal tract.

As used herein, the term "ulcerative colitis" can refer to is a mucosal inflammation of the colon.

As used herein, the term "intestinal dysbiosis", also known as gut microbiota dysbiosis or gastrointestinal dysbiosis, can refer to a condition in which there is an imbalance of the microorganisms within the digestive tract, i.e., the intestines. Typical microbial colonies found on or in the body are normally benign or beneficial. These beneficial and appropriately sized microbial colonies carry out a series of helpful and necessary functions, such as aiding in digestion. They also help protect the body from the penetration of pathogenic microbes. These beneficial microbial colonies compete with each other for space and resources. When this balance is disturbed, these colonies exhibit a decreased ability to check each other's growth, which can then lead to overgrowth of one or more of the disturbed colonies which may further damage some of the other smaller beneficial ones in a vicious cycle. As more beneficial colonies are damaged, making the imbalance more pronounced, more overgrowth issues occur because the damaged colonies are less able to check the growth of the overgrowing ones. If this goes unchecked long enough, a pervasive and chronic imbalance between colonies will set in, which ultimately minimizes the beneficial nature of these colonies as a whole.

As used herein, the term "disruptive dietary component" can include any natural or synthetic food, food supplement, food ingredient, and/or combination thereof that promote(s) or increase(s) intestinal inflammation and/or unwanted changes in gut microbial composition (e.g., intestinal dysbiosis) in a subject that consumes the disruptive dietary component. A disruptive dietary component can be consumed in any amount and over any period of time. For example, a disruptive dietary component can be consumed in a relatively low amount or concentration at only one single instance and still have the effect(s) described above. Alternatively, a disruptive dietary component can be consumed in a normal amount or concentration (for a particular subject), but over an extended period of time that causes the effect(s) described above.

As used here, the term "non-caloric artificial sweetener" can refer to synthetic compounds that are hundred of folds sweeter than sucrose, and thus can be used in small amounts with negligible added caloric value. Non-limiting examples of non-caloric artificial sweeteners can include sucralose, maltodextrin, saccharin, acesulfame, aspartame, neotame, and combinations thereof.

As used herein, the term "inflammatory condition of the digestive tract" can refer to any disease or condition of all or only a portion of the digestive tract that is characterized by abnormal or unwanted inflammation as the result of an autoimmune disease, an infection, a genetic defect, a chemical agent (or agents), or a combination thereof. In one example, the term can refer to chronic gastritis or inflammatory bowel disease (e.g., Crohn's disease or ulcerative colitis).

As used herein, the term "comparing" can refer to examining in order to note similarities or differences between two or more values. In some instances, "comparing" can refer to quantitative comparisons such as, for example, subtracting one value from another, calculating a ratio of two values, calculating a percentage of one value with respect to another, or combining these types of calculations to produce a single number. The term can also refer to comparisons made by a human, comparisons made by a computer or other processor, and comparisons made by a human in combination with a computer or other processor.

Overview

In one aspect, the inventors of the present application have discovered that: (1) the artificial sweetener sucralose (known by the brand name SPLENDA® (sucralose)), worsens gut inflammation in mice with Crohn's disease, but did not substantively affect on those without the condition; (2) SPLENDA® (sucralose) produced intestinal overgrowth of *E. coli* and increased bacterial penetration into the gut wall, but only in Crohn's disease mice; and (3) SPLENDA® (sucralose) ingestion resulted in increased local (i.e., in the intestines) MPO activity of mice with Crohn's disease, but not in healthy mice.

Based at least in part on this discovery, the present application provides methods for reducing or alleviating inflammation in the digestive tract of a subject in need thereof that consumes a disruptive dietary component (e.g., a non-caloric artificial sweetener), methods for reducing or alleviating intestinal dysbiosis and intestinal peroxidase enzyme activity (e.g., MPO) in a subject that consumes a disruptive dietary component (e.g., a non non-caloric artificial sweetener), and kits for performing the methods of the present application.

Methods

One aspect of the present disclosure can include a method for reducing or alleviating inflammation in the digestive tract of a subject in need thereof that consumes a disruptive dietary component (e.g., a non-caloric artificial sweetener).

In some instances, the subject can be suffering from, or be suspected of suffering from, one or more of chronic gastritis and inflammatory bowel disease (e.g., Crohn's disease, ulcerative colitis). Methods for diagnosing chronic gastritis are known in the art and include, for example, examining a specimen (biopsy) of the stomach mucosa (e.g., during an upper endoscopy examination). Additional blood tests and tests for *H. pylori* may be required. Methods for diagnosing inflammatory bowel disease are known in the art and can include, for example, blood tests (e.g., for anemia, infection and/or other biomarkers), fecal occult blood test, endoscopic procedures (e.g., colonoscopy, flexible, sigmoidoscopy, upper endoscopy, capsule endoscopy, balloon-assisted enteroscopy), and imaging procedures (e.g., X-ray, CT, MRI). A subject suspected of suffering from one or more of chronic gastritis and inflammatory bowel disease may exhibit one or more symptoms characteristic of chronic gastritis and inflammatory bowel disease, but not yet be medically diagnosed as having such condition or disease. Characteristic symptoms of chronic gastritis are discussed above. Characteristic symptoms of inflammatory bowel disease can include, without limitation, diarrhea, fever and fatigue, abdominal pain and cramping, bloody stool, reduced appetite, and unintended weight loss. In some instances involving chronic digestive tract inflammation, inflammation can occur in the digestive tract but not be perceived for short periods of time by the subject.

In some instances, the subject consumes one or more disruptive dietary components (e.g., non-caloric artificial sweeteners). The subject can employ the methods of the present application to test the effect(s) of a particular disruptive dietary component in his or her diet. Alternatively, the subject may be directed to employ the methods of the present application on the recommendation of a medical professional (e.g., the subject's primary care physician).

In one example, the consumed disruptive dietary component can include a non-caloric artificial sweetener. Consumed non-caloric artificial sweeteners can be the same or different. The non-caloric artificial sweetener(s) can be consumed over any regular or irregular period of time. For example, non-caloric artificial sweetener(s) can be consumed daily, weekly, monthly, yearly, etc., at regular or irregular intervals. In one example, a subject can consume SPLENDA® (sucralose) and suffer from, or be suspected of suffering from, Crohn's disease.

In another aspect, one step of the method can include obtaining a fecal sample from a subject that consumes one or more disruptive dietary components (e.g., non-caloric artificial sweeteners) and is suffering from, or is suspected of suffering from, chronic gastritis or inflammatory bowel disease. Methods and kits for obtaining fecal samples generally include the following steps and components: labeling a stool container (e.g., a clean, screw-top container) with pertinent medical information (e.g., name, date of birth, date); placing the stool container in a toilet to catch the stool, or spreading clean newspaper or plastic wrap over the rim of the toilet; making sure the sample does not touch the inside of the toilet; using an instrument (e.g., spoon or spatula) to place the sample in the stool container and closing the container; and washing hands thoroughly with soap and warm running water. Kits for obtaining fecal samples are known in the art, such as the FE-COL Fecal Sample Collection Kit (Alpha Laboratories, Hampshire, UK) and the stool collection kit from DYNACARE (Quebec, Canada).

It will be appreciated that, in an alternative aspect, the sample obtained from the subject can include a urine sample.

In another aspect, the previously obtained fecal sample can be assayed (e.g., in vitro) for the presence or level of one or more Proteobacteria and an activity level of one or more peroxidase enzymes. Assays for Proteobacteria are known in the art and generally include, for example, Gram-staining (e.g., determining the ratio of Gram-positive to Gram-negative stained smears) and agar-based culture methods (such as the assay shown and described in FIGS. 8A-H as well as PETRIFILM plates available from 3M, Maplewood, Minn.).

Assays for measuring the activity level of a peroxidase enzyme are also known in the art and include, for example, colorimetric assays. Assayed peroxidase enzymes can include bacterial peroxidase enzymes associated with certain inflammatory conditions of the digestive tract, such as chronic gastritis, Crohn's disease and ulcerative colitis. Non-limiting examples of such bacterial peroxidase enzymes can include MPO, cytochrome c peroxidase, cytochrome c 551 peroxidase, thiol peroxidase, predicated dye-decolorizing peroxidase, alpha-amylase, alpha-amylase inhibitor, alpha-galactosidase, amyloglucosidase, beta-amylase, invertase, lipase, lipooxygenase, polyphenol oxidase, protease, and xylanase. Other examples of such bacterial peroxidase enzymes are known in the art. One example of an assay for MPO activity is the Peroxidase Activity Assay Kit (Sigma-Aldrich).

In an alternative aspect of the present application, a previously obtained sample from the subject can include a urine sample, which can then be assayed for the presence of a lipopolisacharide (LPS). Methods for assaying LPS are known in the art.

In one example, the activity level of intestinal MPO can be assayed using the Peroxidase Test commercially available from Medallion Labs (Minneapolis, Minn.).

After assaying the level of Proteobacteria and an activity level of one or more peroxidase enzymes in the fecal sample, the assayed or detected levels of Proteobacteria and the activity level of the peroxidase enzyme(s) are compared to respective control levels. Where each of the detected levels is increased as compared to the respective control levels, instructions can be given to the subject to decrease or eliminate ingestion of the disruptive dietary component(s) (e.g., non-caloric artificial sweetener(s)). In one example, instructions can be given to the subject by a medical professional who has compared the assayed or detected levels of Proteobacteria and the activity level of the peroxidase enzyme(s) are compared to respective control levels. In another example, the subject can compare the assayed or detected levels of Proteobacteria and the activity level of the peroxidase enzyme(s) are compared to respective control levels using a kit (discussed below). Where the assayed or detected levels of Proteobacteria and the activity level of the peroxidase enzyme(s) are increased as compared to respective control levels, the subject can then choose to eliminate or reduce ingestion of the disruptive dietary component(s) (e.g., non-caloric artificial sweetener(s)).

Advantageously, the present application provides subjects with the ability to monitor their gut (disease/health) and adjust their diets as needed based on assayed or detected levels of Proteobacteria and activity levels of the peroxidase enzyme(s).

Kits

In another aspect, a kit is provided for reducing or alleviating inflammation in the digestive tract of a subject in need thereof that consumes at least one disruptive dietary component (e.g., a non-caloric artificial sweetener). As shown in FIG. 9, the kit 10 can comprise at least the following components: a set of instructions 12 for performing the method of the present application; a peroxidase enzyme detection component 14; a Proteobacteria detection component 16; and a container 18 that houses each of the components. In one example, the peroxidase enzyme detection component 14 can comprise a colorimetric assay for detecting the activity level of a peroxidase enzyme (e.g., bacterial peroxidase enzymes associated with certain inflammatory conditions of the digestive tract, such as chronic gastritis, Crohn's disease and ulcerative colitis), which are produced and released by host fecal bacteria in response to a host reaction and, together, increase the level of peroxidase enzyme activity, which is a strong inducer of inflammation systemically and in the gut. The mechanism of inflammation is driven by the production of oxygen free-radicals, whereby the oxygen free-radicals destabilize tissue molecules and trigger uncontrollable damage thereof.

In another example, the Proteobacteria detection component 16 can comprise an agar-based assay.

Where appropriate, components of the kit 10 can be packaged in suitable containers or packs including, but are not limited to, bottles, vials, blister packs, and pouches. Additionally or alternatively, the kit 10 can include a remote detection device 20 (e.g., a cell phone) for use in detecting the level of Proteobacteria and/or an activity level of a peroxidase enzyme.

In some instances, the instructions 12 can include a paper packet or sheet that details the step-wise procedure for conducting the method of present application (as described above). Alternatively, where the kit 10 includes a remote detection device 20, the instructions 12 may refer a subject to an app, which can be downloaded onto the remote detection device and then accessed to provide the step-wise procedure for conducting the method of the present application.

One example of a kit 10 for reducing or alleviating inflammation in the digestive tract of a subject in need thereof that consumes at least one disruptive dietary component (e.g., a non-caloric artificial sweetener) is illustrated in FIGS. 10A-C. Referring to FIG. 10A, the kit 10 can include the following components: a spread mini-roller 22; an agar-based test module 24; a container 26 for receiving a fecal sample; an instrument 28 (e.g., a spoon or spatula) for transporting a fecal sample; a container 30 for homogenizing a fecal sample; a container 32 that holds a homogenization solution; and an assay module 34 (e.g., a colorimetric assay) for detecting the activity level of a peroxidase enzyme and/or LPS. Also included in the kit 10, but not shown in FIG. 10A, is a set of instructions for using the kit (as described above).

In some instances, the mini-roller 22 can comprise a "microbrouller" microbial roller that operates using a linear ruler-principle for quantifying colony forming units. The mini-roller 22 can comprise a handle 36 joined to a Y-shaped arm member 38, and a roller component 40 attached to, and located at, a distal end 42 of the mini-roller. The mini-roller 22 is adapted for use with the agar-based test module 24, which comprises first and second elongated agar strips 44 and 46, respectively, disposed on or in a substrate 48 (e.g., a plastic sheet or block). The first agar test strip 44 is formulated to promote growth of total bacteria in a previously obtained fecal sample. The second agar test strip 46 is formulated to selectively promote growth of Proteobacteria present in the previously obtained fecal sample.

In some instances, the container 26 for receiving a fecal sample and the container 30 for homogenizing a fecal sample can comprise a plastic cup, vial, or other similar vessel. Each of the containers 26 and 30 can further include a twistable or snap-fit top 50 that can be used to seal (e.g., hermetically seal) the contents of each container therein.

In some instances, the homogenization solution can comprise sterile phosphate buffered saline (PBS). Alternatively, the homogenization solution can comprise sterile deionized water. The homogenization solution can be provided in a fashion that allows the precise dilution of a fecal sample in predetermined quantities (which may range from 1:5 to 1:10000) by using the instrument 28 under well-described specifications contained in the instructions.

In some instances, the assay module 34 can include reagents necessary to detect the activity level of one or more bacterial peroxidase enzymes associated with certain inflammatory conditions of the digestive tract. In one example, the assay module 34 can comprise a colorimetric assay for detecting the activity level of MPO. For example, the colorimetric assay can be an ELISA-based assay, such as those commercially available from BioLegend Laboratories (San Diego, Calif.) and Flagellin ELISA kits. Alternatively, the assay module 34 can be used to store a sample and then be sent (e.g., by the subject or a medical professional) to a test facility for analysis (e.g., the Peroxidase Test commercially available from Medallion Labs (Minneapolis, Minn.)).

Use of certain components of the kit 10 is illustrated in FIGS. 10B-C. In FIG. 10B, a fecal sample 52 is first deposited in the container 26 for receiving a fecal sample. The instrument 28 (e.g., a spoon or spatula) is then used to transport a portion of the fecal sample 52 into the container 30 for homogenizing the fecal sample. A volume of the homogenization solution is then added from the container 32 to the homogenization container 30. The container 30 is then sealed with the top 50 and shaken to homogenize the fecal sample 52. Once the fecal sample 52 is homogenized, the roller component 40 is submersed in the homogenized fecal sample and then rolled over each of the first and second agar strips 44 and 46 (as shown in FIG. 10C).

After the mini-roller 22 has been used to spread the homogenized fecal sample over the first and second agar strips 44 and 46, a determination of the level of Proteobacteria can be made using the following formula:

Normalized Amount of Proteobacteria=[distance for Proteobacteria]/[distance for total bacteria].

The distance is determined based on a series of distance markers 54 (e.g., spaced apart in 1 cm increments) located on the agar-based test module 24. The distance for Proteobacteria is determined from the second agar strip 46, and the distance for the total bacteria is determined from the first agar strip 44.

Either before, simultaneous with, or after the level of Proteobacteria has been determined, the assay module 34 can be utilized to detect the activity level of one or more bacterial peroxidase enzymes associated with certain inflammatory conditions of the digestive tract (as described above).

After assaying the level of Proteobacteria and the activity level of one or more peroxidase enzymes in the fecal sample, the assayed or detected levels of Proteobacteria and the activity level of the peroxidase enzyme(s) are compared to respective control levels. Where each of the detected levels is increased as compared to the respective control levels, the subject can consult the instructions, which advise the subject to decrease or eliminate ingestion of the disruptive dietary component(s) (e.g., non-caloric artificial sweetener(s)). Additionally or alternatively, the subject can inform a medical professional (e.g., his or her physician) of the results and await instruction from the medical professional.

The following Example is for the purpose of illustration only and is not intended to limit the scope of the claims, which are appended hereto.

Example

Methods

Mice and Husbandry

This study was conducted with protocols approved by the Institutional Animal Care and Use Committee of Case Western Reserve University (IACUC-CWRU), using SAMP, AKR, and C57BL/6J (B6) mice, which are maintained in specific pathogen-free (SPF) colonies at the Animal Resource Center (ARC-CWRU, Cleveland, Ohio, USA). Mice were housed in shoe box cages with pine shavings for bedding, offered reverse osmosis drinking water (e.g., free of salt, bacteria, viruses), fed ad libitum irradiated standard laboratory chow (Prolab RMH 3000; porcine animal-derived fat preserved with BHA; 6.8% content by acid hydrolysis) and kept on 12-hour light/dark cycles. Age- and sex-matched mice (5-7/group) were used in all experiments. SAMP mice originated from selective sibling breeding of AKR mice, with an outcrossing to B6, as previously described. SAMP mice are prone to developing progressive ileitis with "typical cobblestone lesions" resembling the 3D features of CD. Preliminary whole-genome sequencing analysis indicates that SAMP ileitis is a polygenic disease, as is CD in humans. As needed, AKR and B6 mice were used as parental genetic ileitis-free controls. SPLENDA® (sucralose) experiments were conducted with mice produced in the main SAMP breeding colony (herein designated as facility A). A parallel alternate colony (facility B) was used for verification purposes of metagenomic findings in facility A. To maintain phenotypic and genetic homogeneity of SAMP in both facilities, periodic exchange of breeders occurred between the 2 facilities every 12 months. "Breeder mice" typically set at a 1:2 male:female ratio produced offspring "experimental mice," which are weaned at 3-4 weeks of age and maintained next to the "breeder mice" cages. *Helicobacter*-negative SPF SAMP mice, rederived as at the National Cancer Institute (Center for Cancer Research; Frederick, Md., USA), were maintained and tested on a high-level of isolation unit within the ARC-CWRU, using the husbandry standards described above.

Fecal Metagenomic Shotgun DNA Sequencing

Due to the unresolved issues associated with the metagenomic shotgun DNA sequencing analysis of all kingdoms present in the gut microbiota, which could be relevant as a cause or consequence of IBD, herein we decided to focus primarily on bacteria and screen only for viruses. To prevent sequencing and postsequencing analytical variability, validated bioinformatic methods were used on sequencing raw and high-quality filtered data (i.e., Illumina and Metaphlan). We focused on bacteria because wholesome "kingdom-agnostic" metagenomics requires controlling for large differences in cellular integrity across all members of the gut flora, which was not widely validated or available when the study was initiated.

For DNA extraction, flash-frozen fecal samples were homogenized in 1×PBS (1:5, grams:vol) with ceramic beads and mechanical disruption using Fast Prep FP120 homogenizer (setting 5 for 30 seconds at 4° C. twice, with 1 freezing cycle in between). Homogenates, after a 20-second centrifugation at 10,000×g at 4° C., were shipped overnight to the laboratory of Dr. Skip Virgin at Washington University, St. Louis, Mo. DNA extraction and purification from the homogenates were performed using the commercial Qiagen DNA extraction mini-kit following the manufacturer instructions. The integrity (and quantity) of the DNA was monitored by spectrophotometry and gel electrophoresis. dsDNA was quantified with an Invitrogen Qubit Fluorometer (8.62±5 µg/mL; Quant-iT). Shotgun metagenome analysis was conducted following library preparation using Illumina reagents and Miseq sequencing validated protocols. Standard Fastaq files were then used to quantify the abundance of bacterial reads using MetaPlhan alignment and analytical pipelines developed by Dr. Huttenhower at the Harvard School of Public Health. Briefly, raw FASTQ files were transferred to a local server where Metaphlan pipelines were run on Galaxy, where the R1 and R2 fasta files were concatenated, then assembled and blasted using bowtie2 very-sensitive-local search. Metaphlan output files were then merged using the merge_metaphlan_tables.py script, and were normalized and analyzed using Metaphlan and R visualization tools.

SAMP Ileitis Transmissibility, Cohousing, and Fecal Microbiota Homogenization

To determine if the passive exposure of fecal pathogens in a confined space during cage cohousing could alter the expected morphological mucosal pattern (presence/absence of cobblestone ileitis) of both AKR and SAMP colonies, 3-week-old SAMP and age/sex-matched AKR mice were weaned and subjected to a 24-week period of cage cohousing. As our metagenome data indicated that there was a relevant microbiota variability within the colony over time, SPLENDA® (sucralose) experiments were conducted 7 days after implementing a fecal flora (microbiota) homogenization protocol (IsPreFeH), where all mice were exposed to a composite (pool) of feces from all intended experimental mice, by gavaging 400 µL of fecal suspensions to each mouse.

Artificial Sweetener Experiments in Mice

To determine the effects of SPLENDA® (sucralose) supplementation on SAMP ileitis and gut microbiota, we conducted 3 separate experiments with incremental adjustments. In experiment 1, we added a "low dose" of SPLENDA® (sucralose) (1.08 mg/mL) to the drinking water for 6 weeks and compared it to "plain water" using only SAMP mice (6/group). Body weight, microbiological culture-based data (feces and spleen), and ileal histological and SM scores were the main study outcomes. In experiment 2, we repeated the same protocol but increased the dose to the maximum recommended by the US Food and Drug Administration (FDA; 3.5 mg/mL) and included AKR mice (6/group). The fecal bacteriome changes were assessed using 16S rRNA microbiome, glucose tolerance tests, and a well-validated method of biochemical inflammation based on the enzymatic detection of MPO activity in both the ileum and colon (Rodriguez-Palacios, A. et al., Nat Commun. 2015; 6:7577; Rodriguez-Palacios, A. et al., Protoc Exh. 2015). Finally, systemic inflammation was evaluated by serum tumor necrosis factor-alpha (TNFα) levels (Ready-Set-Go ELISA kit eBioscience, San Diego, Calif., USA), and glycemic responses were assessed by glucose tolerance tests. In experiment 3, we repeated protocol 2 but administered SPLENDA® (sucralose) at a dose that was 10 times higher than the dose used in experiment 2 (i.e., 35 mg/mL). The main outcomes were MPO activity and intestinal inflammation (histology and SM). To minimize cage-to-cage clustered variability, all animals were housed individually, and all water bottles were replaced every 48 hours to provide fresh supplementation and prevent bacterial over growth. An irradiated/autoclaved standard diet was offered to all mice during experimentation to prevent external microbial confounders. We have recently reported the effect of soiled bedding in the mouse microbiome as a source of "cyclical bedding-dependent bias" in microbiome research, which could be varied depending on a number of factors, including the number of mice, microbiota, and humidity. In the present study, we controlled for "cyclical bias" by (1) housing all mice individually, (2) maintaining all cages in HEPA-filtered pressurized standard dorms (low cage humidity), (3) replacing all cages simultaneously weekly, and (4) collecting all data (food consumption, fecal samples, euthanasia) and samples (live and postmortem) for all animals the same day. Stereomicroscopic 3D pattern profiling (to determine the presence of SM abnormalities on the mucosal surface) and histological assessment were conducted on Bouin's fixed intestinal tissues. Histological evaluation of inflammation severity was determined by hematoxylin and eosin-stained 5-μm-thick sections using a semi-quantitative scoring system. A board-certified pathologist determined all scores in a blinded fashion. The detailed 3D-SMAPgut protocol's considerations, along with the scoring forms and criteria, have been validated and described elsewhere.

Relative Multidilution Enumeration of Fecal Bacterial Communities Using a "Parallel Lanes Plating" Method Traditionally, the enumeration of total bacteria from feces has been conducted using spread plate methods, which require up to ten 10-fold serial dilutions to inoculate 100 μL of each dilution in individual agar plates (Dore, J. et al., *FEMS Microbiol Lett.* 1995; 130:7-12; Herigstad, B. et al., *J Microbiol Methods.* 2001; 44:121-9). For feces, which contain up to 8-9 $\log_{10}$ colony-forming units (CFUs) of bacteria per gram, a full quantitating spectrum requires up to 10 agar plates. To reduce costs, scientists often plate dilutions 7, 8, and 9 to estimate the fecal CFU counts, leaving more concentrated dilutions (1 to 6) unexamined. Other methods used for enumeration of mono-strain bacterial suspensions in food science use 5-μL drops of each 10-fold serial dilution to be "spotted"/incubated on an agar plate. Despite their simplicity, spotted platting only allows the collection of binary data (presence/absence of growth in each spot) to obtain "approximate" CFU $\log_{10}$ range counts (most probable number/dilution), with no capabilities to compare the relative growth or inhibition potential of cocultured strains. As we were interested in estimating the relative concentrations of mouse fecal bacterial communities, which may vary in natural abundance and which would be prohibitive to examine with spread plating methods in the SPLENDA® (sucralose) experiments, we developed a method herein referred to as "parallel lanes plating" to rapidly estimate total and relative bacterial abundances across numerous dilutions using a single agar plate. This method allows the plating of 8 to ten 10-fold dilutions for the simultaneous enumeration of CFU for bacterial subgroups exhibiting colonies of distinct morphological appearance, irrespective of their concurrent high or low abundances within the same sample. In brief, the method uses 10-20 μL of all 10-fold serial fecal dilutions in PBS, which are placed simultaneously as drops using a multichannel dispenser on 1 side of a tilted agar plate (>60°-80° angle). The inclination of the agar plate makes the drops slide downward over the agar surface, creating parallel lanes of spread solutions of up to 5-cm$^2$ surface area, which allows the easy identification and enumeration of distinct bacterial colonies and inhibitory interactions across all fecal dilutions (0.5×10 cm) (FIGS. 8A-H). Upon drying and 48 hours of aerobic and anaerobic incubation at 37° C., single colonies were enumerated relative to total CFUs of cultivable bacteria in the sample. Agars used included Brain Heart Infusion (BHI) or tryptic soy agar (TSA) supplemented with 5% sheep blood (BD, Downers Grove, Ill., USA), Luria Brentani (LB; enterobacteria), de Mann Rogose Sharpe (lactobacilli), meat liver (fastidious anaerobes and sulphite reducers), and plain microbiological agar supplemented solely with either yeast extract, maltodextrin, or SPLENDA® (sucralose) (at 3.5%). In selected media (TSA), purified colonies were Sanger sequenced following standard protocols. Specific *Helicobacter* primers were also used to semiquantify *Helicobacter* spp. in feces and tissue of selected animals using amplicon gel analysis (Brown, D. R. et al., *J Nutr.* 1985; 115:347-51).

16S rRNA Gene Microbiome Analysis

Microbiome analyses were conducted at CWRU using Ion Torrent protocols, which have been validated and described in detail (Hoarau, G. et al., *MBio.* 2016; 7:e01250-16, 1:11; Mukherjee, P. K. et al., *PLoS Pathog.* 2014; 10:e1003996). To quantify bacterial changes associated with the 6-week supplementation of SPLENDA® (sucralose), we used pure DNA from end point fecal samples (day 42-47) to PCR-amplify the V4 region of the 16S rRNA gene in triplicate using primers as previously reported (Mukherjee, P. K. et al., *PLoS Pathog.* 2014; 10:e1003996). PCR products were then evaluated by electrophoresis in 2% agarose gel and purified with the Agencourt AMPure XP system. PCR amplicons were selected to obtain 400-bp length for library preparation and were sequenced using Ion Torrent reagents and a benchtop sequencer at CWRU (Chakravorty, S. et al., *Microbiol Methods.* 2007; 69:330-9; Huse, S. M. et al., *PLoS One.* 2012; 7:e34242). For sequence analysis, the mothur package of algorithms (v1.32.1) (Schloss, P. D. et al., *Appl Environ Microbiol.* 2009; 75:7537-41) and associated dependencies were used. As we previously reported (Mukherjee, P. K. et al., *PLoS Pathog.* 2014; 10:e1003996), aligned paired-end reads aligned to Silva 16S rRNA reference database.b Sequences that were >244 bp or <239 bp in length that contained any ambiguous base calls or long runs (>8 bp) of holopolymers or did not align with the correct region were removed. bChimeras were identified using uchime and were eliminated. bCatchAll was used to assess species richness, while taxonomy assignment relied on the RDP taxonomy database. bSequences were binned into operational taxon units (OTUs) at a 3% dissimilarity level. Instead of subsampling for normalization, we normalized the OTU tables by rescaling the abundances of all samples to the fecal sample having the lowest total sequence abundance in the study. R software was used to visualize the microbiome profile and compute univariate and multivariate statistics. Dendrograms were computed using Euclidean distances, and when distinct unsupervised hierarchical clusters were observed, we tested the mouse allocation using frequency statistics (Fisher exact). In this fashion, we determined whether the allocation of mice to the microbiome clusters was random or significantly linked to the study variables, especially mouse strain and treatment (SPLENDA® (sucralose) or plain water).

Quantitative Polymerase Chain Reaction of Mucosa-Associated Bacteria

DNA was isolated from ileal tissue using the Roche High Pure PCR Template Prep Kit for genomic DNA isolation. qPCR was performed using 10 ng of DNA in all reactions and primers for Eubacteria (Nadkarni, M. A. et al., *Microbiology.* 2002; 148:257-66) or six 16S rRNA-specific sequences for *Escherichia coli* (Huijsdens, X. W. et al., *J Clin Microbiol.* 2002; 40:4423-27), *Bacteroides, Lactobacillus/Enterococcus, Eubacterium rectale/Clostridium coccoides* (Erec), segmented filamentous bacteria (SFB), and mouse intestinal *Bacteroides* (MIB) (Vaishnava, S. et al., *Science*. 2011; 334:255-8) in iTaq SYBR Green Supermix with ROX (BioRad) on an ABI prism 7900HT (ThermoFisher Scientific) using SDS2.4 software. Samples were run in triplicate. Because there is no proper widely accepted "reference control bacterial population marker" to normalize qPCR microbiome data, quantitative strain-specific 16S primer amplicon data were analyzed collectively using the raw qPCR-CT values as described earlier (Rodriquez-Palacios, A. et al., *Nat Commun*. 2015; 6:7577) and multivariate statistics to visualize and quantify the overall impact of the AS supplementation on the mucosa-associated microbial composition in the ileum of mice.

Fluorescent In Situ Hybridization

To visualize the localization of bacteria carrying the maIX gene, which encodes for maltodextrin-degrading enzymes, ileal tissues were fixed in methanol-based Carnoy's fixative (60% absolute methanol, 30% glacial acetic acid, 10% chloroform), embedded in paraffin blocks, and sectioned. Five-μm sections were deparaffinized and hybridized with 250-ng *E. coli*-Cy3 probe, 500-ng MaIX-Alexa488 probe, and Eubacteria338-Alexa647 probe or buffer-only controls in 20-mM Tris-HCL, 0.01% SDS, 0.9M NaCl at 46° C. overnight (Shen, X. J. et al., *Gut Microbes*. 2010; 1:138-47). Slides were then rinsed twice with water, incubated 5 minutes in 20-mM Tris-HCL, 0.9M NaCl at 46° C., rinsed twice with water, dried 10 minutes at 46° C., and applied with Vectashield containing DAPI (Vector Labs) and coverslips. Imaging was acquired using a Leica TCS-SP spectral laser scanning confocal microscope equipped with a Q-Imaging Retiga EXi cooled CCD camera and Image ProPlus Capture and Analysis software (Media Cybernetics). Image z-stacks were collected every 0.49 μm spanning the full thickness of cells and exported for image analysis using Image ProPlus Capture and Analysis software (Media Cybernetics).

Statistical Analysis

In all experiments, mice were randomized using a systematic approach. We used optimal analytical and matching strategies to control for confounding bias, as implemented in interventional and observational studies (Dohoo and Stryhn, *Confounder Bias: Analytic Control and Matching. Veterinary Epidemiologic Research*. 2005). Further, blinding was enforced in experimental and analytical stages as SPLENDA® (sucralose) supplementation or *Helicobacter* status was not obvious to handlers; noninformative codes were revealed after analysis. Both univariate and multivariate statistical analyses were conducted independently for each SPLENDA® (sucralose) dosing. Parametric statistics (Student t tests and/or 1-way analysis of variance [ANOVA]) or their nonparametric alternatives were used to compare experimental data (i.e., body weight, inflammatory scores, MPO activity). Metagenomic and microbiome bacterial abundance data (OTU taxonomic tables) were log transformed, normalized, and processed using R software or STATA. Multivariate Hotelling's T-squared distribution statistics was used for the comprehensive analysis of bacterial qPCR tissue data. Data were presented as SD or 95% confidence intervals; significance was held at $P \leq 3.05$. P values between 0.05 and 0.1 are also shown when appropriate.

Results

The Gut Metagenome of Ileitis-Prone SAMP Mice is Rich in Families of the Phylum Bacteroidetes Prior to testing the effects of SPLENDA® (sucralose), we first examined the gut metagenome profile of the SAMP "experimental mouse" colony compared with the AKR, which have been maintained together in the same animal CWRU facility for more than a decade. Because each colony could have selected for their own microbiome, adapted to their health or diseased intestinal environment through the years, it was important to determine whether potential microbiome differences ("shifts/drifts") could be attributable to the IBD susceptibility genotype and the progressive SAMP phenotype (mild inflammation in young; severe inflammation in adult). For this purpose, fecal samples from 6 experimental mice (3 males, 3 females; 6 cages) across 3 different age groups (7, 22, and 50 weeks) (see experimental design in FIG. 1A) were collected, processed, pooled for DNA extraction, and sequenced using metagenome MiSeq Illumina sequencing reagents. We used pooling to create a composite sample for each age group as a valid screening method to control for background individual and cage variability, because fecal pooling is a powerful and cost-effective approach to study the microbial phenotype of large animal populations (with pooling of 5-10 individual samples showing optimal performance). At the phylum level, metagenomics revealed a significant increase in the Bacteroidetes phylum in SAMP mice. At the class level, within the Bacteroidetes, Sphingobacteriia and Bacteroidia were increased in SAMP compared with AKR mice (FIGS. 1B-E). Within these 2 classes, out of 7 possible in the phylum Bacteroidetes, which was the most abundant phylum in the study, it is remarkable that the most abundant species identified in the phylum belonged to 4 out of 6 possible genera in the class Bacteroidia (*Prevotella*, Alistipes, Parabacteroides, and *Bacteroides*; Order Bacteroidales). Collectively, Bacteroidia was most commonly altered in SAMP mice compared with only 1 genus increased out of 6 possible in Sphingobacteriia (1/6 vs 4/6; 1-tailed Fisher P=0.045) (see species in FIG. 1E). This finding is experimentally relevant to CD because CD has been associated with Bacteroidetes-enriched dysbiosis (e.g., *Bacteroides* and *Prevotella* genera in human gut mucosal samples).

Within the phylum Proteobacteria, analysis at the family level revealed a striking increase of Helicobacteraceae (C: Epsilonproteobacteria; O: Campylobacterales) in SAMP mice (FIGS. 1B-E). However, as Helicobacteraceae (the sixth most abundant family in the study, out of 41) was already abundant in young SAMP mice (7 weeks of age), the findings suggested that Helicobacteraceae abundance was not due to the severity of ileitis, which is typically undetected at 3 weeks of age but affect >60% of ileum by 55 weeks of age. Because metagenomics is robustly based on the quantification of bacterial communities using single-copy gene data, results from pooling (n=36) mice strongly indicated, for the first time, that the SAMP microbiome phenotype is rich in several Bacteriodetes families, and surprisingly dichotomous and rich in Helicobacteriaceae. Because *Helicobacter* has been considered both a confounding factor and a necessary organism in certain B6 mouse models of colitis, but not all, it was deemed necessary to confirm the findings with a new set of samples for individual (not pooled) metagenomics, especially as Bacteroidales and Helicobacteraceae are known inhabitants of the human intestine with the potential to become opportunistic pathogens, for example, *Odoribacter splanchnicus* (FIGS. 1A-E).

Virome Sequencing Reveals Absence of Norovirus in "Pooled Feces"

To further investigate the microbiome of the "pooled feces" experiment in our colony, fecal samples were also processed and shotgun-sequenced using a Roche 454-sequencing platform to screen for the presence of DNA and cDNA viral genomes, in addition to Illumina sequencing.

Metagenomic examination of the sequences indicated the absence of norovirus in the pooled samples. Thus far, metagenomic analysis has indicated the absence of detectable dsDNA viruses in the pooled feces of young SAMP and AKR mice. PCR for norovirus and novel astroviruses were also negative, although testing of our SPF colony has been shown to be variably seropositive for norovirus over time. We recently reported a concurrent serological screening of adult SAMP mice reared under germ-free (GF) conditions, wherein SAMP exhibiting cobblestone ileitis had no seroconversion to norovirus for up to 62 weeks of age. Thus, serology indicated that SAMP ileitis occurred independently of norovirus, a virus needed to promote intestinal inflammation in ATG16L1 gene-dependent models using B6 mice.

Figure 1A:
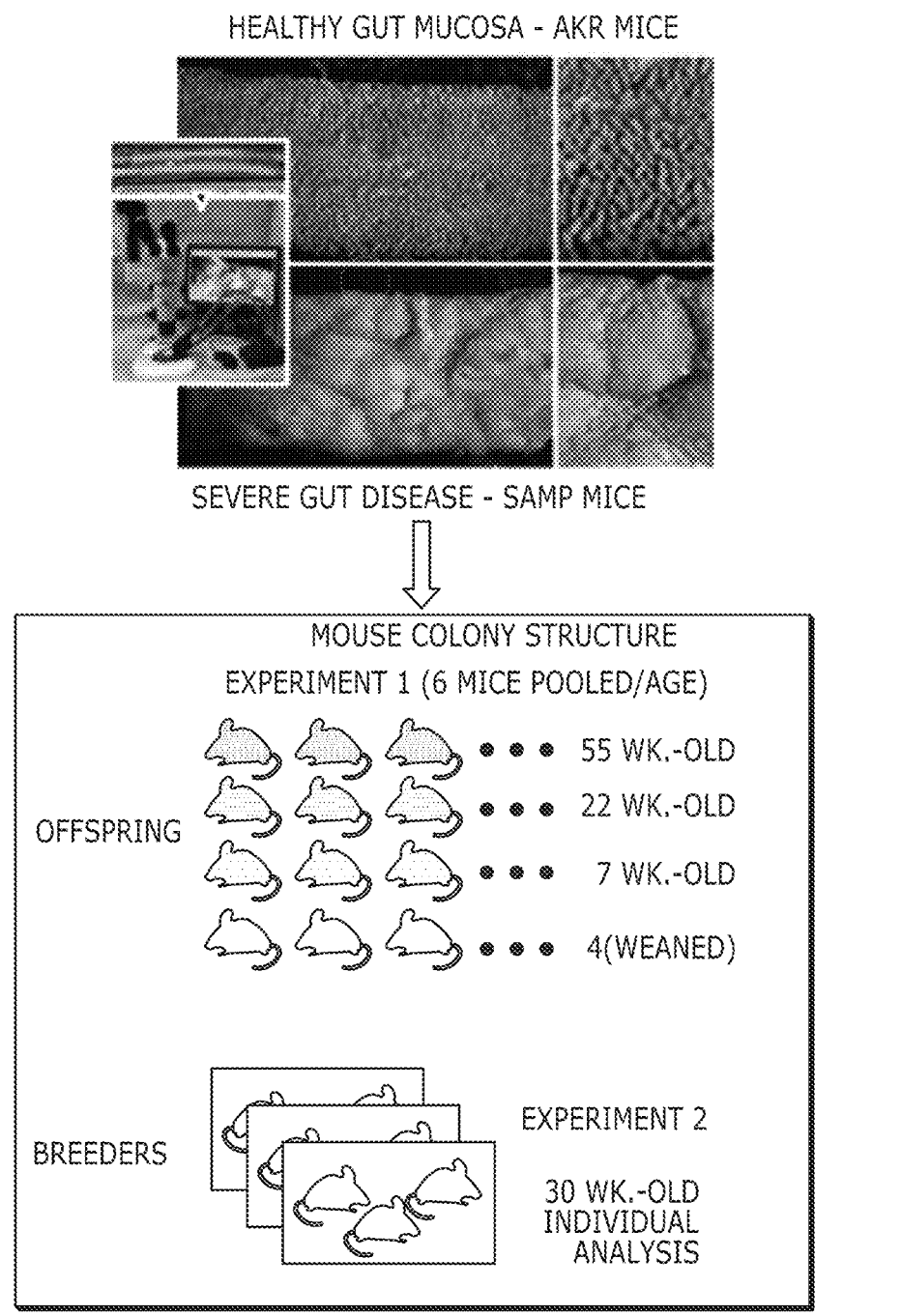
FIGS. 1A-E show metagenomic analysis of pooled fecal matter reveals an abundance of Bacteroidetes and Helicobacteraceae in SAMP mice.
Figure 1B:
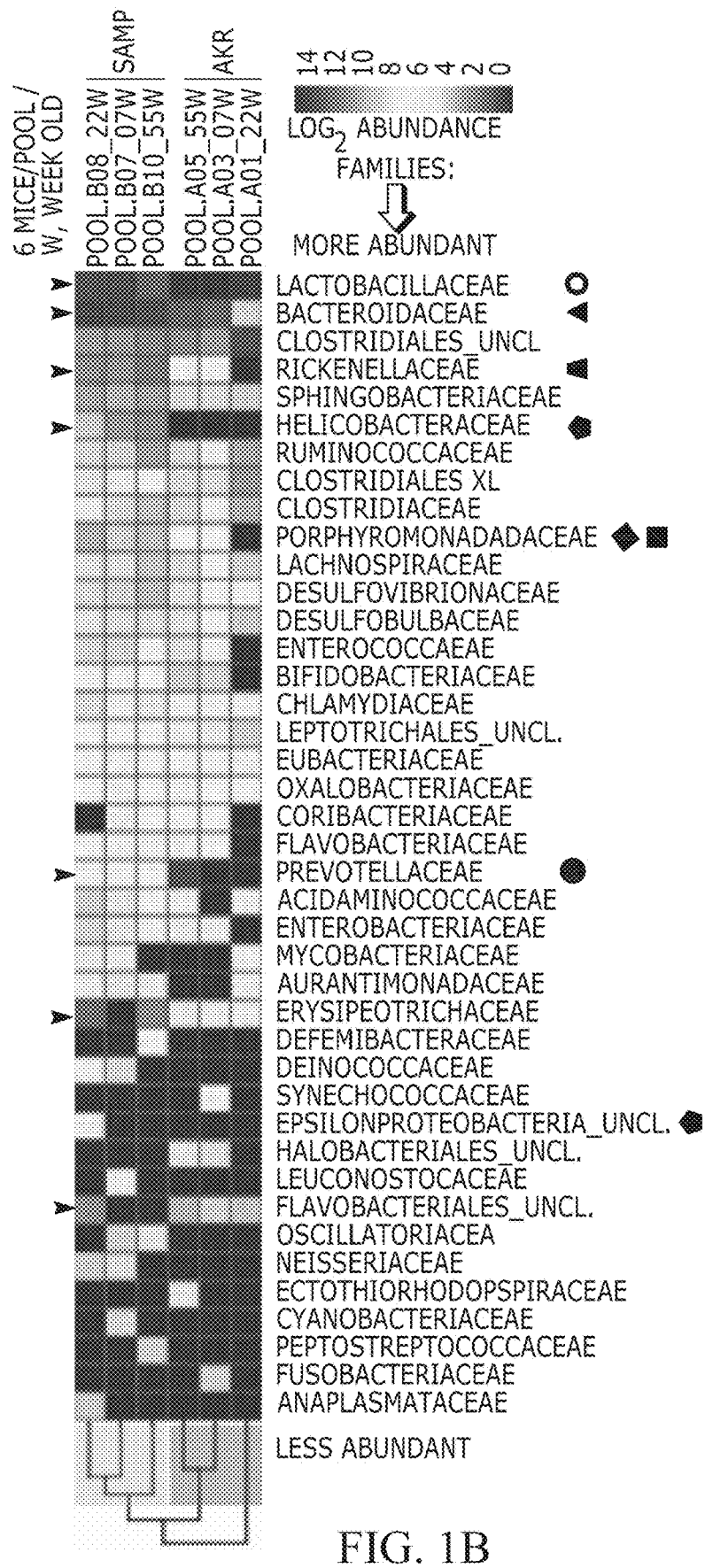
Figure 1C:
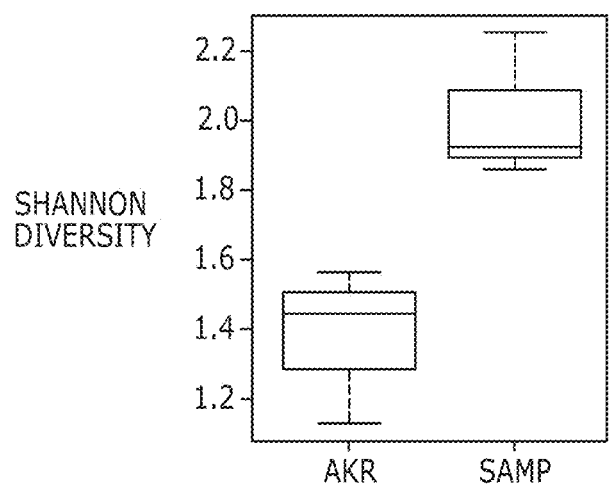
Figure 1D:
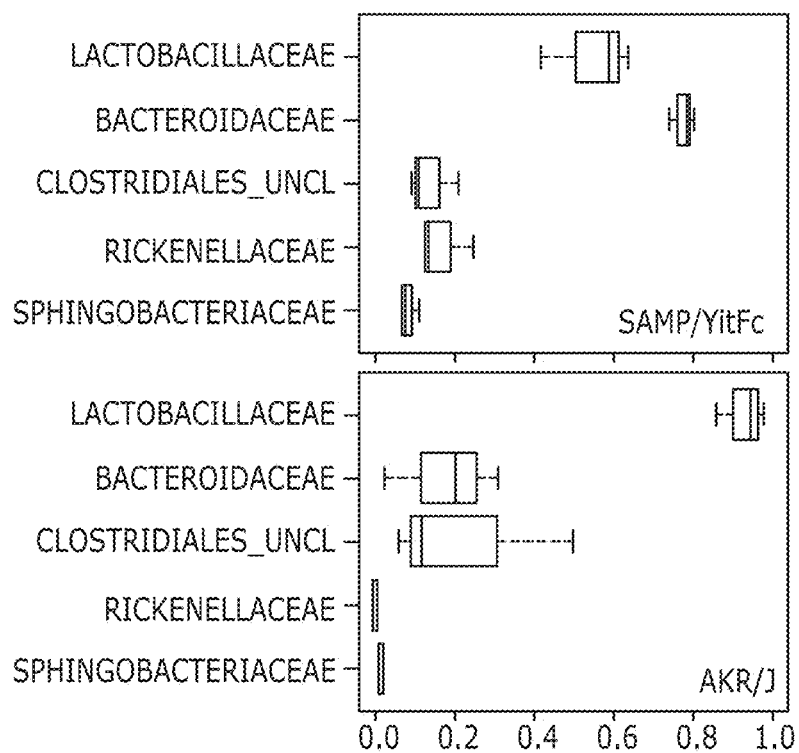
Figure 1E:
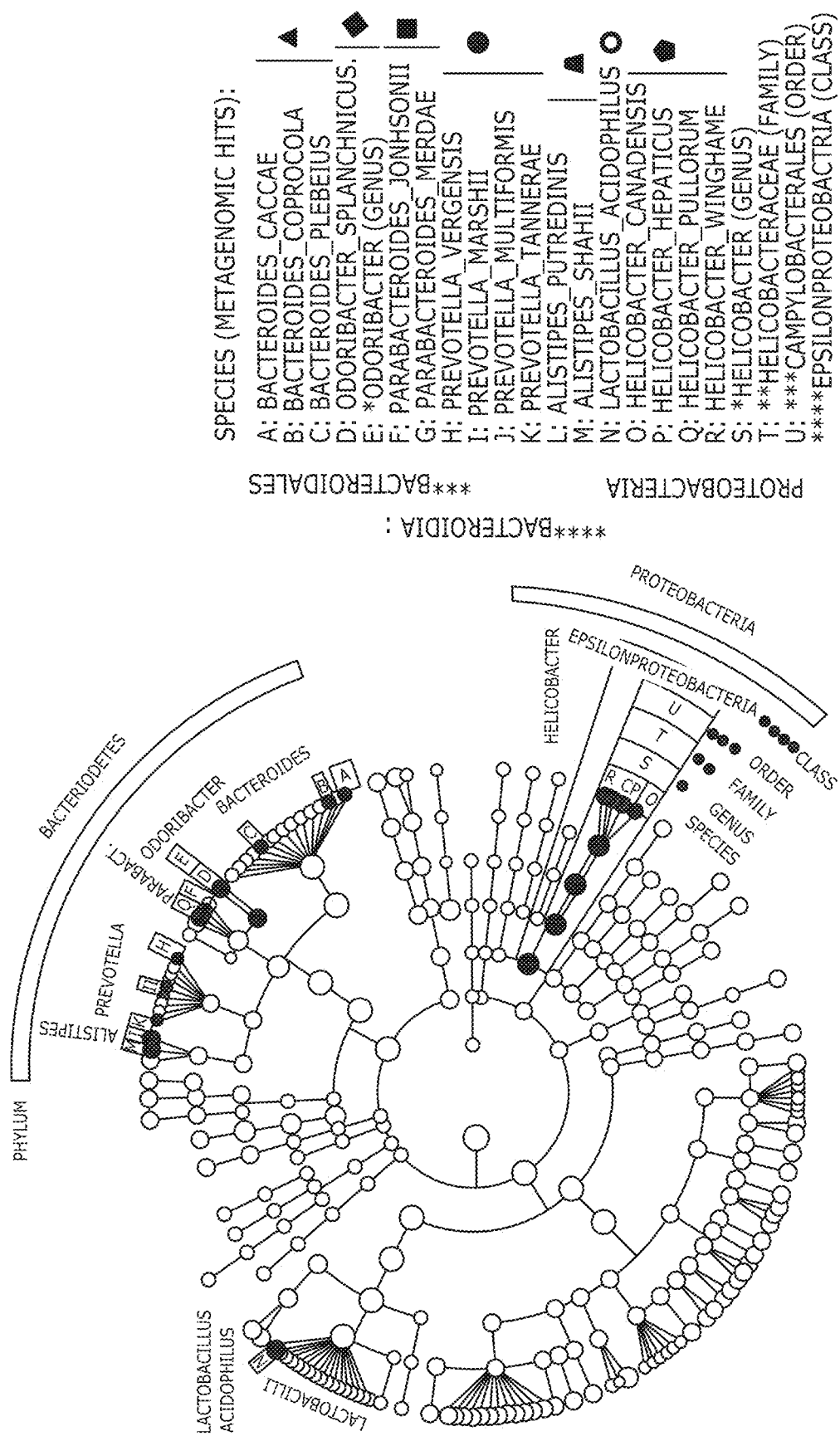

Individual Metagenomics Illustrate Great Cage and Facility Variability of *Helicobacter* in Mice To verify that Helicobacteraceae was stably abundant in SAMP mice over time, a second metagenomic analysis was conducted 8 months after the "pooled" metagenomics evaluation, but testing individual fecal samples from "breeder mice." Paired male:female mice were sampled as clustered by cage to validate the reproducibility of our unsupervised metagenome hierarchical analysis used in the pooled metagenome analyses of "experimental mice." Eighteen active 30-week-old breeders (1 male, 1 nonpregnant female/cage) were tested as representative because they would be the main source of gut commensal microbes inherited to the offspring "experimental mice" sampled earlier. To properly determine whether Helicobacteraceae was abnormal in SAMP, B6 breeders were also sampled, along with the original AKR vs SAMP colonies (FIG. 1A). To ensure compliance on scientific rigor and data reproducibility, SAMP and AKR mice were also sampled from an alternate colony (in facility B). Unexpectedly, metagenomic analysis (54.4 million raw reads; 20.9 million high-quality bacterial paired-end, 79±5% unique) revealed major variability for Helicobacteraceae across the colonies and facilities, further challenging the relevance of Helicobacteraceae as causally associated with SAMP ileitis. This time, *Helicobacter* was absent in 3 cages of SAMP and B6 mice, but abundant in a cage of AKR in our facility A (FIG. 2A), which was opposite to concurrent findings in facility B. Analysis clearly showed that the ability to sequence *Helicobacter* in SPF mice was highly variable and dichotomous in metagenomics (either highly abundant or absent), likely due to seasonality or individual cage differences. Given the high variability, no absolute conclusion could be drawn regarding the potential causal or modulatory role of *Helicobacter* on SAMP cobblestone ileitis. However, the analysis (1) confirmed that *Bacteroides* are abundant in adult SAMP mice and (2) verified the optimal reproducibility of our metagenomic methods as pairs of breeders always clustered together (as expected within their cage assignment, despite notorious "mouse individualities") using unsupervised clustered analysis (FIGS. 2A-D).

The Presence of Helicobacteraceae does not Alter Cobblestone Lesion Progression in SAMP Ileitis

Figure 2A:
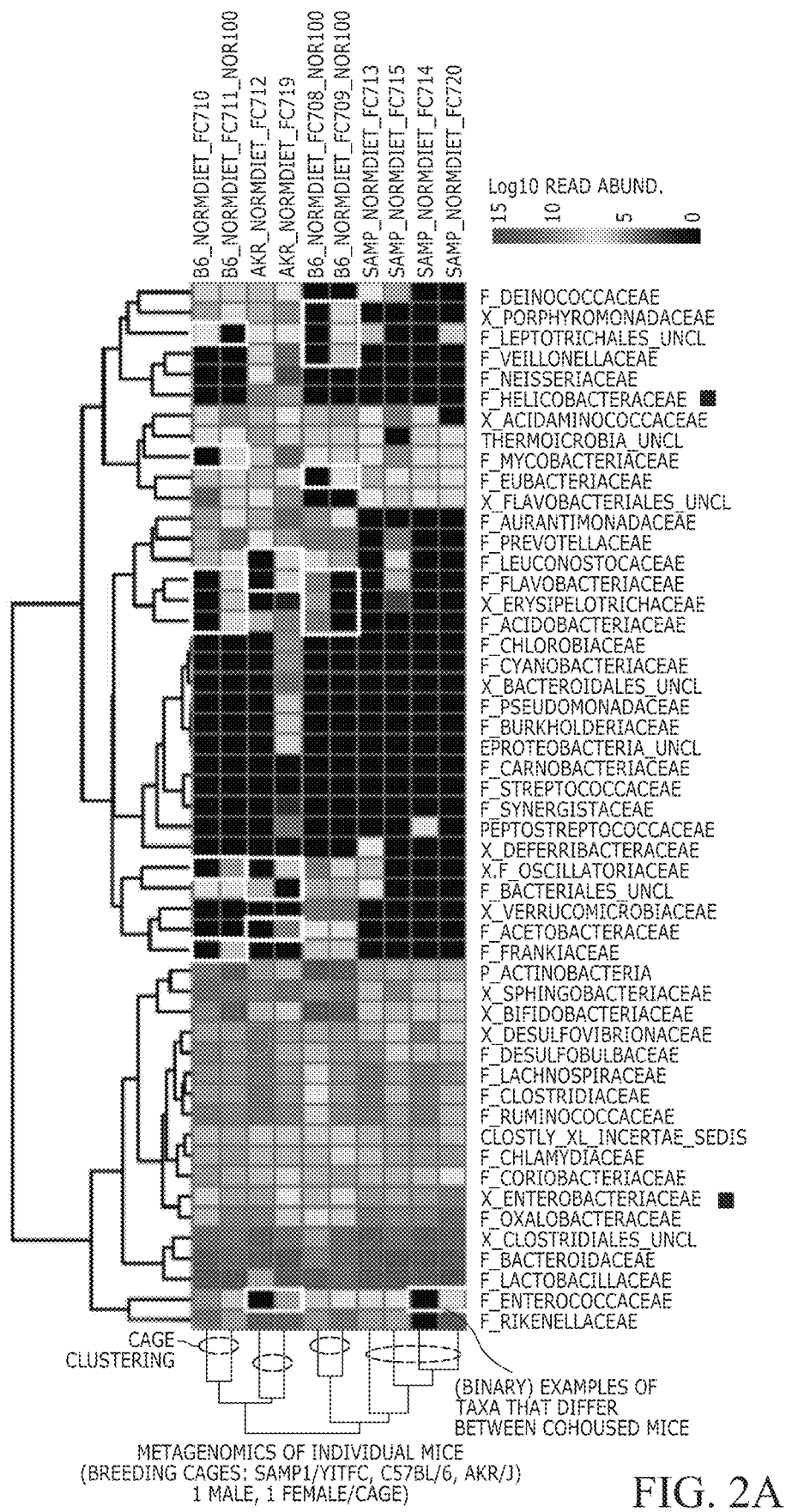
FIGS. 2A-G show metagenomic analysis reveals *Helicobacter* variability with minimal effect on SAMP ileitis.
Figure 2B:
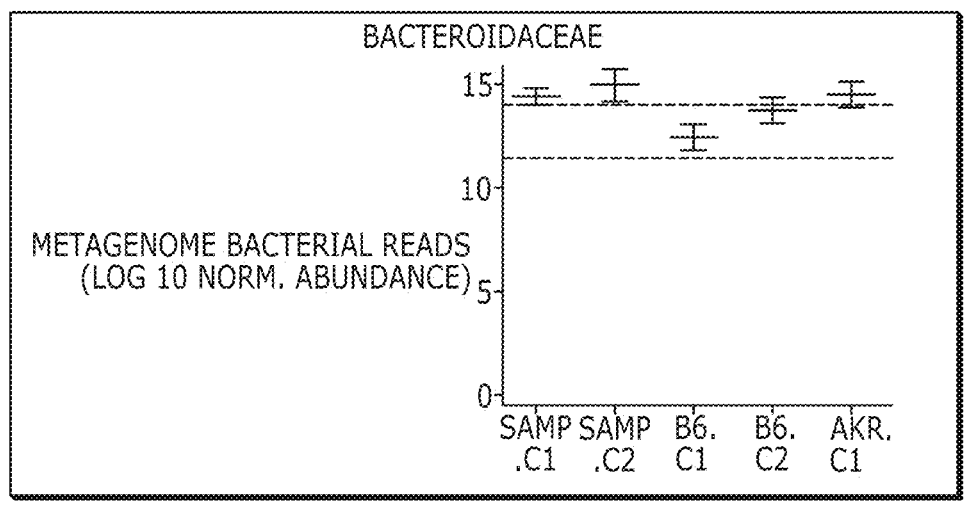
Figure 2C:
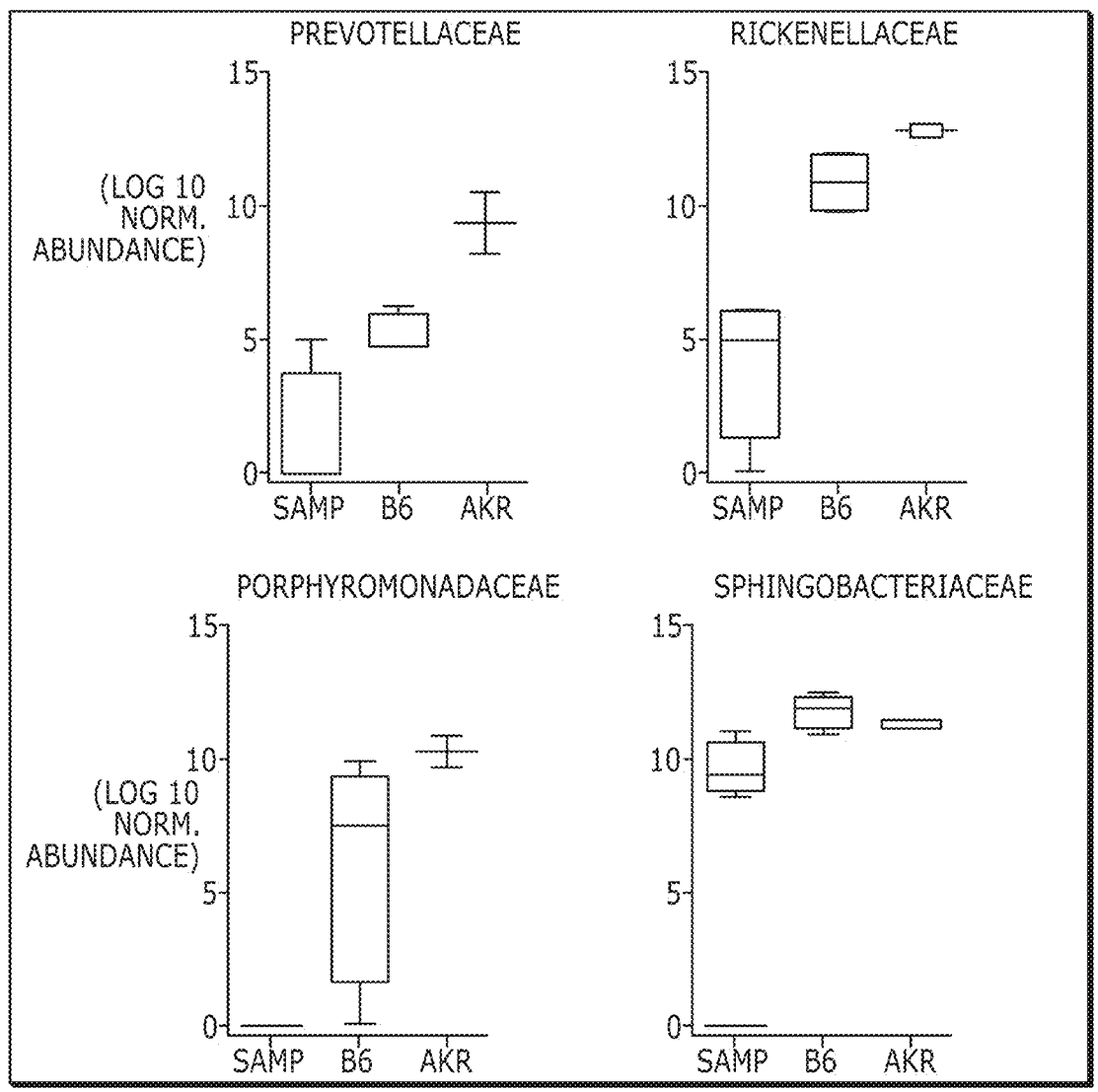
Figure 2D:
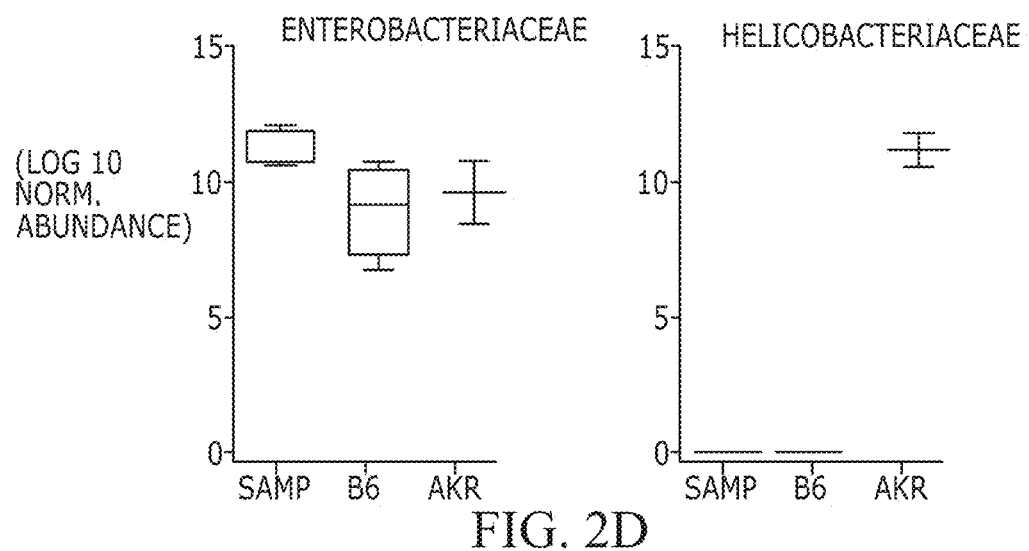
Figure 2E:
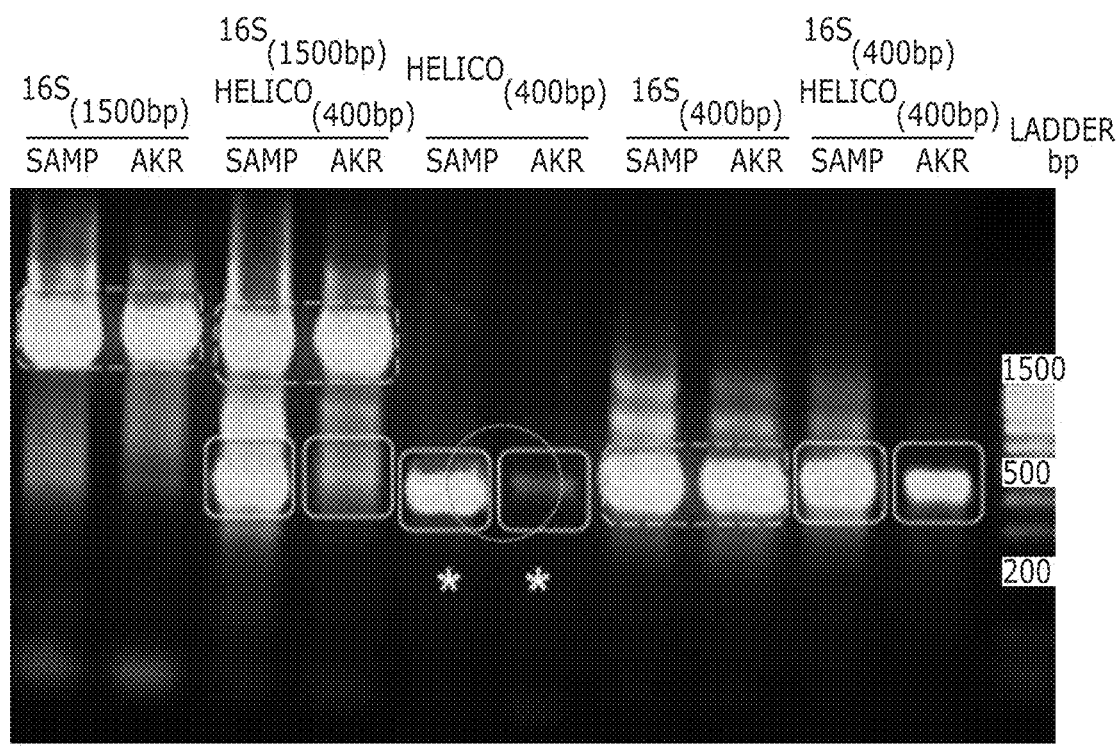
Figure 2F:
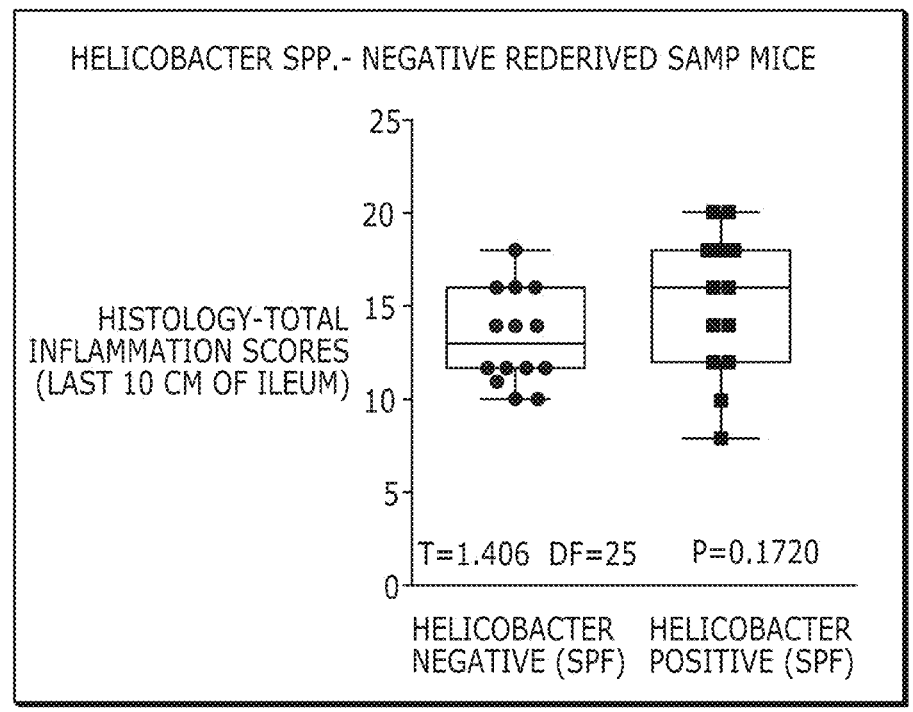
Figure 2G:
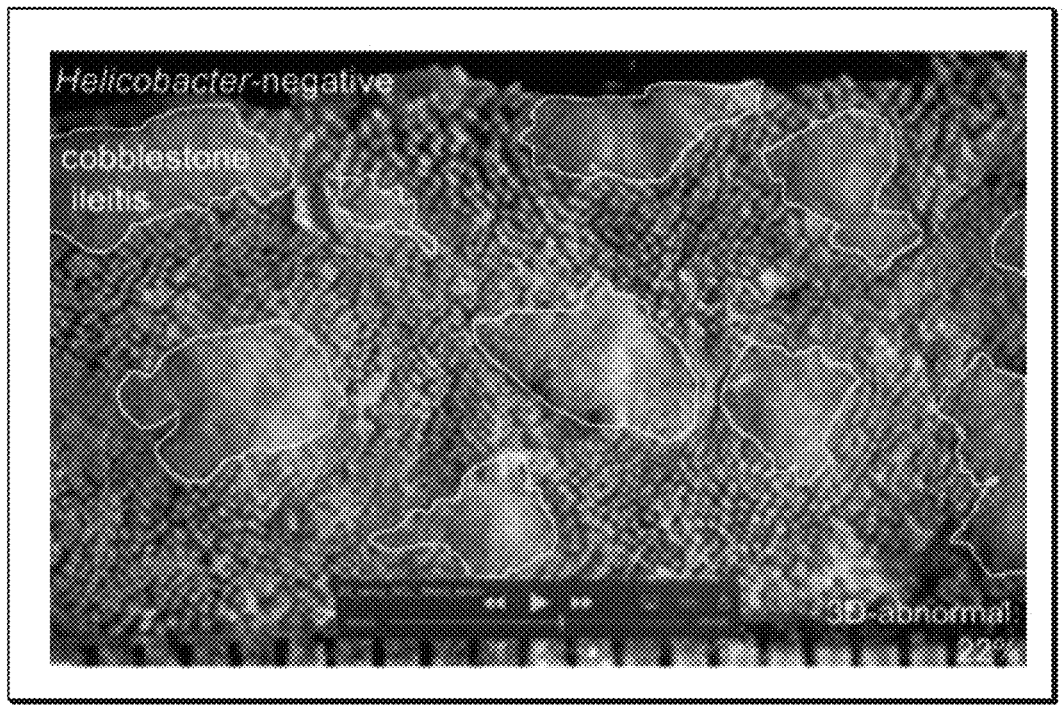

*Helicobacter* spp. specific 16S-primer amplification of fecal bacterial DNA confirmed that both mouse lines (SAMP and AKR) in facility A harbored the bacterium in their feces and that SAMP could have more DNA copy numbers than AKR (FIG. 2E). Because the initial pooled metagenomic analysis indicated a strong signature for *Helicobacter* spp. in SAMP, we then created a new SAMP colony by rederivation and colonization with a *Helicobacter*-negative mouse microbiota at the National Institutes of Health. Following rederivation, breeding pairs were transported and housed in our facility for phenotype testing. SM analysis of the small intestines of mice at 30 weeks of age revealed a persistence of the 3D cobblestone lesion architecture in the inflamed ileum, whereas histological analysis over time of this colony revealed that *Helicobacter* was not necessary for the disease to occur or histologically worsen (the study of immunophenotyping differences is in progress and will be reported separately) (FIG. 2F).

The SAMP Ileitis is not Transmissible or Preventable During Long-Term Cohabitation with Healthy Mice We found no evidence to suggest that the anti-inflammatory benefit of the NOD2 mutation was due to a given microbiome profile based on fecal metatranscriptomic (bacterial gene expression mRNA) and 16S microbiome analyses. Although the concept of transmissible colitis seemed relevant to the genetics of B6 mice, the genomic differences in our SAMP model and its spontaneous progressive ileitis phenotype prompted us to determine whether microbiome exposure of young 3-week-old healthy AKR mice during cohousing could protect young 3-week-old SAMP mice from developing ileitis, and whether disease could be transmissible from SAMP to AKR in a long-term experiment. The experiment was conducted for 6 months with 14 mice. 3D-SMAPgut analyses showed that the 3D ileitis phenotype was not transmissible to AKR mice and that SAMP ileitis was not prevented during cohabitation with AKR. Culture analysis (anaerobes and enterobacterial fecal enumeration) indicated that although the total bacterial load was similar for AKR and SAMP cohoused mice, SAMP favored gut enterobacterial growth (FIGS. 8A-H).

Together, the aforementioned analyses indicate that SAMP ileitis (1) had a Bacteroidetes-rich microbiome phenotype, (2) had increased likelihood to favor enterobacterial growth, (3) could develop cobblestone lesions unaffected by the presence of *Helicobacter* and norovirus in the gut, and (4) was not transmissible to AKR by long-term cohousing. Crossover experimentation with fecal transplantation from SAMP into GF-AKR mice, and vice versa, was considered to verify that SAMP ileitis was not microbiome-transmissible, but the experiment was not possible due to the lack of available GF-AKR mice at the time. Due to animal welfare concerns (SAMP-AKR mouse fights, with SAMP hierarchical dominance in cohousing experiments), we determined that SPLENDA® (sucralose) experiments could not be conducted cohousing adult AKR and SAMP mice.

SPLENDA® (sucralose) does not Alter the SAMP Cobblestone Ileitis Phenotype but Increases Tissue MPO Activity Due to the difficulties in cohousing AKR and SAMP mice and in controlling for the observed metagenome cage variability, we implemented the IsPreFeH protocol (Rodriguez-Palacios, A. et al., *Nat Commun.* 2015; 6:7577; Rodriguez-Palacios, A. et al., *Protoc Exch.* 2015) among all animals subjected to the SPLENDA® (sucralose) experiments, which was followed by individual animal housing and SPLENDA® (sucralose) supplementation for 42-47 days. Although low-dose supplementation resulted in transient body weight reduction during supplementation (generalized linear regression [GLM] P<0.0001), no changes were significant at higher doses. In addition, although fecal cultures showed that SPLENDA® (sucralose) promotes enterobacterial and maltodextrin-utilizing bacterial growth in SAMP, no evidence of systemic effects was present from culture of spleens, serum TNF levels, or blood glucose tolerance tests. Compared with the total number of anaerobes (TSA) and lactobacilli (MRS agar), the number of enterobacteria (LB) was significantly increased in SPLENDA® (sucralose)- supplemented SAMP mice. No differences were seen at 1, 3, or 14 days after supplementation (FIGS. 3A-G). Unexpectedly, SMAPgut and histological analyses of the ileum showed that SPLENDA® (sucralose) did not augment the ileal inflammation scores, the percentage of SM-abnormal mucosa, or the 3D-morphological features of cobblestone lesions in CD-prone (SAMP) mice at any of the 3 doses tested. More importantly, supplementation did not cause either ileitis or colitis in healthy (AKR) mice. In contrast, a well-validated quantitative enzymatic activity assay showed that the amount of MPO reactivity in the ileum of SAMP mice treated with the SPLENDA® (sucralose) FDA maximum approved dose (3.5 mg/mL) was 2.7-times higher compared with SAMP mice drinking plain water (219.1 vs 81.8 U/g, t test P=0.022). Controlling for multiple variables, analysis of ileal tissues of SAMP mice in experiment 3 (high-dose, 35 mg/mL) confirmed that increased increments of MPO activity occurred only in SPLENDA® (sucralose)-treated SAMP (2-way ANOVA F=4.08, P=0.055, controlling for significant interaction between SPLENDA® (sucralose) and organ [colon vs ileum], P=0.0515). Interestingly, the same doses of SPLENDA® (sucralose) had no effect on ileal MPO activity in AKR mice (i.e., experiment 3, 2-way ANOVA F=0.09, P>0.76). The MPO activity in the colon was lower compared with the ileum (2-way ANOVAs for AKR and SAMP, P=0.012 and P<0.0001), which was unaltered by SPLENDA® (sucralose) in both mouse lines (FIGS. 4A-E). These results suggested that SPLENDA® (sucralose) promoted the increase of intestinal MPO tissue reactivity ("biochemical inflammation") only in the gut wall of mice prone to IBD, without inducing major (noticeable histologic) microscopic changes associated with active inflammation. This finding is remarkable considering that subclinical inflammation (i.e., increased MPO and other inflammatory biomarkers, with no evidence of histological abnormalities) has recently been observed in healthy twins of monozygotic and dizygotic discordant pairs with IBD compared with healthy nontwin relatives. This further supports the concept that a combination of genetic and environmental factors predisposes individuals to biochemical (reactivity) inflammation in IBD.

SPLENDA® (sucralose) Promotes Gut Microbiome Dysbiosis and Proteobacteria in SAMP and AKR Mice Differences in fecal bacterial composition were assessed using 16S microbiome analysis (1.42 million V4 16S rRNA gene sequences from 20 mice; 70,879 reads per sample passed quality control filters; 99.36% had a Blast hit match in the 16S database). Corroborating the culture findings from SAMP mice treated with SPLENDA® (sucralose), analysis revealed that the most consistent effect that SPLENDA® (sucralose) supplementation had on the mouse microbiome was a significantly widespread promotion of bacterial species across the 5 microbial classes identified within the Proteobacteria phylum (Alphaproteobacteria, Betaproteobacteria, Epsilonproteobacteria, Deltaproteobacteria, and Gammaproteobacteria). Comparison of proteobacterial mean abundances between AKR and SAMP indicates that SAMP were likely to have more Proteobacteria in the control (6/6; 1-tail sign P=0.016) (see culture agars from cohouse AKR-SAMP mice in FIG. 8E) and SPLENDA® (sucralose) groups (5/6; 1-tail sign P=0.109) (FIGS. 5A-D). Comparatively, microbiome analysis also showed that subtle differences exist between AKR and SAMP mice, which cluster them separately as mouse strains. In addition, SPLENDA® (sucralose) altered the gut microbiome by reducing some other phyla, while no significant effect was observed in Bacteroidetes or Firmicutes (e.g., lactobacilli and clostridia), which also clustered the mice according to the dietary impact on their gut microbes (FIGS. 5A-D). Culture data from SPLENDA® (sucralose)-treated SAMP compared with mice drinking water showed that SPLENDA® (sucralose) had no effect on the counts of lactobacilli (MRS agar), total bacteria (TSA), or anaerobic clostridial species (MRS, TSA and meat liver agars; GLM of normalized $\log_{10}$ adjusted P>0.2), whereas it promoted the remarkable growth of Escherichia coli in the feces of mice. Of interest, E. coli overgrowth apparently occurred at the expense of displacing, at least, cultivable Streptococcus-like organisms, which were evident in the feces of mice drinking only water (FIGS. 6A-E). Because several lines of evidence indicated that SPLENDA® (sucralose) promotes MPO tissue reactivity and the overgrowth of E. coli (Gammaproteobacteria) in intestinal content (i.e., feces), we then used qPCR and fluorescence in situ hybridization (FISH) analysis to determine whether ileal tissue from SAMP mice treated with SPLENDA® (sucralose) would have mucosal-associated dysbiosis and increased bacterial infiltration into deep intestinal layers.

SPLENDA® (Sucralose) Causes Distinct Ileal Tissue Microbiota with Increased Bacterial Malx Gene in SAMP Mice Multivariate quantitative analysis of DNA copy numbers in ileal (full thickness) tissue samples from SAMP mice using 7 specific primers for various bacterial families/species revealed that supplemented mice had a distinct (dysbiotic) microbiome profile when compared with untreated animals (see enrichment of eubacteria, lactobacilli, and the contribution of E. coli illustrated as 2-dimensional vectors in FIG. 7A). Although SAMP ileitis has been known to be a highly segmental disease of the small intestine, blinded FISH analysis of SAMP mice confirmed that the ilea of SPLENDA® (sucralose)-treated SAMP mice had increased numbers and larger clusters of bacteria within the villi compared with untreated SAMP and AKR mice. These bacterial clusters positively hybridized with an E. coli probe and a probe to malX, a gene that encodes a maltodextrin-binding protein of the maltose/maltodextrin metabolism system. Of translational value, the presence of FISH-positive clusters was almost imperceptible in ileitis-resistant AKR mice in both groups, with and without the sucralose/maltodextrin (SPLENDA® (sucralose)) supplementation (FIGS. 7B and C). This observation further supports that sucralose/maltodextrin have a dysbiotic effect in ileitis-prone SAMP mice, but not in healthy AKR mice.

Together, our data indicate that sucralose/maltodextrin daily supplementation in the water (for 6 weeks) promotes bacterial dysbiosis with proliferation of Proteobacteria species, including E. coli, and increased bacterial invasiveness into villi tissue, which may in turn increase the MPO reactivity of ileal tissues during the course of murine cobblestone CD-like ileitis.

From the above description of the present disclosure, those skilled in the art will perceive improvements, changes and modifications. Such improvements, changes, and modifications are within the skill of those in the art and are intended to be covered by the appended claims. All patents, patent applications, and publication cited herein are incorporated by reference in their entirety.

The following is claimed:

1. A method for reducing or alleviating inflammation in the digestive tract of a subject in need thereof that consumes a disruptive dietary component, the method comprising:

assaying a previously obtained fecal sample from the subject for the presence of one or more gram-negative Proteobacteria and an activity level of a peroxidase enzyme; and decreasing ingestion of the disruptive dietary component by the subject in which the abundance of the one or more gram-negative Proteobacteria and the activity level of the peroxidase enzyme are increased as compared to control levels;

wherein the subject is suffering from, or suspected of suffering from, inflammation in the digestive tract;

wherein the disruptive dietary component is a non-caloric artificial sweetener selected from the group consisting of sucralose, maltodextrin, saccharin, acesulfame, aspartame, neotame, and combinations thereof.

2. The method of claim 1, wherein the subject is suffering from or suspected of suffering from chronic gastritis.

3. The method of claim 1, wherein the subject is suffering from or suspected of suffering from an inflammatory bowel disease.

4. The method of claim 1, wherein the subject is suffering from or suspected of suffering from Crohn's disease or ulcerative colitis.

5. The method of claim 1, wherein the gram-negative Proteobacteria are selected from the group consisting of *Escherichia, Salmonella, Vibrio, Helicobacter, Yersinia* and Legionellales.

6. The method of claim 1, wherein the gram-negative Proteobacteria is *E. coli*.

7. The method of claim 1, wherein the non-caloric artificial sweetener is sucralose.

8. The method of claim 1, wherein the enzyme peroxidase is myeloperoxidase.

9. A method for reducing or alleviating inflammation in the digestive tract of a subject in need thereof that consumes a non-caloric artificial sweetener, the method comprising:

assaying a previously obtained fecal sample from the subject for the presence of *E. coli* and an activity level of myeloperoxidase (MPO); and decreasing ingestion of the non-caloric artificial sweetener by the subject in which the abundance of the *E. coli* and the activity level of the MPO are increased as compared to control levels;

wherein the subject is suffering from, or suspected of suffering from, inflammatory bowel disease.

* * * * *